US007700595B2

(12) United States Patent
Hu et al.

(10) Patent No.: US 7,700,595 B2
(45) Date of Patent: Apr. 20, 2010

(54) CINNOLINE COMPOUNDS

(75) Inventors: Baihua Hu, Audubon, PA (US); Jay E. Wrobel, Lawrenceville, NJ (US); Michael David Collini, Clifton Heights, PA (US); Rayomand J. Unwalla, Eagleville, PA (US)

(73) Assignee: Wyeth LLC, Madison, NJ (US)

( * ) Notice: Subject to any disclaimer, the term of this patent is extended or adjusted under 35 U.S.C. 154(b) by 415 days.

(21) Appl. No.: 11/365,750

(22) Filed: Mar. 1, 2006

(65) Prior Publication Data

US 2006/0252757 A1 Nov. 9, 2006

Related U.S. Application Data

(60) Provisional application No. 60/657,296, filed on Mar. 1, 2005.

(51) Int. Cl.
*C07D 237/28* (2006.01)
*C07D 413/12* (2006.01)
*A61K 31/502* (2006.01)
*A61K 31/5355* (2006.01)
*A61P 9/10* (2006.01)
*A61P 3/10* (2006.01)
*A61P 25/28* (2006.01)

(52) U.S. Cl. .................... 514/248; 514/234.5; 544/116; 544/235

(58) Field of Classification Search ................. 514/248, 514/234.5; 544/235, 116
See application file for complete search history.

(56) References Cited

U.S. PATENT DOCUMENTS

| 5,324,839 | A | 6/1994 | Clemence et al. | |
|---|---|---|---|---|
| 6,169,088 | B1 * | 1/2001 | Matsuno et al. | 514/252.16 |
| 6,831,175 | B2 * | 12/2004 | Li et al. | 546/187 |
| 2002/0188004 | A1 | 12/2002 | Schnute | |
| 2003/0158198 | A1 | 8/2003 | Lee et al. | |
| 2006/0019975 | A1 * | 1/2006 | Humphrey et al. | 514/266.22 |

FOREIGN PATENT DOCUMENTS

| BE | 774033 | | 4/1972 |
|---|---|---|---|
| BE | 832412 | | 8/1974 |
| EP | 498723 | | 2/1992 |
| EP | 1270535 | | 6/1992 |
| EP | 829479 | | 9/1993 |
| EP | 635492 | | 7/1994 |
| EP | 752421 | | 7/1996 |
| EP | 796848 | | 3/1997 |
| EP | 867432 | | 3/1998 |
| FR | 2528838 | * | 12/1983 |
| FR | 2816618 | | 11/2000 |
| FR | 2856062 | * | 12/2004 |
| JP | 10310579 | | 11/1998 |
| WO | WO 92/20642 | | 11/1992 |
| WO | WO 96/11902 | | 4/1996 |
| WO | WO 97/14681 | | 4/1997 |
| WO | WO 98/14431 | | 4/1998 |
| WO | WO 00/53179 | | 9/2000 |
| WO | WO 01/34609 | | 5/2001 |
| WO | WO 01/70227 | | 9/2001 |
| WO | WO 02/04443 | | 1/2002 |
| WO | WO 02/04444 | | 1/2002 |
| WO | WO 0212228 | * | 2/2002 |
| WO | WO 02/30426 | | 4/2002 |
| WO | WO 02/36734 | | 5/2002 |
| WO | WO 02/42250 | | 5/2002 |
| WO | WO 02/089738 | | 11/2002 |
| WO | WO 03/002532 | | 1/2003 |
| WO | WO 03051366 | * | 6/2003 |
| WO | WO 03/062209 | | 7/2003 |
| WO | WO 03/066604 | | 8/2003 |
| WO | WO 03/072558 | | 9/2003 |
| WO | WO 03/080578 | | 10/2003 |
| WO | WO 2005051304 | * | 11/2003 |
| WO | WO 2004007478 | * | 1/2004 |
| WO | WO 2004007480 | * | 1/2004 |
| WO | WO 2004/072042 | | 8/2004 |
| WO | WO2006028957 | * | 9/2004 |
| WO | WO 2006070284 | * | 12/2004 |
| WO | WO 2006/028957 | | 3/2006 |

OTHER PUBLICATIONS

Alford, et al., Journal of the Chemical Society (1952) 3009-17.*
Allen, et al., JACS (1951), 73, 5850-6.*
Schatz, et al., Helvetica Chimica Acta (1968), 51(8), 1919-31.*
Allen, C. F. H. et al., "Some 3, 4-diphenylcinnolines and related compounds", *Journal of the American Chemical Society*, vol. 73, No. 12, pp. 5850-5856 (1951).
Ames, D. E. et al., "Cinnolines. Part XII. 1,3-Diphenyl-2H-pyrrolo[3,4-c]cinnoline. Structure and N-ethyl derivatives", *Journal of the Chemical Society*, pp. 1795-1798 (1969).
Atkinson, C.M. et al., "Cinnolines. Part XIV. N-Oxides of 4-arylcinnolines. Conversion of 4-substituted cinnolines into indoles", *Journal of the Chemical Society*, pp. 1649-1652, (1947).
Chapoulaud V., "Synthesis of 4, 8-diarylcinnolines and quinazolines with potential applications in nonlinear optics. Diazines. Part 28", *Tetrahedron*, vol. 56, No. 30, pp. 5499-5507, (2000).
Jordan, D. B., et al., "Tight Binding Inhibitors of Scytalone Dehydratase: Effects of Site-Directed Mutations", *Biochemistry*, vol. 39, No. 29, pp. 8593-8602, (2000).
Matsubara, Y. et al., "Electrochemical transformation of 4-cyanocinnolines into 4(1H)-cinnolones", *Tetrahedron*, Vo. 41, No. 41, pp. 7901-7904, (2000).
Matsuno, K. et al., "Potent and selective inhibitors of platelet-derived growth factor receptor phosphorylation. 3. Replacement of quinazoline moiety and improvement of metabolic polymorphism of 4-[4-N-substituted (thio)carbamoyl)-1-piperazinyl]-6,7-dimethoxyquinazoline derivatives", *Journal of Medicinal Chemistry*, vol. 46, No. 23, pp. 4910-4925, (2003).
Ross, B. S. et al., "Tetracyclic pyridazines as potential psychopharmacological agents", *Journal of Medicinal Chemistry*, vol. 28, No. 7, pp. 870-875, (1985).
Stoermer, R. et al., "Eine neue Synthese von Cinnolin-Derivaten", *Chemishe Berichte*, vol. 42, pp. 3115-3132 (1909).
Yamazaki, T. et al., "Cinnoline Chemistry XIII. 4-Aziridinocinnolines (1)", *Journal of Heterocyclic Chemistry*, vol. 15, pp. 1039-1040, (1978).

* cited by examiner

*Primary Examiner*—James O Wilson
*Assistant Examiner*—Cecilia M Jaisle
(74) *Attorney, Agent, or Firm*—Ram W. Sabnis

(57) ABSTRACT

This invention relates generally to cinnoline-based modulators of Liver X receptors (LXRs) and related methods.

45 Claims, No Drawings

SEQUENCE LISTING

```
<160> NUMBER OF SEQ ID NOS: 6

<210> SEQ ID NO 1
<211> LENGTH: 22
<212> TYPE: DNA
<213> ORGANISM: Homo sapiens

<400> SEQUENCE: 1
caacatgaat gccattttcc aa                                                22

<210> SEQ ID NO 2
<211> LENGTH: 21
<212> TYPE: DNA
<213> ORGANISM: Homo sapiens

<400> SEQUENCE: 2
ataatcccct gaacccaagg a                                                 21

<210> SEQ ID NO 3
<211> LENGTH: 25
<212> TYPE: DNA
<213> ORGANISM: Artificial Sequence
<220> FEATURE:
<223> OTHER INFORMATION: Probe sequence

<400> SEQUENCE: 3
taaagccatg ccctctgcag gaaca                                             25

<210> SEQ ID NO 4
<211> LENGTH: 15
<212> TYPE: DNA
<213> ORGANISM: Homo sapiens

<400> SEQUENCE: 4
agggcgggcg cagat                                                        15

<210> SEQ ID NO 5
<211> LENGTH: 24
<212> TYPE: DNA
<213> ORGANISM: Homo sapiens

<400> SEQUENCE: 5
ggttgttgat aagctgaagc atgt                                              24
```

```
-continued

<210> SEQ ID NO 6
<211> LENGTH: 24
<212> TYPE: DNA
<213> ORGANISM: Artificial Sequence
<220> FEATURE:
<223> OTHER INFORMATION: Probe sequence

<400> SEQUENCE: 6
tcgaaagtgc aatccatggc tccg                                          24
```

CINNOLINE COMPOUNDS

CROSS REFERENCE TO RELATED APPLICATIONS

This application claims the benefit of U.S. Provisional Application No.: 60/657,296, filed on Mar. 1, 2005, which is incorporated by reference in its entirety.

TECHNICAL FIELD

This invention relates generally to cinnoline-based modulators of Liver X receptors (LXRs) and related methods.

BACKGROUND

Atherosclerosis is among the leading causes of death in developed countries. Some of the independent risk factors associated with atherosclerosis include the presence of relatively high levels of serum LDL cholesterol and relatively low levels of serum HDL cholesterol in affected patients. As such, some anti-atherosclerotic therapy regimens include the administration of agents (e.g., statins) to reduce elevated serum LDL cholesterol levels.

Agents that increase patient HDL cholesterol levels can also be useful in anti-atherosclerotic therapy regimens. HDL cholesterol is believed to play a major role in the transport of cholesterol from peripheral tissues to the liver for metabolism and excretion (this process is sometimes referred to as "reverse cholesterol transport"). ABCA1 is a transporter gene involved in HDL production and reverse cholesterol transport. Upregulation of ABCA1 can therefore result in increased reverse cholesterol transport as well as inhibition of cholesterol absorption in the gut. In addition, HDL is also believed to inhibit the oxidation of LDL cholesterol, reduce the inflammatory response of endothelial cells, inhibit the coagulation pathway, and promote the availability of nitric oxide.

Liver X receptors (LXRs), originally identified in the liver as orphan receptors, are members of the nuclear hormone receptor super family and are believed to be involved in the regulation of cholesterol and lipid metabolism. LXRs are ligand-activated transcription factors and bind to DNA as obligate heterodimers with retinoid X receptors. While LXRα is generally found in tissues such as liver, kidney, adipose tissue, intestine and macrophages, LXRβ displays a ubiquitous tissue distribution pattern. Activation of LXRs by oxysterols (endogenous ligands) in macrophages results in the expression of several genes involved in lipid metabolism and reverse cholesterol transport including the aforementioned ABCA1; ABCG1; and ApoE.

Studies have been conducted in LXRα knock-out (k/o), LXRβ k/o and double k/o mice to determine the physiological role of LXRs in lipid homeostasis and atherosclerosis. The data from these studies suggested that in double k/o mice on normal chow diet, increased cholesterol accumulation was observed in macrophages (foam cells) of the spleen, lung and arterial wall. The increased cholesterol accumulation was believed to be associated with the presence of reduced serum HDL cholesterol and increased LDL cholesterol, even though the total cholesterol levels in the mice were about normal. While LXRα k/o mice did not appear to show significant changes in hepatic gene expression, LXRβ k/o mice showed 58% decrease in hepatic ABCA1 expression and 208% increase in SREBP1c expression suggesting that LXRβ may be involved in the regulation of liver SREBP1c expression.

Data obtained from studies employing two different atherosclerotic mouse models (ApoE k/o and LDLR k/o) suggest that agonists of LXRα or β can be relatively effective in upregulating ABCA1 expression in macrophages. For example, inhibition of atherosclerotic lesions could be observed when ApoE k/o and LDLR k/o mice were treated with LXRα or β agonists for 12 weeks. The tested agonists were observed to have variable effects on serum cholesterol and lipoprotein levels and appeared to cause a relatively significant increase in serum HDL cholesterol and triglyceride levels. These in vivo data were found to be consistent with in vitro data obtained for the same agonists in macrophages.

In addition to the lipid and triglyceride effects described above, it is also believed that activation of LXRs results in the inhibition of inflammation and proinflammatory gene expression. This hypothesis is based on data obtained from studies employing three different models of inflammation (LPS-induced sepsis, acute contact dermatitis of the ear and chronic atherosclerotic inflammation of the artery wall). These data suggest that LXR modulators can mediate both the removal of cholesterol from the macrophages and the inhibition of vascular inflammation.

SUMMARY

This invention relates generally to cinnoline-based modulators of LXRs and related methods and compositions.

In one aspect, this invention relates to compounds having formula (I):

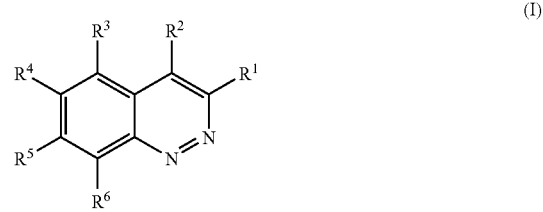

(I)

in which:

$R^1$ can be:

(i) hydrogen; or (ii) $C_1$-$C_{20}$ alkyl or $C_1$-$C_{20}$ haloalkyl, each of which is optionally substituted with from 1-10 $R^a$; or (iii) $C_6$-$C_{18}$ aryl or heteroaryl including 5-16 atoms, each of which is optionally substituted with from 1-10 $R^b$; or (iv) $C_7$-$C_{20}$ aralkyl or heteroaralkyl including 6-20 atoms, each of which is optionally substituted with from 1-10 $R^c$; or (v) $C_2$-$C_{20}$ alkenyl or $C_2$-$C_{20}$ alkynyl, each of which is optionally substituted with from 1-10 $R^d$;

(vi) $C_3$-$C_{20}$ cycloalkyl or $C_3$-$C_{20}$ halocycloalkyl, optionally substituted with from 1-10 $R^e$; or (vii) $C_3$-$C_{20}$ cycloalkenyl, heterocyclyl including 3-20 atoms, or heterocycloalkenyl including 3-20 atoms, each of which is optionally substituted with from 1-10 $R^f$; or (viii) —C(O)NR$^g$R$^h$; —OC(O)NR$^g$R$^h$; —C(O)R$^i$; —C(O)OR$^i$; —OC(O)R$^i$; —C(O)SR$^i$; —SC(O)R$^i$; —C(S)SR$^i$; —SC(S)R$^i$; —NR$^j$C(O)R$^i$; —NR$^j$C(O)OR$^i$; —NR$^j$C(O)NR$^g$R$^h$; —S(O)$_n$R$^k$; —NR$^j$S(O)$_n$R$^i$; —C(NR$^m$)R$^i$; or —P(O)(OR$^g$)(OR$^h$);

$R^2$ can be:

(i) $C_6$-$C_{18}$ aryl or heteroaryl including 5-16 atoms, each of which is optionally substituted with from 1-10 $R^b$; or (ii) $C_7$-$C_{20}$ aralkyl or heteroaralkyl including 6-20 atoms, each of which is optionally substituted with from 1-10 $R^c$; or (iii) $C_3$-$C_{20}$ cycloalkyl or $C_3$-$C_{20}$ halocycloalkyl, optionally substituted with from 1-10 $R^e$; or (iv) $C_3$-$C_{20}$ cycloalkenyl, heterocyclyl including 3-20 atoms, or heterocycloalkenyl including 3-20 atoms, each of which is optionally substituted with from 1-10 $R^f$;

each of $R^3$, $R^4$, $R^5$, and $R^6$ can be, independently:

(i) hydrogen, halo; $NR^gR^h$; nitro; azido; hydroxy; $C_1$-$C_{20}$ alkoxy or $C_1$-$C_{20}$ haloalkoxy, each of which is optionally substituted with from 1-10 $R^a$; $C_6$-$C_{18}$ aryloxy or heteroaryloxy including 5-16 atoms, each of which is optionally substituted with from 1-10 $R^b$; $C_7$-$C_{20}$ aralkoxy or heteroaralkoxy including 6-20 atoms, each of which is optionally substituted with from 1-10 $R^c$; $C_3$-$C_{20}$ cycloalkoxy or $C_3$-$C_{20}$ halocycloalkoxy, each of which is optionally substituted with from 1-10 $R^e$; $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; mercapto; $C_1$-$C_{20}$ thioalkoxy or $C_1$-$C_{20}$ thiohaloalkoxy, each of which is optionally substituted with from 1-10 $R^a$; $C_6$-$C_{18}$ thioaryloxy or thioheteroaryloxy including 5-16 atoms, each of which is optionally substituted with from 1-10 $R^b$; $C_7$-$C_{20}$ thioaralkoxy or thioheteroaralkoxy including 6-20 atoms, each of which is optionally substituted with from 1-10 $R^c$; $C_3$-$C_{20}$ thiocycloalkoxy or $C_3$-$C_{20}$ thiohalocycloalkoxy, each of which is optionally substituted with from 1-10 $R^e$; $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC$(O)$R^i$; —$NR^jC$(O)$OR^i$; —$NR^jC$(O)$NR^gR^h$; —S(O)$_nR^k$; —$NR^jS$(O)$_nR^i$; —C($NR^m$)$R^i$; or —P(O)($OR^g$)($OR^h$); or (ii) $C_1$-$C_{20}$ alkyl or $C_1$-$C_{20}$ haloalkyl, each of which is optionally substituted with from 1-10 $R^a$; or (iii) $C_3$-$C_{20}$ cycloalkyl or $C_3$-$C_{20}$ halocycloalkyl, optionally substituted with from 1-10 $R^e$; or (iv) $C_3$-$C_{20}$ cycloalkenyl, heterocyclyl including 3-20 atoms, or heterocycloalkenyl including 3-20 atoms, each of which is optionally substituted with from 1-10 $R^f$; or (v) $C_2$-$C_{20}$ alkenyl or $C_2$-$C_{20}$ alkynyl, each of which is optionally substituted with from 1-10 $R^d$; or (vi) $C_7$-$C_{20}$ aralkyl or heteroaralkyl including 6-20 atoms, each of which is optionally substituted with from 1-10 $R^c$; or (vii) $C_6$-$C_{18}$ aryl or heteroaryl including 5-16 atoms, each of which is optionally substituted with from 1-10 $R^b$;

$R^a$ at each occurrence can be, independently $NR^gR^h$; nitro; azido; hydroxy; oxo; thioxo; =$NR^m$; $C_1$-$C_{20}$ alkoxy; $C_1$-$C_{20}$ haloalkoxy; $C_6$-$C_{18}$ aryloxy or heteroaryloxy including 5-16 atoms, each of which is optionally substituted with from 1-10 $R^b$; $C_7$-$C_{20}$ aralkoxy or heteroaralkoxy including 6-20 atoms, each of which is optionally substituted with from 1-10 $R^c$; $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy or thioheteroaryloxy including 5-16 atoms, each of which is optionally substituted with from 1-10 $R^b$; $C_7$-$C_{20}$ thioaralkoxy or thioheteroaralkoxy including 6-20 atoms, each of which is optionally substituted with from 1-10 $R^c$; $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC$(O)$R^i$; —$NR^jC$(O)$OR^i$; —$NR^jC$(O)$NR^gR^h$; —S(O)$_nR^k$; —$NR^jS$(O)$_nR^i$; —C($NR^m$)$R^i$; or —P(O)($OR^g$)($OR^h$);

$R^b$ at each occurrence can be, independently:

(i) halo; $NR^gR^h$; nitro; azido; hydroxy; $C_1$-$C_{20}$ alkoxy or $C_1$-$C_{20}$ haloalkoxy, each of which is optionally substituted with from 1-10 $R^a$; $C_6$-$C_{18}$ aryloxy or heteroaryloxy including 5-16 atoms, each of which is optionally substituted with from 1-10 $R^b$ or $R^{b'}$; $C_7$-$C_{20}$ aralkoxy or heteroaralkoxy including 6-20 atoms, each of which is optionally substituted with from 1-10 $R^c$; $C_3$-$C_{16}$ cycloalkoxy or $C_3$-$C_{16}$ halocycloalkoxy, each of which is optionally substituted with from 1-10 $R^e$; $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; mercapto; $C_1$-$C_{20}$ thioalkoxy or $C_1$-$C_{20}$ thiohaloalkoxy, each of which is optionally substituted with from 1-10 $R^a$; $C_6$-$C_{18}$ thioaryloxy or thioheteroaryloxy including 5-16 atoms, each of which is optionally substituted with from 1-10 $R^b$; $C_7$-$C_{20}$ thioaralkoxy or thioheteroaralkoxy including 6-20 atoms, each of which is optionally substituted with from 1-10 $R^c$; $C_3$-$C_{16}$ thiocycloalkoxy or $C_3$-$C_{16}$ thiohalocycloalkoxy, each of which is optionally substituted with from 1-10 $R^e$; $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC$(O)$R^i$; —$NR^jC$(O)$OR^i$; —$NR^jC$(O)$NR^gR^h$; —S(O)$_nR^k$; —$NR^jS$(O)$_nR^i$; —C($NR^m$)$R^i$; or —P(O)($OR^g$)($OR^h$); or (ii) $C_1$-$C_{20}$ alkyl or $C_1$-$C_{20}$ haloalkyl, each of which is optionally substituted with from 1-10 $R^a$; or (iii) $C_3$-$C_{20}$ cycloalkyl or $C_3$-$C_{20}$ halocycloalkyl, optionally substituted with from 1-10 $R^e$; or (iv) $C_3$-$C_{20}$ cycloalkenyl, heterocyclyl including 3-20 atoms, or heterocycloalkenyl including 3-20 atoms, each of which is optionally substituted with from 1-10 $R^f$; or (v) $C_2$-$C_{20}$ alkenyl or $C_2$-$C_{20}$ alkynyl, each of which is optionally substituted with from 1-10 $R^d$; or (vi) $C_7$-$C_{20}$ aralkyl or heteroaralkyl including 6-20 atoms, each of which is optionally substituted with from 1-10 $R^c$; or (vii) $C_6$-$C_{18}$ aryl or heteroaryl including 5-16 atoms, each of which is optionally substituted with from 1-10 $R^{b'}$;

$R^{b'}$ at each occurrence can be, independently, halo; $NR^gR^h$; nitro; azido; hydroxy; $C_1$-$C_{20}$ alkyl, $C_1$-$C_{20}$ haloalkyl, $C_2$-$C_{20}$ alkenyl; $C_2$-$C_{20}$ alkynyl; $C_3$-$C_{20}$ cycloalkyl; $C_3$-$C_{20}$ halocycloalkyl; $C_3$-$C_{20}$ cycloalkenyl, heterocyclyl including 3-20 atoms; heterocycloalkenyl including 3-20 atoms; $C_7$-$C_{20}$ aralkyl; heteroaralkyl including 6-20 atoms; $C_1$-$C_{20}$ alkoxy; $C_1$-$C_{20}$ haloalkoxy; $C_6$-$C_{18}$ aryloxy or heteroaryloxy including 5-16 atoms; $C_7$-$C_{20}$ aralkoxy or heteroaralkoxy including 6-20 atoms; $C_3$-$C_{16}$ cycloalkoxy or $C_3$-$C_{16}$ halocycloalkoxy; $C_3$-$C_{20}$ cycloalkenyloxy, heterocyclyloxy including 3-20 atoms, or heterocycloalkenyloxy including 3-20 atoms; mercapto; $C_1$-$C_{20}$ thioalkoxy or $C_1$-$C_{20}$ thiohaloalkoxy; $C_6$-$C_{18}$ thioaryloxy or thioheteroaryloxy including 5-16 atoms; $C_7$-$C_{20}$ thioaralkoxy or thioheteroaralkoxy including 6-20 atoms; $C_3$-$C_{16}$ thiocycloalkoxy or $C_3$-$C_{16}$ thiohalocycloalkoxy; $C_3$-$C_{20}$ thiocycloalkenyloxy, thioheterocyclyloxy including 3-20 atoms, or thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC$(O)$R^i$; —$NR^jC$(O)$OR^i$; —$NR^jC$(O)$NR^gR^h$; —S(O)$_nR^k$; —$NR^jS$(O)$_nR^i$; —C($NR^m$)$R^i$; or —P(O)($OR^g$)($OR^h$);

$R^c$ at each occurrence can be, independently:

(i) halo; $NR^gR^h$; nitro; azido; hydroxy; oxo; thioxo; $=NR^m$; $C_1$-$C_{20}$ alkoxy or $C_1$-$C_{20}$ haloalkoxy, each of which is optionally substituted with from 1-10 $R^a$; $C_6$-$C_{18}$ aryloxy or heteroaryloxy including 5-16 atoms, each of which is optionally substituted with from 1-10 $R^b$; $C_7$-$C_{20}$ aralkoxy or heteroaralkoxy including 6-20 atoms, each of which is optionally substituted with from 1-10 $R^c$ or $R^{c'}$; $C_3$-$C_{16}$ cycloalkoxy or $C_3$-$C_{16}$ halocycloalkoxy, each of which is optionally substituted with from 1-10 $R^e$; $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; mercapto; $C_1$-$C_{20}$ thioalkoxy or $C_1$-$C_{20}$ thiohaloalkoxy, each of which is optionally substituted with from 1-10 $R^a$; $C_6$-$C_{18}$ thioaryloxy or thioheteroaryloxy including 5-16 atoms, each of which is optionally substituted with from 1-10 $R^b$; $C_7$-$C_{20}$ thioaralkoxy or thioheteroaralkoxy including 6-20 atoms, each of which is optionally substituted with from 1-10 $R^c$; $C_3$-$C_{16}$ thiocycloalkoxy or $C_3$-$C_{16}$ thiohalocycloalkoxy, each of which is optionally substituted with from 1-10 $R^e$; $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^j$C(O)$R^i$; —$NR^j$C(O)$OR^i$; —$NR^j$C(O)$NR^gR^h$; —S(O)$_n$$R^k$; —$NR^j$S(O)$_n$$R^i$; —C($NR^m$)$R^i$; or —P(O)($OR^g$)($OR^h$); or (ii) $C_1$-$C_{20}$ alkyl or $C_1$-$C_{20}$ haloalkyl, each of which is optionally substituted with from 1-10 $R^a$; or (iii) $C_3$-$C_{20}$ cycloalkyl or $C_3$-$C_{20}$ halocycloalkyl, optionally substituted with from 1-10 $R^e$; or (iv) $C_3$-$C_{20}$ cycloalkenyl, heterocyclyl including 3-20 atoms, or heterocycloalkenyl including 3-20 atoms, each of which is optionally substituted with from 1-10 $R^f$; or (v) $C_2$-$C_{20}$ alkenyl or $C_2$-$C_{20}$ alkynyl, each of which is optionally substituted with from 1-10 $R^d$; or (vi) $C_7$-$C_{20}$ aralkyl or heteroaralkyl including 6-20 atoms, each of which is optionally substituted with from 1-10 $R^c$ or $R^{c'}$; or (vii) $C_6$-$C_{18}$ aryl or heteroaryl including 5-16 atoms, each of which is optionally substituted with from 1-10 $R^b$;

$R^d$ at each occurrence can be, independently, halo, $NR^gR^h$; nitro; azido; hydroxy; oxo; thioxo; $=NR^m$; $C_1$-$C_{20}$ alkoxy; $C_1$-$C_{20}$ haloalkoxy; $C_6$-$C_{18}$ aryloxy; heteroaryloxy including 5-16 atoms; $C_7$-$C_{20}$ aralkoxy; heteroaralkoxy including 6-20 atoms; $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy; thioheteroaryloxy including 5-16 atoms; $C_7$-$C_{20}$ thioaralkoxy; thioheteroaralkoxy including 6-20 atoms; $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^j$C(O)$R^i$; —$NR^j$C(O)$OR^i$; —$NR^j$C(O)$NR^gR^h$; —S(O)$_n$$R^k$; —$NR^j$S(O)$_n$$R^i$; —C($NR^m$)$R^i$; or —P(O)($OR^g$)($OR^h$);

$R^{c'}$ can be oxo; thioxo; $=NR^m$; or $R^{b'}$;

$R^e$ at each occurrence can be, independently:

(i) $NR^gR^h$; nitro; azido; hydroxy; oxo; thioxo; $=NR^m$; $C_1$-$C_{20}$ alkoxy; $C_1$-$C_{20}$ haloalkoxy; $C_6$-$C_{18}$ aryloxy; heteroaryloxy including 5-16 atoms; $C_7$-$C_{20}$ aralkoxy; heteroaralkoxy including 6-20 atoms; $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy; thioheteroaryloxy including 5-16 atoms; $C_7$-$C_{20}$ thioaralkoxy; thioheteroaralkoxy including 6-20 atoms; $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^j$C(O)$R^i$; —$NR^j$C(O)$OR^i$; —$NR^j$C(O)$NR^gR^h$; —S(O)$_n$$R^k$; —$NR^j$S(O)$_n$$R^i$; —C($NR^m$)$R^i$; or —P(O)($OR^g$)($OR^h$); or (ii) $C_2$-$C_{20}$ alkenyl or $C_2$-$C_{20}$ alkynyl, each of which is optionally substituted with from 1-10 $R^d$; or (iii) $C_6$-$C_{18}$ aryl or heteroaryl including 5-16 atoms, each of which is optionally substituted with from 1-10 $R^b$;

$R^f$ at each occurrence can be, independently:

(i) halo, $NR^gR^h$; nitro; azido; hydroxy; oxo; thioxo; $=NR^m$; $C_1$-$C_{20}$ alkoxy; $C_1$-$C_{20}$ haloalkoxy; $C_6$-$C_{18}$ aryloxy; heteroaryloxy including 5-16 atoms; $C_7$-$C_{20}$ aralkoxy; heteroaralkoxy including 6-20 atoms; $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy; thioheteroaryloxy including 5-16 atoms; $C_7$-$C_{20}$ thioaralkoxy; thioheteroaralkoxy including 6-20 atoms; $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^j$C(O)$R^i$; —$NR^j$C(O)$OR^i$; —$NR^j$C(O)$NR^gR^h$; —S(O)$_n$$R^k$; —$NR^j$S(O)$_n$$R^i$; —C($NR^m$)$R^i$; or —P(O)($OR^g$)($OR^h$); or (ii) $C_2$-$C_{20}$ alkenyl or $C_2$-$C_{20}$ alkynyl, each of which is optionally substituted with from 1-10 $R^a$; or (iii) $C_6$-$C_{18}$ aryl or heteroaryl including 5-16 atoms, each of which is optionally substituted with from 1-10 $R^b$;

each of $R^g$, $R^h$, $R^i$, and $R^j$, at each occurrence can be, independently:

(i) hydrogen; or (ii) $C_1$-$C_{20}$ alkyl or $C_1$-$C_{20}$ haloalkyl, each of which is optionally substituted with from 1-10 $R^a$;

(iii) $C_2$-$C_{20}$ alkenyl or $C_2$-$C_{20}$ alkynyl, each of which is optionally substituted with from 1-10 $R^d$; or (iv) $C_3$-$C_{20}$ cycloalkyl or $C_3$-$C_{20}$ halocycloalkyl, each of which is optionally substituted with from 1-10 $R^e$; or (v) $C_3$-$C_{20}$ cycloalkenyl, heterocyclyl including 3-16 atoms, or heterocycloalkenyl including 3-16 atoms, each of which is optionally substituted with from 1-10 $R^f$; or (vi) $C_7$-$C_{20}$ aralkyl or heteroaralkyl including 6-20 atoms, each of which is optionally substituted with from 1-10 $R^c$; or (vii) $C_6$-$C_{18}$ aryl or heteroaryl including 5-16 atoms, each of which is optionally substituted with from 1-10 $R^b$;

$R^k$ can be $R^i$, $OR^i$, or $NR^gR^h$;

$R^m$ can be hydrogen; $C_1$-$C_{12}$ alkyl or $C_1$-$C_{12}$ haloalkyl, each of which is optionally substituted with from 1-5 $R^a$; $C_2$-$C_{20}$ alkenyl; $C_2$-$C_{20}$ alkynyl; $C_7$-$C_{20}$ aralkyl; heteroaralkyl including 6-20 atoms; $C_3$-$C_{20}$ cycloalkyl; $C_3$-$C_{20}$ cycloalkenyl; heterocyclyl including 3-20 atoms; heterocycloalkenyl including 3-20 atoms; $C_6$-$C_{18}$ aryl; heteroaryl including 5-16 atoms; $NR^gR^h$ or $OR^i$; and n can be 0, 1 or 2; a compound of formula (I) can be a salt or a prodrug thereof (e.g., a pharmaceutically acceptable salt or prodrug thereof).

In another aspect, this invention relates to compounds having formula (V):

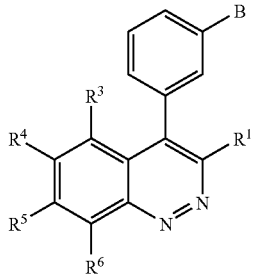

in which $R^1$, $R^3$, $R^4$, $R^5$, and $R^6$ can be as defined elsewhere, and B is:

(i) halo; $NO_2$; $NR^gR^h$; hydroxy; $C_1$-$C_{20}$ alkoxy optionally substituted with from 1-10 $R^a$; $C_6$-$C_{18}$ aryloxy or heteroaryloxy including 5-16 atoms, each of which is optionally substituted with from 1-10 $R^{b'}$; $C_7$-$C_{20}$ aralkoxy or heteroaralkoxy including 6-20 atoms, each of which is substituted with from 1-10 $R^c$; $C_6$-$C_{18}$ thioaryloxy or thioheteroaryloxy including 5-16 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_{20}$ alkyl or $C_1$-$C_{20}$ haloalkyl, each of which is optionally substituted with from 1-10 $R^a$; or (iii) $C_6$-$C_{18}$ aryl or heteroaryl including 5-16 atoms, each of which is optionally substituted with from 1-10 $R^{b'}$;

(iv) $C_7$-$C_{20}$ aralkyl or heteroaralkyl including 6-20 atoms, each of which is optionally substituted with from 1-10 $R^c$; or (v) hydrogen;

in which $R^{b'}$ and $R^c$ can be as defined elsewhere; a compound of formula (V) can be a salt or prodrug thereof (e.g., a pharmaceutically acceptable salt or prodrug).

Embodiments can include one more of the following features.

$R^1$ can be:

(ii) $C_1$-$C_{20}$ alkyl or $C_1$-$C_{20}$ haloalkyl, each of which is optionally substituted with from 1-10 $R^a$; or (iii) $C_6$-$C_{18}$ aryl or heteroaryl including 5-16 atoms, each of which is optionally substituted with from 1-10 $R^b$; or (iv) $C_7$-$C_{20}$ aralkyl or heteroaralkyl including 6-20 atoms, each of which is optionally substituted with from 1-10 $R^c$; or (viii) —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$).

$R^1$ can be:

(ii) $C_1$-$C_{10}$ alkyl or $C_1$-$C_{10}$ haloalkyl, each of which is optionally substituted with from 1-5 $R^a$; or (iii) $C_6$-$C_{10}$ aryl or heteroaryl including 5-10 atoms, each of which is optionally substituted with from 1-5 $R^b$; or (iv) $C_7$-$C_{16}$ aralkyl or heteroaralkyl including 6-16 atoms, each of which is optionally substituted with from 1-5 $R^c$; or (viii) —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$).

$R^1$ can be:

(ii) $C_1$-$C_{20}$ alkyl optionally substituted with from 1-10 $R^a$; or (iii) $C_6$-$C_{18}$ aryl optionally substituted with from 1-10 $R^b$; or (iv) $C_7$-$C_{20}$ aralkyl optionally substituted with from 1-10 $R^c$; or (viii) —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$).

$R^1$ can be:

(ii) $C_1$-$C_{10}$ alkyl optionally substituted with from 1-5 $R^a$; or (iii) $C_6$-$C_{10}$ aryl optionally substituted with from 1-5 $R^b$; or (iv) $C_7$-$C_{16}$ aralkyl optionally substituted with from 1-5 $R^c$; or (viii) —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$).

$R^1$ can be $C_1$-$C_{20}$ alkyl optionally substituted with from 1-10 $R^a$ (e.g., $C_1$-$C_{10}$ alkyl optionally substituted with from 1-5 $R^a$; $C_1$-$C_6$ alkyl optionally substituted with from 1-3 $R^a$; or $C_1$-$C_3$ alkyl optionally substituted with from 1-2 $R^a$). $R^1$ can be $CH_3$.

$R^1$ can be $C_6$-$C_{18}$ aryl, optionally substituted with from 1-10 $R^b$ (e.g., $C_6$-$C_{10}$ aryl, optionally substituted with from 1-5 $R^b$; phenyl optionally substituted with 1, 2, 3, 4, or 5 $R^b$). $R^b$ at each occurrence can be, independently, $C_1$-$C_6$ alkyl, $C_1$-$C_6$ haloalkyl, $C_1$-$C_6$ alkoxy, $C_1$-$C_6$ haloalkoxy, halo, $NO_2$, $NR^gR^h$, or cyano. $R^b$ at each occurrence can be, independently, $C_1$-$C_3$ alkyl, $C_1$-$C_3$ haloalkyl, $C_1$-$C_3$ alkoxy, $C_1$-$C_3$ haloalkoxy, halo, $NO_2$, $NH_2$, or cyano). The $C_1$-$C_3$ haloalkyl can include 1, 2, 3, 4, or 5 halogens or can be $C_1$-$C_3$ perhaloalkyl, in which the halogen can be, for example, fluoro. $R^1$ can be phenyl.

$R^1$ can be $C_7$-$C_{20}$ aralkyl optionally substituted with from 1-10 $R^c$ (e.g., $C_7$-$C_{12}$ aralkyl optionally substituted with from 1-5 $R^c$). $R^1$ can be benzyl.

$R^1$ can be hydrogen.

$R^1$ can be —C(O)$R^i$. For example, $R^i$ can be $C_6$-$C_{18}$ aryl or heteroaryl including 5-16 atoms, each of which is optionally substituted with from 1-10 $R^b$. $R^i$ can be phenyl or phenyl substituted with 1, 2, 3, 4, or 5 $R^b$. $R^b$ at each occurrence can be, independently, $C_1$-$C_6$ alkyl, $C_1$-$C_6$ haloalkyl, $C_1$-$C_6$ alkoxy, $C_1$-$C_6$ haloalkoxy, halo, $NO_2$, $NR^gR^h$, or cyano.

$R^2$ can be:

(i) $C_6$-$C_{18}$ aryl optionally substituted with from 1-10 $R^b$; or (ii) $C_7$-$C_{20}$ aralkyl optionally substituted with from 1-10 $R^c$; or (iii) $C_3$-$C_{20}$ cycloalkyl or $C_3$-$C_{20}$ halocycloalkyl, optionally substituted with from 1-10 $R^e$; or (iv) $C_3$-$C_{20}$ cycloalkenyl optionally substituted with from 1-10 $R^f$.

$R^2$ can be $C_6$-$C_{18}$ aryl or heteroaryl including 5-16 atoms, each of which is optionally substituted with from 1-10 $R^b$.

$R^2$ can be $C_6$-$C_{18}$ aryl optionally substituted with from 1-10 $R^b$ (e.g., $C_6$-$C_{10}$ aryl, optionally substituted with from 1-5 $R^b$; phenyl optionally substituted with from 1-5 $R^b$; phenyl optionally substituted with from 1-3 $R^b$). $R^2$ can be phenyl. $R^2$ can be phenyl substituted with 1, 2, 3, 4, or 5 $R^b$. $R^2$ can be phenyl substituted with 1, 2, 3, or 4 $R^b$. $R^2$ can be phenyl substituted with 1, 2, or 3 $R^b$. $R^2$ can be phenyl substituted with from 1 or 2 $R^b$. $R^2$ can be phenyl substituted with 1 $R^b$.

In some embodiments, when $R^2$ is $C_6$-$C_{18}$ aryl or heteroaryl including 5-16 atoms, each of which is optionally substituted with from 1-10 $R^b$; or $C_6$-$C_{18}$ aryl optionally substituted with from 1-10 $R^b$; or $C_6$-$C_{10}$ aryl, optionally substituted with from 1-5 $R^b$; or $R^2$ is phenyl substituted with 1, 2, 3, 4, or 5 $R^b$; or $R^2$ is phenyl substituted with 1, 2, 3, or 4 $R^b$; or $R^2$ is phenyl substituted with 1, 2, or 3 $R^b$; or $R^2$ is phenyl substituted with 1 or 2 $R^b$; or $R^2$ is phenyl substituted with 1 $R^b$, then $R^b$ at each occurrence can be, independently:

(i) halo; $NO_2$; $NR^gR^h$; hydroxy; $C_1$-$C_{20}$ alkoxy or $C_1$-$C_{20}$ haloalkoxy, each of which is optionally substituted with from 1-10 $R^a$; $C_6$-$C_{18}$ aryloxy or heteroaryloxy including 5-16 atoms, each of which is optionally substituted with from 1-10 $R^{b'}$; $C_7$-$C_{20}$ aralkoxy or heteroaralkoxy including 6-20 atoms, each of which is optionally substituted with from 1-10 $R^c$; $C_3$-$C_{16}$ cycloalkoxy or $C_3$-$C_{16}$ halocycloalkoxy, each of which is optionally substituted with from 1-10 $R^e$; $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; mercapto; $C_1$-$C_{20}$ thioalkoxy or $C_1$-$C_{20}$ thiohaloalkoxy, each of which is optionally substituted with from 1-10 $R^a$; $C_6$-$C_{18}$ thioaryloxy or thioheteroaryloxy including 5-16 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; $C_3$-$C_{20}$ thiocycloalkoxy or $C_3$-$C_{20}$ thiohalocycloalkoxy, each of which is optionally substituted with from 1-10 $R^e$; $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; cyano; —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)(O$R^g$)(O$R^h$);

(ii) $C_1$-$C_{20}$ alkyl or $C_1$-$C_{20}$ haloalkyl, each of which is optionally substituted with from 1-10 $R^a$; or (vi) $C_7$-$C_{20}$ aralkyl or heteroaralkyl including 6-20 atoms, each of which is optionally substituted with from 1-10 $R^c$; or (vii) $C_6$-$C_{18}$ aryl or heteroaryl including 5-16 atoms, each of which is optionally substituted with from 1-10 $R^{b'}$; or $R^b$ at each occurrence can be, independently:

(i) halo; $NO_2$; $NR^gR^h$; hydroxy; $C_1$-$C_{20}$ alkoxy optionally substituted with from 1-10 $R^a$; $C_6$-$C_{18}$ aryloxy or heteroaryloxy including 5-16 atoms, each of which is optionally substituted with from 1-10 $R^{b'}$; $C_7$-$C_{20}$ aralkoxy or heteroaralkoxy including 6-20 atoms, each of which is substituted with from 1-10 $R^c$; $C_6$-$C_{18}$ thioaryloxy or thioheteroaryloxy including 5-16 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_{20}$ alkyl or $C_1$-$C_{20}$ haloalkyl, each of which is optionally substituted with from 1-10 $R^a$; or (vi) $C_7$-$C_{20}$ aralkyl or heteroaralkyl including 6-20 atoms, each of which is optionally substituted with from 1-10 $R^c$; or (vii) $C_6$-$C_{18}$ aryl or heteroaryl including 5-16 atoms, each of which is optionally substituted with from 1-10 $R^{b'}$; or $R^b$ at each occurrence can be, independently:

(i) halo; $NO_2$; $NR^gR^h$; hydroxy; $C_1$-$C_{10}$ alkoxy optionally substituted with from 1-5 $R^a$; $C_6$-$C_{14}$ aryloxy or heteroaryloxy including 5-14 atoms, each of which is optionally substituted with from 1-10 $R^{b'}$; $C_7$-$C_{20}$ aralkoxy or heteroaralkoxy including 6-20 atoms, each of which is substituted with from 1-10 $R^c$; $C_6$-$C_{14}$ thioaryloxy or thioheteroaryloxy including 5-14 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_{10}$ alkyl or $C_1$-$C_{10}$ haloalkyl, each of which is optionally substituted with from 1-5 $R^a$; or (vi) $C_7$-$C_{16}$ aralkyl or heteroaralkyl including 6-16 atoms, each of which is optionally substituted with from 1-10 $R^c$; or (vii) $C_6$-$C_{14}$ aryl or heteroaryl including 5-14 atoms, each of which is optionally substituted with from 1-10 $R^{b'}$; or $R^b$ at each occurrence can be, independently:

(i) halo; $NO_2$; $NR^gR^h$; hydroxy; $C_1$-$C_6$ alkoxy optionally substituted with from 1-3 $R^a$; $C_6$-$C_{10}$ aryloxy or heteroaryloxy including 5-10 atoms, each of which is optionally substituted with from 1-5 $R^{b'}$; $C_7$-$C_{16}$ aralkoxy or heteroaralkoxy including 6-16 atoms, each of which is substituted with from 1-5 $R^c$; $C_6$-$C_{10}$ thioaryloxy or thioheteroaryloxy including 5-14 atoms, each of which is optionally substituted with from 1-5 $R^{b'}$; $C_7$-$C_{16}$ thioaralkoxy or thioheteroaralkoxy including 6-16 atoms, each of which is optionally substituted with from 1-5 $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_6$ alkyl or $C_1$-$C_6$ haloalkyl, each of which is optionally substituted with from 1-3 $R^a$; or (vi) $C_7$-$C_{12}$ aralkyl or heteroaralkyl including 6-12 atoms, each of which is optionally substituted with from 1-5 $R^c$; or (vii) $C_6$-$C_{10}$ aryl or heteroaryl including 5-10 atoms, each of which is optionally substituted with from 1-5 $R^{b'}$; or $R^b$ at each occurrence can be, independently:

(i) halo; $NO_2$; $NR^gR^h$; hydroxy; $C_1$-$C_3$ alkoxy optionally substituted with from 1-2 $R^a$; $C_6$-aryloxy or heteroaryloxy including 5 or 6 atoms, each of which is optionally substituted with from 1-5 $R^{b'}$; $C_7$-$C_{12}$ aralkoxy or heteroaralkoxy including 6-12 atoms, each of which is substituted with from 1-5 $R^c$; $C_6$-thioaryloxy or thioheteroaryloxy including 5 or 6 atoms, each of which is optionally substituted with from 1-5 $R^{b'}$; $C_7$-$C_{12}$ thioaralkoxy or thioheteroaralkoxy including 6-12 atoms, each of which is optionally substituted with from 1-5 $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_3$ alkyl or $C_1$-$C_3$ haloalkyl, each of which is optionally substituted with from 1-2 $R^a$; or (vi) $C_7$-$C_{10}$ aralkyl or heteroaralkyl including 6-20 atoms, each of which is optionally substituted with from 1-5 $R^c$; or (vii) phenyl or heteroaryl including 5 or 6 atoms, each of which is optionally substituted with from 1-5 $R^{b'}$.

$R^2$ can be:

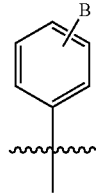 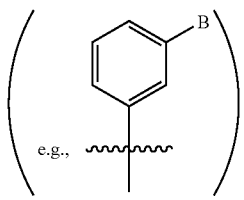

wherein B is:

(i) halo; $NO_2$; $NR^gR^h$; hydroxy; $C_1$-$C_{20}$ alkoxy optionally substituted with from 1-10 $R^a$; $C_6$-$C_{18}$ aryloxy or heteroaryloxy including 5-16 atoms, each of which is optionally substituted with from 1-10 $R^{b'}$; $C_7$-$C_{20}$ aralkoxy or heteroaralkoxy including 6-20 atoms, each of which is substituted with from 1-10 $R^c$; $C_6$-$C_{18}$ thioaryloxy or thioheteroaryloxy including 5-16 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) $C_1$-$C_{20}$ alkyl or $C_1$-$C_{20}$ haloalkyl, each of which is optionally substituted with from 1-10 $R^a$; or (iii) $C_6$-$C_{18}$ aryl or heteroaryl including 5-16 atoms, each of which is optionally substituted with from 1-10 $R^{b'}$; or (iv) $C_7$-$C_{20}$ aralkyl or heteroaralkyl including 6-20 atoms, each of which is optionally substituted with from 1-10 $R^c$; or (v) hydrogen; B can also be other than hydrogen, i.e., (i), (ii), (iii), or (iv).

B can be hydrogen.

B can be:

(i) halo; $NO_2$; $NR^gR^h$; hydroxy; $C_1$-$C_{10}$ alkoxy optionally substituted with from 1-5 $R^a$; $C_6$-$C_{14}$ aryloxy or heteroaryloxy including 5-14 atoms, each of which is optionally substituted with from 1-10 $R^{b'}$; $C_7$-$C_{20}$ aralkoxy or heteroaralkoxy including 6-20 atoms, each of which is substituted with from 1-10 $R^c$; $C_6$-$C_{14}$ thioaryloxy or thioheteroaryloxy including 5-14 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) $C_1$-$C_{10}$ alkyl or $C_1$-$C_{10}$ haloalkyl, each of which is optionally substituted with from 1-5 $R^a$; or (iii) $C_7$-$C_{16}$ aralkyl or heteroaralkyl including 6-20 atoms, each of which is optionally substituted with from 1-10 $R^c$; or (iv) $C_6$-$C_{14}$ aryl or heteroaryl including 5-14 atoms, each of which is optionally substituted with from 1-10 $R^{b'}$.

B can be:

(i) halo; $NO_2$; $NR^gR^h$; hydroxy; $C_1$-$C_6$ alkoxy optionally substituted with from 1-3 $R^a$; $C_6$-$C_{10}$ aryloxy or heteroaryloxy including 5-10 atoms, each of which is optionally substituted with from 1-5 $R^{b'}$; $C_7$-$C_{16}$ aralkoxy or heteroaralkoxy including 6-16 atoms, each of which is substituted with from 1-5 $R^c$; $C_6$-$C_{10}$ thioaryloxy or thioheteroaryloxy including 5-14 atoms, each of which is optionally substituted with from 1-5 $R^{b'}$; $C_7$-$C_{16}$ thioaralkoxy or thioheteroaralkoxy including 6-16 atoms, each of which is optionally substituted with from 1-5 $R^c$; cyano; —C(O)NR$^g$R$^h$; —C(O)R$^i$; —NR$^j$C(O)R$^i$; —NR$^j$C(O)NR$^g$R$^h$ or —S(O)$_n$R$^k$; or (ii) $C_1$-$C_6$ alkyl or $C_1$-$C_6$ haloalkyl, each of which is optionally substituted with from 1-3 $R^a$; or (iii) $C_7$-$C_{12}$ aralkyl or heteroaralkyl including 6-20 atoms, each of which is optionally substituted with from 1-5 $R^c$; or (iv) $C_6$-$C_{10}$ aryl or heteroaryl including 5-10 atoms, each of which is optionally substituted with from 1-5 $R^{b'}$.

B can be:

(i) halo; $NO_2$; $NR^gR^h$; hydroxy; $C_1$-$C_3$ alkoxy optionally substituted with from 1-2 $R^a$; $C_6$-aryloxy or heteroaryloxy including 5 or 6 atoms, each of which is optionally substituted with from 1-5 $R^{b'}$; $C_7$-$C_{12}$ aralkoxy or heteroaralkoxy including 6-12 atoms, each of which is substituted with from 1-5 $R^c$; $C_6$-thioaryloxy or thioheteroaryloxy including 5 or 6 atoms, each of which is optionally substituted with from 1-5 $R^{b'}$; $C_7$-$C_{12}$ thioaralkoxy or thioheteroaralkoxy including 6-12 atoms, each of which is optionally substituted with from 1-5 $R^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) $C_1$-$C_3$ alkyl or $C_1$-$C_3$ haloalkyl, each of which is optionally substituted with from 1-2 $R^a$; or (iii) $C_7$-$C_{10}$ aralkyl or heteroaralkyl including 6-20 atoms, each of which is optionally substituted with from 1-5 $R^c$; or (iv) $C_6$-aryl or heteroaryl including 5 or 6 atoms, each of which is optionally substituted with from 1-5 $R^{b'}$.

B can be hydroxy. B can be $NH_2$. B can be halo (e.g., fluoro or chloro). B can be $C_1$-$C_6$ alkoxy (e.g., $OCH_3$). B can be $C_1$-$C_4$ haloalkyl (e.g., $CF_3$). B can be —C(O)R$^i$ (e.g., formyl).

B can be $C_1$-$C_6$ alkyl, optionally substituted with 1 $R^a$ (e.g., B can be a substituted $CH_3$ group). $R^a$ can be $NR^gR^h$. For example, one of $R^g$ and $R^h$ can be hydrogen, and the other can be $C_6$-$C_{18}$ aryl or heteroaryl including 5-16 atoms, each of which can be optionally substituted with from 1-10 $R^b$. In some embodiments, one of $R^g$ and $R^h$ can be hydrogen, and the other can be a phenyl or napthyl group, each of which is optionally substituted with from 1-5 (e.g., 1-3) $R^b$ (e.g., $C_1$-$C_4$ alkyl (e.g., $CH_3$) optionally substituted with 1 $R^a$ (e.g., COOH)). For example, one of $R^g$ and $R^h$ can be hydrogen, and the other can be a phenyl ring in which an ortho position, a meta position, and the para position are each substituted with a combination of $CH_3$ and $CH_2C(O)OH$.

B can be —NR$^j$C(O)NR$^g$R$^h$. $R^j$ can be hydrogen or $C_1$-$C_6$ alkyl (e.g., $C_1$-$C_3$ alkyl). $R^j$ can be hydrogen. One of $R^g$ and $R^h$ can be hydrogen, and the other can be $C_7$-$C_{20}$ aralkyl or heteroaralkyl including 6-20 atoms, each of which is optionally substituted with from 1-10 $R^c$; or $C_6$-$C_{18}$ aryl or heteroaryl including 5-16 atoms, each of which is optionally substituted with from 1-10 $R^b$.

For example, B can be:

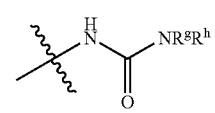

One of $R^g$ and $R^h$ can be hydrogen, and the other can be $C_7$-$C_{20}$ aralkyl optionally substituted with from 1-10 $R^c$; or $C_6$-$C_{18}$ aryl optionally substituted with from 1-10 $R^b$. One of $R^g$ and $R^h$ can be hydrogen, and the other can be $C_6$-$C_{18}$ aryl optionally substituted with from 1-10 $R^b$. One of $R^g$ and $R^h$ can be hydrogen, and the other can be $C_6$-$C_{10}$ aryl optionally substituted with from 1-5 $R^b$. One of $R^g$ and $R^h$ can be hydrogen, and the other can be phenyl optionally substituted with from 1, 2, 3, 4, or 5 $R^b$. One of $R^g$ and $R^h$ can be hydrogen, and the other can be phenyl. One of $R^g$ and $R^h$ is hydrogen, and the other can be phenyl substituted with from 1, 2, 3, or 4 $R^b$. $R^b$ at each occurrence can be, independently, halo; $NO_2$; hydroxy; $C_1$-$C_{10}$ alkoxy; cyano; —C(O)R$^i$; $C_1$-$C_{10}$ alkyl; or $C_1$-$C_{10}$ haloalkyl (e.g., halo, $NO_2$, hydroxyl, $C_1$-$C_6$ alkoxy, cyano, —C(O)R$^i$, $C_1$-$C_6$ alkyl, or $C_1$-$C_6$ haloalkyl; e.g., halo, $NO_2$, hydroxy; $C_1$-$C_3$ alkoxy, cyano, —C(O)R$^i$, $C_1$-$C_3$ alkyl, or $C_1$-$C_3$ haloalkyl). The $C_1$-$C_3$ haloalkyl can include 1, 2, 3, 4, or 5 halogens or can be $C_1$-$C_3$ perhaloalkyl, in which the halogen can be, for example, fluoro).

B can be:

(i-B) $NR^gR^h$, wherein one of $R^g$ and $R^h$ is hydrogen, and the other is $C_7$-$C_{20}$ aralkyl or heteroaralkyl including 6-20 atoms, each of which is optionally substituted with from 1-10 $R^c$; or $C_6$-$C_{18}$ aryl or heteroaryl including 5-16 atoms, each of which is optionally substituted with from 1-10 $R^b$; or (ii-B) $C_6$-$C_{18}$ aryloxy or heteroaryloxy including 5-16 atoms, each of which is optionally substituted with from 1-10 $R^{b'}$; or $C_7$-$C_{20}$ aralkoxy or heteroaralkoxy including 6-20 atoms, each of which is optionally substituted with from 1-10 $R^c$; or (iii-B) $C_6$-$C_{18}$ thioaryloxy or thioheteroaryloxy including 5-16 atoms, each of which is optionally substituted with from 1-10 $R^{b'}$; or $C_7$-$C_{20}$ thioaralkoxy or thioheteroaralkoxy including 6-20 atoms, each of which is optionally substituted with from 1-10 $R^c$; or (vi-B) $C_6$-$C_{18}$ aryl or heteroaryl including 5-16 atoms, each of which is optionally substituted with from 1-10 $R^{b'}$; or $C_7$-$C_{20}$ aralkyl or heteroaralkyl including 6-20 atoms, each of which is optionally substituted with from 1-10 $R^c$.

B can be:

(i-B') $NR^gR^h$, wherein one of $R^g$ and $R^h$ is hydrogen, and the other is $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 14, 1-3, 1-2, 1) $R^c$;

(ii-B') $C_7$-$C_{20}$ (e.g., $C_7$-$C_{16}$, $C_7$-$C_{12}$, $C_7$-$C_{10}$) aralkoxy or heteroaralkoxy including 6-20 (e.g., 6-14, 6-12, 6-10) atoms, each of which is optionally substituted with from 1-10 (e.g., 1-5, 1-4, 1-3, 1-2, 1) $R^c$; or (iii-B') $C_7$-$C_{20}$ (e.g., $C_7$-$C_{16}$, $C_7$-$C_{12}$, $C_7$-$C_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) $R^c$; or (iv-B') $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)O$R^i$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)O$R^i$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_6$ alkoxy; $C_1$-$C_6$ haloalkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_6$ alkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_3$ alkoxy; $C_1$-$C_3$ haloalkoxy; cyano; —C(O)$R^i$; $C_1$-$C_4$ alkyl or $C_1$-$C_4$ haloalkyl, each of which is optionally substituted with from 1-2 $R^a$; or —C(O)O$R^i$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_3$ alkoxy; cyano; —C(O)$R^i$; $C_1$-$C_4$ alkyl or $C_1$-$C_4$ haloalkyl, each of which is optionally substituted with from 1-2 $R^a$; or —C(O)O$R^i$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_3$ alkoxy; cyano; —C(O)$R^i$; $C_1$-$C_4$ alkyl; $C_1$-$C_4$ haloalkyl; $C_1$-$C_4$ alkyl substituted with from 1-2 $R^a$; —C(O)OH; or —C(O)OCH$_3$.

In some embodiments, when B is (i-B), (ii-B), (iii-B), (iv-B), (i-B'), (ii-B'), (iii-B'), or (iv-B'), then $R^b$, $R^{b'}$ and $R^c$ at each occurrence can each be, independently, halo; $NO_2$; hydroxy; $C_1$-$C_3$ alkoxy; cyano; —C(O)$R^i$; $C_1$-$C_4$ alkyl; $C_1$-$C_4$ haloalkyl; $C_1$-$C_4$ alkyl substituted with from 1-2 $R^a$; —C(O)OH; or —C(O)OCH$_3$.

In some embodiments, when B is (i-B), (ii-B), (iii-B), (iv-B), (i-B'), (ii-B'), (iii-B'), or (iv-B'), $R^a$ can be —C(O)OH or —C(O)OCH$_3$; and/or $C_1$-$C_4$ haloalkyl can be $C_1$-$C_4$ perfluoroalkyl.

B can be:

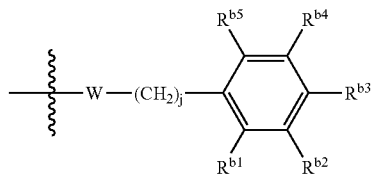

wherein:

W can be $NR^j$, O, S, or is absent;

j can be 0, 1, 2, 3, 4, or 5; and each of $R^{b1}$, $R^{b2}$, $R^{b3}$, $R^{b4}$, and $R^{b5}$ is, independently, hydrogen, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)O$R^i$.

Each of $R^{b1}$, $R^{b2}$, $R^{b3}$, $R^{b4}$, and $R^{b5}$ can be, independently, hydrogen, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)O$R^i$.

W can be $NR^j$, O, or S. $R^j$ can be hydrogen or $C_1$-$C_6$ alkyl (e.g., $C_1$-$C_3$ alkyl). $R^j$ can be hydrogen. j can be 0 or 1 (e.g., 1).

$R^{b1}$, $R^{b2}$, $R^{b3}$, $R^{b4}$, and $R^{b5}$ can each be, independently, hydrogen; halo; $NO_2$; hydroxy; $C_1$-$C_6$ alkoxy; $C_1$-$C_6$ haloalkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$.

$R^{b1}$, $R^{b2}$, $R^{b3}$, $R^{b4}$, and $R^{b5}$ can each be, independently, hydrogen; halo; $NO_2$; hydroxy; $C_1$-$C_6$ alkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$.

$R^{b1}$, $R^{b2}$, $R^{b3}$, $R^{b4}$, and $R^{b5}$ can each be, independently, hydrogen; halo; $NO_2$; hydroxy; $C_1$-$C_3$ alkoxy; $C_1$-$C_3$ haloalkoxy; cyano; —C(O)$R^i$; $C_1$-$C_4$ alkyl or $C_1$-$C_4$ haloalkyl, each of which is optionally substituted with from 1-2 $R^a$; or —C(O)O$R^i$.

$R^{b1}$, $R^{b2}$, $R^{b3}$, $R^{b4}$, and $R^{b5}$ can each be, independently, hydrogen; halo; $NO_2$; hydroxy; $C_1$-$C_3$ alkoxy; cyano; —C(O)$R^i$; $C_1$-$C_4$ alkyl or $C_1$-$C_4$ haloalkyl, each of which is optionally substituted with from 1-2 $R^a$; or —C(O)O$R^i$.

$R^{b1}$, $R^{b2}$, $R^{b3}$, $R^{b4}$, and $R^{b5}$ can each be, independently, hydrogen; F; Cl; Br; OH; OCH$_3$; OCF$_3$; —C(O)(morpholino); CH$_3$; CH$_3$ substituted with from 1-2 $R^a$ (e.g., —C(O)OH or —C(O)OCH$_3$); CF$_3$; —C(O)OH; or —C(O)OCH$_3$.

$R^{b1}$, $R^{b2}$, $R^{b3}$, $R^{b4}$, and $R^{b5}$ can each be, independently, hydrogen; F; Cl; Br; OH; OCH$_3$; —C(O)(morpholino); CH$_3$; CH$_3$ substituted with from 1-2 $R^a$ (e.g., —C(O)OH or —C(O)OCH$_3$); CF$_3$; —C(O)OH; or —C(O)OCH$_3$.

One of $R^{b1}$, $R^{b2}$, $R^{b3}$, $R^{b4}$ or $R^{b5}$ (e.g., $R^{b3}$) can be halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and the other four can be hydrogen.

One of $R^{b1}$, $R^{b2}$, $R^{b3}$, $R^{b4}$, or $R^{b5}$ (e.g., $R^{b3}$) can be halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and the other four can be hydrogen. One of $R^{b1}$, $R^{b2}$, $R^{b3}$, $R^{b4}$, or $R^{b5}$ can be $C_1$-$C_{10}$ haloalkoxy (e.g., $OCF_3$), and the other four can be hydrogen.

$R^{b3}$ can be $C_1$-$C_4$ alkyl substituted with from 1 $R^a$. $R^a$ can be C(O)$OR^i$. $R^i$ can be hydrogen or $C_1$-$C_4$ alkyl (e.g., $CH_3$). $R^{b3}$ can be —$CH_2$C(O)OH, —$CH_2$C(O)$OCH_3$, —C($CH_3$)$_2$C(O)OH, or —C($CH_3$)$_2$C(O)$OCH_3$. $R^{b3}$ can be —C(O)$OR^i$ (e.g., COOH).

$R^{b1}$ can be $C_1$-$C_6$ haloalkoxy (e.g., $OCF_3$). $R^{b1}$ can be halo (e.g., chloro).

$R^{b2}$ can be $C_1$-$C_4$ haloalkyl (e.g., $CF_3$); or —C(O)$OR^i$ (e.g., COOH); or —C(O)$R^i$ (e.g., —C(O)(morpholino)).

Two of $R^{b1}$, $R^{b2}$, $R^{b3}$, $R^{b4}$, or $R^{b5}$ can each be, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and the other three are hydrogen.

Two of $R^{b1}$, $R^{b2}$, $R^{b3}$, $R^{b4}$, or $R^{b5}$ can each be, independently, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and the other three are hydrogen. One or both of $R^{b1}$, $R^{b2}$, $R^{b3}$, $R^{b4}$, or $R^{b5}$ can be $C_1$-$C_{10}$ haloalkoxy (e.g., $OCF_3$), and the others can be hydrogen.

$R^{b1}$ and $R^{b4}$ can each be, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b2}$, $R^{b3}$, and $R^{b5}$ is hydrogen.

$R^{b1}$ and $R^{b4}$ can each be, independently, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b2}$, $R^{b3}$, and $R^{b5}$ is hydrogen.

$R^{b1}$ and $R^{b4}$ can each be, independently, halo; $C_1$-$C_6$ alkyl; $C_1$-$C_4$ haloalkyl; or $C_1$-$C_6$ alkoxy; and each of $R^{b2}$, $R^{b3}$, and $R^{b5}$ is hydrogen.

$R^{b1}$ and $R^{b4}$ can both be $C_1$-$C_4$ alkyl (e.g., $CH_3$), and each of $R^{b2}$, $R^{b3}$, and $R^{b5}$ can be hydrogen.

$R^{b1}$ and $R^{b4}$ can both be $C_1$-$C_4$ haloalkyl (e.g., $CF_3$), and each of $R^{b2}$, $R^{b3}$, and $R^{b5}$ can be hydrogen.

$R^{b1}$ can be $C_1$-$C_4$ haloalkyl (e.g., $CF_3$), $R^{b4}$ can be halo (e.g., fluoro or chloro), and each of $R^{b2}$, $R^{b3}$, and $R^{b5}$ can be hydrogen.

One of $R^{b1}$ and $R^{b4}$ can be halo (e.g., bromo), and the other can be $C_1$-$C_6$ alkoxy (e.g., $OCH_3$); and each of $R^{b2}$, $R^{b3}$, and $R^{b5}$ can be hydrogen.

$R^{b1}$ can be halo (e.g, fluoro or chloro); $R^{b4}$ can be $C_1$-$C_4$ haloalkyl (e.g., $CF_3$) or halo (e.g., fluoro, chloro, or bromo); and each of $R^{b2}$, $R^{b3}$, and $R^{b5}$ can be hydrogen.

$R^{b1}$ and $R^{b2}$ can each be, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b3}$, $R^{b4}$, and $R^{b5}$ is hydrogen.

$R^{b1}$ and $R^{b2}$ can each be, independently, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b3}$, $R^{b4}$, and $R^{b5}$ is hydrogen.

$R^{b1}$ and $R^{b2}$ can both be $C_1$-$C_4$ alkyl (e.g., $CH_3$), and each of $R^{b3}$, $R^{b4}$, and $R^{b5}$ can be hydrogen.

$R^{b1}$ can be halo (e.g., fluoro or chloro), $R^{b2}$ can be $C_1$-$C_4$ haloalkyl (e.g., $CF_3$), and each of $R^{b3}$, $R^{b4}$, and $R^{b5}$ can be hydrogen.

$R^{b2}$ and $R^{b3}$ can each be, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b1}$, $R^{b2}$, and $R^{b5}$ is hydrogen.

$R^{b2}$ and $R^{b3}$ can each be, independently, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b1}$, $R^{b2}$, and $R^{b5}$ is hydrogen.

$R^{b2}$ and $R^{b3}$ can each be, independently, halo; $C_1$-$C_6$ alkoxy; or —C(O)$OR^i$; and each of $R^{b1}$, $R^{b4}$, and $R^{b5}$ is hydrogen.

$R^{b2}$ and $R^{b3}$ can both be halo (e.g., chloro), and each of $R^{b1}$, $R^{b2}$, and $R^{b5}$ can be hydrogen.

$R^{b2}$ and $R^{b3}$ can each be, independently, $C_1$-$C_6$ alkoxy (e.g., $OCH_3$); or —C(O)$OR^i$ (e.g., COOH); and each of $R^{b1}$, $R^{b4}$, and $R^{b5}$ can be hydrogen.

$R^{b1}$ and $R^{b5}$ can each be, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b2}$, $R^{b3}$, and $R^{b4}$ is hydrogen. For example, $R^{b1}$ and $R^{b5}$ can both be halo (e.g., chloro), and each of $R^{b2}$, $R^{b3}$, and $R^{b4}$ can be hydrogen.

$R^{b1}$ and $R^{b3}$ can each be, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b2}$, $R^{b4}$, and $R^{b5}$ is hydrogen. For example, $R^{b1}$ can be halo (e.g., chloro), $R^{b3}$ can be —C(O)$OR^i$ (e.g., COOH), and each of $R^{b2}$, $R^{b4}$, and $R^{b5}$ can be hydrogen.

Each of $R^{b2}$, $R^{b3}$, $R^{b4}$, and $R^{b5}$ can be hydrogen.

Each of $R^{b1}$, $R^{b2}$, $R^{b3}$, $R^{b4}$, and $R^{b1}$ can be other than hydrogen.

When B is as described in (i-B), (ii-B), (iii-B), (iv-B), (i-B'), (ii-B'), (iii-B'), (iv-B')), B can also be W—($CH_2$)$_j$-(bicyclic or tricyclic aryl) or W—($CH_2$)$_j$-(heteroaryl), in which W and j can be as described elsewhere.

B can be —NH—$CH_2$-naphthyl (e.g., the methylene group can be attached to the 1 or 2 position of the naphthyl ring, and the naphthyl ring can optionally be substituted in one or more positions, e.g., with 1-5, 1-4, 1-3, 1-2, or 1 $R^c$).

In certain embodiments, B can be —NH—$CH_2$-indolyl or —O—$CH_2$-indolyl (e.g., the methylene group can be attached to the 2 or 7 position of the indole ring, and the indole ring can be optionally substituted in one or more positions, e.g., with 1-5, 1-4, 1-3, 1-2, or 1 $R^c$, e.g., at the 1-position with $CH_3$ and/or at the 5-position with halo (e.g., fluoro) and/or at the 3-position with COOR$^i$ (e.g., COOH).

In certain embodiments, B can be —NH—$CH_2$-benzothienyl (e.g., the methylene group can be attached to the 2 or 3 position of the benzothienyl ring, and the benzothienyl ring can be optionally substituted in one or more positions, e.g., with 1-5, 1-4, 1-3, 1-2, or 1 $R^c$, e.g., at the 3-position with $C_1$-$C_6$ alkyl (e.g., $CH_3$) or at the 4-position with $C_1$-$C_4$ haloalkyl (e.g., $CF_3$)).

B can be —C(O)$NR^gR^h$; —C(O)$R^i$; —$NR^jC(O)R^i$; —$NR^jC(O)NR^gR^h$; or —S(O)$_nR^k$. $R^j$ can be hydrogen or $C_1$-$C_6$ alkyl (e.g., $C_1$-$C_3$ alkyl). $R^j$ can be hydrogen. Each of $R^i$ and $R^k$ can be, independently, $C_6$-$C_{18}$ aryl or heteroaryl including 5-16 atoms, each of which is optionally substituted with from 1-10 $R^b$; or $C_7$-$C_{20}$ aralkyl or heteroaralkyl including 6-20 atoms, each of which is optionally substituted with from 1-10 $R^c$. Each of $R^i$ and $R^k$ can be, independently, $C_6$-$C_{18}$ aryl optionally substituted with from 1-10 $R^{b'}$; or $C_7$-$C_{20}$ aralkyl optionally substituted with from 1-10 $R^c$ ($R^{b'}$ and $R^c$ at each occurrence can each be, independently, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)O$R^i$). One of $R^g$ or $R^h$ can be hydrogen, and the other can be $C_6$-$C_{18}$ aryl or heteroaryl including 5-16 atoms, each of which is optionally substituted with from 1-10 $R^{b'}$; or $C_7$-$C_{20}$ aralkyl or heteroaralkyl including 6-20 atoms, each of which is optionally substituted with from 1-10 $R^c$. One of $R^g$ or $R^h$ can be hydrogen, and the other can be $C_6$-$C_{18}$ aryl optionally substituted with from 1-10 $R^{b'}$; or $C_7$-$C_{20}$ aralkyl optionally substituted with from 1-10 $R^c$ ($R^{b'}$ and $R^c$ at each occurrence are each, independently, halo; $NO_2$; hydroxy; $C_1$-$C_{10}$ alkoxy; cyano; —C(O)$R^i$; $C_1$-$C_{10}$ alkyl or $C_1$-$C_{10}$ haloalkyl, each of which is optionally substituted with from 1-5 $R^a$; or —C(O)O$R^i$).

$R^2$ can be ortho or para monosubstituted phenyl (e.g., 2-fluoro, 4-fluorophenyl, 4-trifluoromethylphenyl). $R^2$ can be disubstituted phenyl (e.g., 3,4-dihalophenyl, e.g., 3-chloro-4-fluorophenyl).

Each of $R^3$, $R^4$ and $R^5$ can be, independently, hydrogen or halo. Each of $R^3$, $R^4$ and $R^5$ can be hydrogen.

$R^6$ can be halo or $C_1$-$C_{10}$ alkyl, or $C_1$-$C_{10}$ haloalkyl; $R^6$ can be halo or $C_1$-$C_6$ alkyl, or $C_1$-$C_6$ haloalkyl; $R^6$ can be halo or $C_1$-$C_3$ alkyl, or $C_1$-$C_3$ haloalkyl.

$R^6$ can be $C_1$-$C_{10}$ (e.g., $C_1$-$C_6$ or $C_1$-$C_3$) alkyl. $R^6$ can be $CH_3$.

$R^6$ can be $C_1$-$C_{10}$ (e.g., $C_1$-$C_6$ or $C_1$-$C_3$) haloalkyl. $R^6$ can be $CF_3$.

$R^6$ can be halo (e.g., bromo or chloro, preferably chloro). $R^6$ can be hydrogen.

In a further aspect, this invention relates to compounds having formula VI:

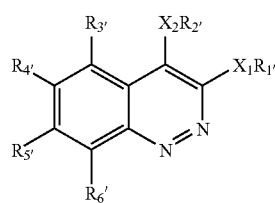

VI in which:

$X_1$ can be a bond, $C_1$ to $C_5$ alkyl, —C(O)—, —C(=CR$_8$R$_9$)—, —O—, —S(O)$_t$—, —NR$_8$—, —CR$_8$R$_9$—, —CHR$_{23}$—, —CR$_8$(OR$_9$)—, —C(OR$_8$)$_2$—, —CR$_8$(OC(O)R$_9$)—, —C=NOR$_9$—, —C(O)NR$_8$—, —CH$_2$O—, —CH$_2$S—, —CH$_2$NR$_8$—, —OCH$_2$—, —SCH$_2$—, —NR$_8$CH$_2$—, or

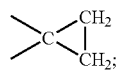

$R_{1'}$ can be H, $C_1$ to $C_6$ alkyl, $C_2$ to $C_6$ alkenyl, $C_2$ to $C_6$ alkynyl, $C_3$ to $C_6$ cycloalkyl, —CH$_2$OH, $C_7$ to $C_{11}$ arylalkyl, phenyl, naphthyl, $C_1$ to $C_3$ perfluoroalkyl, CN, C(O)NH$_2$, CO$_2$R$_{12}$ or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —NO$_2$, —NR$_8$R$_9$, —CN, —OH, and $C_1$ to $C_3$ alkyl substituted with 1 to 5 fluorines, or $R_{1'}$ can be a heterocycle selected from the group consisting of pyridine, thiophene, benzisoxazole, benzothiophene, oxadiazole, pyrrole, pyrazole, and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —NO$_2$, —NR$_8$R$_9$, —CN, and $C_1$ to $C_3$ alkyl substituted with 1 to 5 fluorines;

$X_2$ can be a bond or —CH$_2$—;

$R_{2'}$ can be phenyl, naphthyl, or phenyl or naphthyl substituted independently by one to four groups independently selected from $C_1$ to $C_3$ alkyl, hydroxy, phenyl, acyl, halogen, —NH$_2$, —CN, —NO$_2$, $C_1$ to $C_3$ alkoxy, $C_1$ to $C_3$ perfluoroalkyl, $C_1$ to $C_3$ alkyl substituted with 1 to 5 fluorines, NR$_{14}$R$_{15}$, —C(O)R$_{10}$, —C(O)NR$_{10}$R$_{11}$, —C(O)NR$_{11}$A, —C≡CR$_8$, —CH═CHR$_8$, —W'A, —C≡CA, —CH═CHA, —W'YA, —W'YNR$_{11}$-A, —W'YR$_{10}$, —W'Y(CH$_2$)$_j$A, —W'CHR$_{11}$(CH$_2$)$_j$A, —W'(CH$_2$)$_j$A, —W'(CH$_2$)$_j$R$_{10}$, —CHR$_{11}$W'(CH$_2$)$_j$R$_{10}$, —CHR$_{11}$W'(CH$_2$)$_j$A, —CHR$_{11}$NR$_{12}$YA, —CHR$_{11}$NR$_{12}$YR$_{10}$, pyrrole, —W'(CH$_2$)$_j$A(CH$_2$)$_k$D(CH$_2$)$_p$Z, —W'(CR$_{18}$R$_{19}$)A(CH$_2$)$_k$D(CH$_2$)$_p$Z, —(CH$_2$)$_j$W'A(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, —W'(CH$_2$)$_j$C≡CA(CH$_2$)$_k$D(CH$_2$)$_p$Z, and —W'(CH$_2$)$_j$Z, or $R_{2'}$ can be a heterocycle selected from pyridine, pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$ alkyl, $C_1$ to $C_3$ alkoxy, hydroxy, phenyl, acyl, halogen, —NH$_2$, —CN, —NO$_2$, $C_1$ to $C_3$ perfluoroalkyl, $C_1$ to $C_3$ alkyl substituted with 1 to 5 fluorines, —C(O)R$_{10}$, —C(O)NR$_{10}$R$_{11}$, —C(O)NR$_{11}$A, —C≡CR$_8$, —CH═CHR$_8$, —W'A, —C≡CA, —CH═CHA, —W'YA, —W'YR$_{10}$, —W'Y(CH$_2$)$_j$A, —W'(CH$_2$)$_j$A, —W'(CH$_2$)$_j$R$_{10}$, —CHR$_{11}$W'(CH$_2$)$_j$R$_{10}$, —CHR$_{11}$W'(CH$_2$)$_j$A, —CHR$_{11}$NR$_{12}$YA, —CHR$_{11}$NR$_{12}$YR$_{10}$, —W'CHR$_{11}$(CH$_2$)$_j$A, —W'(CH$_2$)$_j$A(CH$_2$)$_k$D(CH$_2$)$_p$Z, —W'(CR$_{18}$R$_{19}$)A(CH$_2$)$_k$D(CH$_2$)$_p$Z, —(CH$_2$)$_j$W'A(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, —W'(CH$_2$)$_j$C≡CA(CH$_2$)$_k$D(CH$_2$)$_p$Z, and —W'(CH$_2$)$_j$Z;

W' can be a bond, —O—, —S—, —S(O)—, —S(O)$_2$—, —NR$_{11}$—, or —N(COR$_{12}$)—;

Y can be —CO—, —S(O)$_2$—, —CONR$_{13}$—, —CONR$_{13}$CO—, —CONR$_{13}$SO$_2$—, —C(NCN)—, —CSNR$_{13}$, —C(NH)NR$_{13}$, or —C(O)O—;

j can be 0 to 3; k can be 0 to 3; t can be 0 to 2;

D can be a bond, —CH═CH—, —C≡C—, —C═, —C(O)—, phenyl, —O—, —NH—, —S—, —CHR$_{14}$—, —CR$_{14}$R$_{15}$—, —OCHR$_{14}$—, —OCR$_{14}$R$_{15}$—, or —CH(OH)CH(OH)—;

p can be 0 to 3;

Z can be —CO$_2$R$_{11}$—, —CONR$_{10}$R$_{11}$, —C(═NR$_{10}$)NR$_{11}$R$_{12}$, —CONH$_2$NH$_2$, —CN, —CH$_2$OH, —NR$_{16}$R$_{17}$, phenyl, CONHCH(R$_{20}$)COR$_{12}$, phthalimide, pyrrolidine-2,5-dione, thiazolidine-2,4-dione, tetrazolyl, pyrrole, indole, oxazole, 2-thioxo-1,3-thiazolinin-4-one, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —CO$_2$CH$_3$, —CO$_2$H, —COCH$_3$, —CONH$_2$ and —CN; wherein said $C_1$ to $C_7$ amines are optionally substituted with one to two substituents independently selected from the group consisting of —OH, halogen, —OCH$_3$, and —C≡CH; wherein said phenyl is optionally substituted with CO$_2$R$_{11}$, and wherein said $C_3$ to $C_7$ cyclic amines are optionally substituted with one or two substituents independently selected from the group consisting of —OH —CH$_2$OH, C$_1$ to C$_3$ alkyl, —CH$_2$OCH$_3$, —CO$_2$CH$_3$, and —CONH$_2$, and wherein said oxazole is optionally substituted with CH$_2$CO$_2$R$_{11}$;

A can be phenyl, naphthyl, tetrahydronaphthyl, indan or biphenyl, each of which may be optionally substituted by one to four groups independently selected from halogen, C$_1$ to C$_3$ alkyl, C$_2$ to C$_4$ alkenyl, C$_2$ to C$_4$ alkynyl, acyl, hydroxy, halogen, —CN, —NO$_2$, —CO$_2$R$_{11}$, —CH$_2$CO$_2$R$_{11}$, phenyl, C$_1$ to C$_3$ perfluoroalkoxy, C$_1$ to C$_3$ perfluoroalkyl, —NR$_{10}$R$_{11}$, —CH$_2$NR$_{10}$R$_{11}$, —SR$_{11}$, C$_1$ to C$_6$ alkyl substituted with 1 to 5 fluorines, C$_1$ to C$_3$ alkyl substituted with 1 to 2-OH groups, C$_1$ to C$_6$ alkoxy optionally substituted with 1 to 5 fluorines, or phenoxy optionally substituted with 1 to 2 CF$_3$ groups; or A can be a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole, benzo[1,2,5]-oxadiazole, isochromen-1-one, benzothiophene, benzofuran, 2,3-dihydrobenzo[1,4]-dioxine, bitheinyl, quinazolin-2,4-91,3H]dione, and 3-H-isobenzofuran-1-one, each of which may be optionally substituted by one to three groups independently selected from halogen, C$_1$ to C$_3$ alkyl, acyl, hydroxy, —CN, —NO$_2$, C$_1$ to C$_3$ perfluoroalkyl, —NR$_{10}$R$_{11}$, —CH$_2$NR$_{10}$R$_{11}$, —SR$_{11}$, C$_1$ to C$_3$ alkyl substituted with 1 to 5 fluorines, and C$_1$ to C$_3$ alkoxy optionally substituted with 1 to 5 fluorines;

R$_{3'}$, R$_{4'}$, and R$_{5'}$ can each be, independently, —H or —F;

R$_6$ can be hydrogen, C$_1$ to C$_4$ alkyl, C$_1$ to C$_4$ perfluoroalkyl, halogen, —NO$_2$, —CN, phenyl or phenyl substituted with one or two groups independently selected from halogen, C$_1$ to C$_2$ alkyl and OH;

each R$_8$ can be independently —H, or C$_1$ to C$_3$ alkyl;
each R$_9$ can be independently —H, or C$_1$ to C$_3$ alkyl;
each R$_{10}$ can be independently —H, C$_1$ to C$_7$ alkyl, C$_3$ to C$_7$ alkenyl, C$_3$ to C$_7$ alkynyl, C$_3$ to C$_7$ cycloalkyl, —CH$_2$CH$_2$OCH$_3$, 2-methyl-tetrahydro-furan, 2-methyl-tetrahydro-pyran, 4-methyl-piperidine, morpholine, pyrrolidine, or phenyl optionally substituted with one or two C$_1$ to C$_3$ alkoxy groups, wherein said C$_1$ to C$_7$ alkyl is optionally substituted with 1, 2 or 3 groups independently selected from C$_1$ to C$_3$ alkoxy, C$_1$ to C$_3$ thioalkoxy and CN;

each R$_{11}$ can be independently —H, C$_1$ to C$_3$ alkyl or R$_{22}$;
or R$_{10}$ and R$_{11}$, when attached to the same atom, together with said atom can form:
(i) a 5 to 7 membered saturated ring, optionally substituted by 1 to 2 groups independently selected from C$_1$ to C$_3$ alkyl, OH and C$_1$-C$_3$ alkoxy; or
(ii) a 5 to 7 membered ring containing 1 or 2 heteroatoms, optionally substituted by 1 to 2 groups independently selected from C$_1$ to C$_3$ alkyl, OH and C$_1$-C$_3$ alkoxy;

each R$_{12}$ can be independently —H, or C$_1$ to C$_3$ alkyl;
each R$_{13}$ can be independently —H, or C$_1$ to C$_3$ alkyl;
each R$_{14}$ and R$_{15}$ can be, independently, C$_1$ to C$_7$ alkyl, C$_3$ to C$_8$ cycloalkyl, C$_2$ to C$_7$ alkenyl, C$_2$ to C$_7$ alkynyl, —OH, —F, C$_7$ to C$_{14}$ arylalkyl, where said arylalkyl is optionally substituted with 1 to 3 groups independently selected from NO$_2$, C$_1$ to C$_6$ alkyl, C$_1$ to C$_3$ perhaloalkyl, halogen, CH$_2$CO$_2$R$_{11}$, phenyl and C$_1$ to C$_3$ alkoxy, or R$_{14}$ and R$_{15}$ together with the atom to which they are attached can form a 3 to 7 membered saturated ring;

each R$_{16}$ and R$_{17}$ can be, independently, hydrogen, C$_1$ to C$_3$ alkyl, C$_1$ to C$_3$ alkenyl, C$_1$ to C$_3$ alkynyl, phenyl, benzyl or C$_3$ to C$_8$ cycloalkyl, wherein said C$_1$ to C$_3$ alkyl is optionally substituted with one OH group, and wherein said benzyl is optionally substituted with 1 to 3 groups selected from C$_1$ to C$_3$ alkyl and C$_1$ to C$_3$ alkoxy; or R$_{16}$ and R$_{17}$, together with the atom to which they are attached, can form a 3 to 8 membered heterocycle which is optionally substituted with one or two substituents independently selected from the group consisting of C$_1$ to C$_3$ alkyl, —OH, CH$_2$OH, —CH$_2$OCH$_3$, —CO$_2$CH$_3$, and —CONH$_2$;

each R$_{18}$ and R$_{19}$ can be, independently, C$_1$ to C$_3$ alkyl;
each R$_{20}$ can be independently H, phenyl, or the side chain of a naturally occurring alpha amino acid;
each R$_{22}$ can be independently arylalkyl optionally substituted with CH$_2$COOH; and
each R$_{23}$ can be phenyl; a compound of formula (VI) can be a salt or prodrug thereof (e.g., a pharmaceutically acceptable salt or prodrug). The invention also includes subgeneric positions related to formula (VI) provided subsequently in the Detailed Description of the Invention).

In one aspect, this invention relates to the specific cinnoline compounds delineated herein (e.g., in Examples 1-98).

In one aspect, this invention also relates generally to methods of treating, controlling, ameliorating, preventing, delaying the onset of, or reducing the risk of developing one or more LXR-mediated diseases or disorders in a subject (e.g., a subject in need thereof). The methods include administering to the subject an effective amount of a compound having any of the formulae described herein (e.g., a compound having formula (I), (V), or (VI) (or subgenera thereof), including the specific compounds described herein) or a pharmaceutically acceptable salt or prodrug thereof. LXR-mediated diseases or disorders can include, e.g., cardiovascular diseases (e.g., acute coronary syndrome, restenosis), atherosclerosis, atherosclerotic lesions, type I diabetes, type II diabetes, Syndrome X, obesity, lipid disorders (e.g., dyslipidemia, hyperlipidemia, hypertriglyceridemia, hypercholesterolemia, low HDL and high LDL), cognitive disorders (e.g., Alzheimer's disease, dementia), inflammatory diseases (e.g., multiple sclerosis, rheumatoid arthritis, inflammatory bowel disease, Crohn's disease, endometriosis, LPS-induced sepsis, acute contact dermatitis of the ear, chronic atherosclerotic inflammation of the artery wall), celiac, or thyroiditis.

In another aspect, this invention relates to methods of modulating (e.g., increasing) serum HDL cholesterol levels in a subject (e.g., a subject in need thereof), which includes administering to the subject an effective amount of a compound having any of the formulae described herein (e.g., a compound having formula (I), (V), or (VI) (or subgenera thereof), including the specific compounds described herein) or a pharmaceutically acceptable salt or prodrug thereof.

In another aspect, this invention relates to methods of modulating (e.g., decreasing) serum LDL cholesterol levels in a subject (e.g., a subject in need thereof), which includes administering to the subject an effective amount of a compound having any of the formulae described herein (e.g., a compound having formula (I), (V), or (VI) (or subgenera thereof), including the specific compounds described herein) or a pharmaceutically acceptable salt or prodrug thereof.

In another aspect, this invention relates to methods of modulating (e.g., increasing) reverse cholesterol transport in a subject (e.g., a subject in need thereof), which includes administering to the subject an effective amount of a compound having any of the formulae described herein (e.g., a compound having formula (I), (V), or (VI) (or subgenera thereof), including the specific compounds described herein) or a pharmaceutically acceptable salt or prodrug thereof.

In another aspect, this invention relates to methods of modulating (e.g., decreasing or inhibiting) cholesterol absorption in a subject (e.g., a subject in need thereof), which includes administering to the subject an effective amount of a compound having any of the formulae described herein (e.g., a compound having formula (I), (V), or (VI) (or subgenera thereof), including the specific compounds described herein) or a pharmaceutically acceptable salt or prodrug thereof.

In a further aspect, this invention relates to methods of preventing or treating a cardiovascular disease (e.g., acute coronary syndrome, restenosis), which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In one aspect, this invention relates to methods of preventing or treating a atherosclerosis and/or atherosclerotic lesions, which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In another aspect, this invention relates to methods of preventing or treating diabetes (e.g., type I diabetes or type 2 diabetes), which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In a further aspect, this invention relates to methods of preventing or treating Syndrome X, which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In one aspect, this invention relates to methods of preventing or treating a obesity, which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In another aspect, this invention relates to methods of preventing or treating a lipid disorder (e.g., dyslipidemia, hyperlipidemia, hypertriglyceridemia, hypercholesterolemia, low HDL and high LDL), which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In a further aspect, this invention relates to methods of preventing or treating a cognitive disorder (e.g., Alzheimer's disease or dementia), which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In a further aspect, this invention relates to methods of preventing or treating a Alzheimer's disease or dementia, which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In a further aspect, this invention relates to methods of preventing or treating a Alzheimer's disease, which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In one aspect, this invention relates to methods of preventing or treating an inflammatory disease (e.g., multiple sclerosis, rheumatoid arthritis, inflammatory bowel disease, Crohn's disease, endometriosis, LPS-induced sepsis, acute contact dermatitis of the ear, chronic atherosclerotic inflammation of the artery wall), which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In a further aspect, this invention relates to methods of preventing or treating celiac, which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In a further aspect, this invention relates to methods of preventing or treating thyroiditis, which includes administering to a subject in need thereof an effective amount of a compound having any of the formulae described herein (e.g., a compound having formula (I), (V), or (VI) (or subgenera thereof), including the specific compounds described herein) or a pharmaceutically acceptable salt or prodrug thereof.

In some embodiments, the compound (e.g., a compound having formula (I), (V), or (VI) (or subgenera thereof), including the specific compounds described herein) does not substantially increase serum and/or hepatic triglyceride levels of the subject.

In some embodiments, the administered compound can be an LXR agonist.

The invention also relates generally to modulating LXRs with the cinnoline compounds described herein. In some embodiments, the methods can include, e.g., contacting an LXR in a sample (e.g., a tissue, a cell free assay medium, a cell-based assay medium) with a compound having any of the formulae described herein (e.g., a compound having formula (I), (V), or (VI) (or subgenera thereof), including the specific compounds described herein). In other embodiments, the methods can include administering a compound having any of the formulae described herein (e.g., a compound having formula (I), (V), or (VI) (or subgenera thereof), including the specific compounds described herein) to a subject (e.g., a mammal, e.g., a human, e.g., a human having or at risk of having one or more of the diseases or disorders described herein).

In some embodiments, the subject can be a subject in need thereof (e.g., a subject identified as being in need of such treatment). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject is a human.

In a further aspect, this invention also relates to methods of making compounds described herein. Alternatively, the method includes taking any one of the intermediate compounds described herein and reacting it with one or more chemical reagents in one or more steps to produce a compound described herein.

In one aspect, this invention relates to a packaged product. The packaged product includes a container, one of the aforementioned compounds in the container, and a legend (e.g., a label or an insert) associated with the container and indicating administration of the compound for treatment and control of the diseases or disorders described herein.

In another aspect, the invention relates to a compound (including a pharmaceutically acceptable salt thereof) of any of the formulae delineated herein (e.g., a compound having formula (I), (V), or (VI) (or subgenera thereof), including the specific compounds described herein), or a composition comprising a compound (including a pharmaceutically acceptable salt thereof) of any of the formulae delineated herein. In some embodiments, the composition can further include a pharmaceutically acceptable adjuvant, carrier or diluent and/or an additional therapeutic agent.

The term "mammal" includes organisms, which include mice, rats, cows, sheep, pigs, rabbits, goats, and horses, monkeys, dogs, cats, and preferably humans.

"An effective amount" refers to an amount of a compound that confers a therapeutic effect (e.g., treats, controls, ameliorates, prevents, delays the onset of, or reduces the risk of developing a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/Kg to about 1000 mg/Kg, (e.g., from about 0.1 mg/Kg to about 100 mg/Kg, from about 1 mg/Kg to about 100 mg/Kg). Effective doses will also vary depending on route of administration, as well as the possibility of co-usage with other agents.

The term "halo" or "halogen" refers to any radical of fluorine (fluoro, F), chlorine (chloro, Cl), bromine (bromo, Br), or iodine (iodo, I).

The term "alkyl" refers to a hydrocarbon chain that may be a straight chain or branched chain, containing the indicated number of carbon atoms. For example, $C_1$-$C_{20}$ alkyl indicates that the group may have from 1 to 20 (inclusive) carbon atoms in it. Any atom can be substituted. Examples of alkyl groups include without limitation methyl, ethyl, and tert-butyl.

The term "cycloalkyl" refers to saturated monocyclic, bicyclic, tricyclic, or other polycyclic hydrocarbon groups. Any atom can be substituted, e.g., by one or more substituents. Cycloalkyl groups can contain fused rings. Fused rings are rings that share a common carbon atom. Cycloalkyl moieties can include, e.g., cyclopropyl, cyclohexyl, methylcyclohexyl adamantyl, and norbornyl. A ring carbon can optionally be the point of attachment to another moiety (e.g., for methylcyclohexyl and the like, the point of attachment can be either the methyl group or a cyclohexyl ring carbon).

The terms "haloalkyl" and "halocycloalkyl" refer to an alkyl or cycloalkyl group, respectively, in which at least one hydrogen atom is replaced by halo. In some embodiments, more than one hydrogen atom (2, 3, 4, 5, 6, 7, 8, 9, 10, 11, 12, 13, 14, 15, 16, 17, 18, 19, 20, 21, 22, 23, 24, 25, 26, etc. hydrogen atoms) on a alkyl or cycloalkyl group can be replaced by more than one halogens (e.g., 2, 3, 4, 5, 6, 7, 8, 9, 10, 11, 12, 13, 14, 15, 16, 17, 18, 19, 20, 21, 22, 23, 24, 25, 26, etc. hydrogen atoms), which can be the same or different. "Haloalkyl" and "halocycloalkyl" also include alkyl moieties in which all hydrogens have been replaced by halo (e.g., perhaloalkyl and perhalocycloalkyl, such as trifluoromethyl and perfluorocyclohexyl, respectively).

The term "aralkyl" refers to an alkyl moiety in which an alkyl hydrogen atom is replaced by an aryl group. Aralkyl includes groups in which more than one hydrogen atom on an alkyl moiety has been replaced by an aryl group. Any ring or chain atom can be substituted e.g., by one or more substituents. Examples of "aralkyl" include without limitation benzyl, 2-phenylethyl, 3-phenylpropyl, benzhydryl, and trityl groups.

The term "heteroaralkyl" refers to an alkyl moiety in which an alkyl hydrogen atom is replaced by a heteroaryl group. Heteroaralkyl includes groups in which more than one hydrogen atom on an alkyl moiety has been replaced by a heteroaryl group. Any ring or chain atom can be substituted e.g., by one or more substituents. Heteroaralkyl can include, for example, 2-pyridylethyl.

The term "alkenyl" refers to a straight or branched hydrocarbon chain containing 2-20 carbon atoms and having one or more double bonds. Any atom can be substituted, e.g., by one or more substituents. Alkenyl groups can include, e.g., allyl, propenyl, 2-butenyl, 3-hexenyl and 3-octenyl groups. One of the double bond carbons can optionally be the point of attachment of the alkenyl substituent. The term "alkynyl" refers to a straight or branched hydrocarbon chain containing 2-20 carbon atoms and having one or more triple bonds. Any atom can be substituted, e.g., by one or more substituents. Alkynyl groups can include, e.g., ethynyl, propargyl, and 3-hexynyl. One of the triple bond carbons can optionally be the point of attachment of the alkynyl substituent.

Alkylene, alkenylene, and alkynylene refer to divalent alkyl, alkenyl, and alkynyl moieties, respectively (e.g., —$CH_2$—, —CH=CH—, and —C≡C—, respectively). Any atom can be substituted.

The term "alkoxy" refers to an —O-alkyl radical. The term "mercapto" refers to an SH radical. The term "thioalkoxy" refers to an —S-alkyl radical. The terms "aryloxy" and "heteroaryloxy" refer to an —O-aryl radical and —O-heteroaryl radical, respectively. The terms "thioaryloxy" and "thioheteroaryloxy" refer to an —S-aryl radical and —S-heteroaryl radical, respectively. The terms "aralkoxy" and "heteroaralkoxy" refer to an —O-aralkyl radical and —O-heteroaralkyl radical, respectively. The terms "thioaralkoxy" and "thioheteroaralkoxy" refer to an —S-aralkyl radical and —S-heteroaralkyl radical, respectively. The terms "cycloalkoxy" and "halocycloalkoxy" refer to an —O-cycloalkyl radical and —O-halocycloalkyl radical, respectively. The terms "thiocycloalkoxy" and "thiohalocycloalkoxy" refer to an —S-cycloalkyl radical and —S-halocycloalkyl radical, respectively. The terms "cycloalkenyloxy" and "heterocycloalkenyloxy" refer to an —O-cycloalkenyl radical and —O-heterocycloalkenyl radical, respectively. The terms "thiocycloalkenyloxy" and "thioheterocycloalkenyloxy" refer to an —S-cycloalkenyl radical and —S-heterocycloalkenyl radical, respectively. The term "heterocyclyloxy" refers to an —O-heterocyclyl radical. The term "thioheterocyclyloxy" refers to an —S-heterocyclyl radical.

The term "aryl" refers to an aromatic monocyclic, bicyclic, or tricyclic hydrocarbon ring system, wherein any ring atom can be substituted, e.g., by one or more substituents. Aryl groups can contain fused rings. Fused rings are rings that share a common carbon atom. Aryl moieties can include, e.g., phenyl, naphthyl, anthracenyl, and pyrenyl.

The term "heterocyclyl" refers to a monocyclic, bicyclic, tricyclic or other polycyclic ring system having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). The heteroatom or ring carbon can optionally be the point of attachment of the heterocyclyl substituent to another moiety (e.g., for 4-methylpiperidinyl or 1-methylpiperidinyl, the point of attachment can be either the methyl group or a ring atom, e.g., carbon or nitrogen). Any atom can be substituted, e.g., by one or more substituents. The heterocyclyl groups can contain fused rings. Fused rings are rings that share a common carbon atom. Heterocyclyl groups can include, e.g., tetrahydrofuranyl, tetrahydropyranyl, piperidinyl, morpholino, pyrrolinyl, and pyrrolidinyl.

The term "cycloalkenyl" refers to partially unsaturated monocyclic, bicyclic, tricyclic, or other polycyclic hydrocarbon groups. A ring carbon (e.g., saturated or unsaturated) can optionally be the point of attachment of the cycloalkenyl substituent (e.g., for methylcyclohexenyl and the like, the point of attachment can be either the methyl group or a cyclohexenyl ring carbon). Any atom can be substituted e.g., by one or more substituents. The cycloalkenyl groups can contain fused rings. Fused rings are rings that share a common carbon atom. Cycloalkenyl moieties can include, e.g., cyclohexenyl, cyclohexadienyl, norbornenyl, or cyclooctatetraenyl.

The term "heterocycloalkenyl" refers to partially unsaturated monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). A ring carbon (e.g., saturated or unsaturated) or heteroatom can optionally be the point of attachment of the heterocycloalkenyl substituent (e.g., for methyldihydropyranyl and the like, the point of attachment can be either the methyl group or a ring carbon). Any atom can be substituted, e.g., by one or more substituents. The heterocycloalkenyl groups can contain fused rings. Fused rings are rings that share a common carbon atom. Heterocycloalkenyl groups can include, e.g., tetrahydropyridyl, and dihydropyranyl.

The term "heteroaryl" refers to an aromatic monocyclic, bicyclic, tricyclic, or other polycyclic hydrocarbon groups having 1-4 heteroatoms if monocyclic, 1-8 heteroatoms if bicyclic, or 1-10 heteroatoms if tricyclic, said heteroatoms selected from O, N, or S (e.g., carbon atoms and 1-4, 1-8, or 1-10 heteroatoms of N, O, or S if monocyclic, bicyclic, or tricyclic, respectively). Any atom can be substituted, e.g., by one or more substituents. Heteroaryl groups can contain fused rings. Fused rings are rings that share a common carbon atom. Heteroaryl groups include pyridyl, thienyl, furanyl, imidazolyl, and pyrrolyl.

The term "oxo" refers to an oxygen atom, which forms a carbonyl (C=O) when attached to carbon, an N-oxide when attached to nitrogen, and a sulfoxide or sulfone when attached to sulfur. The term "thioxo" refers to an oxygen atom, which forms a thiocarbonyl (C=S) when attached to carbon.

The term "substituent" refers to a group "substituted" on, e.g., an alkyl, cycloalkyl, alkenyl, alkynyl, aralkyl, heteroaralkyl, heterocyclyl, heterocycloalkenyl, cycloalkenyl, aryl, or heteroaryl group at any atom of that group. In one aspect, the substituents (e.g., $R^3$) on a group are independently any one single, or any combination of two or more of the permissible atoms or groups of atoms delineated for that substituent. In another aspect, a substituent may itself be substituted with any one of the above substituents (e.g., $R^g$).

In some embodiments, the compounds have agonist activity for genes involved with HDL production and cholesterol efflux (e.g., ABCA1) and antagonist activity for genes involved with triglyceride synthesis (e.g., SREBP-1c).

The details of one or more embodiments of the invention are set forth in the description below. Other features and advantages of the invention will be apparent from the description and from the claims.

DETAILED DESCRIPTION

The cinnoline-based, LXR modulators can have the general formula (I) below:

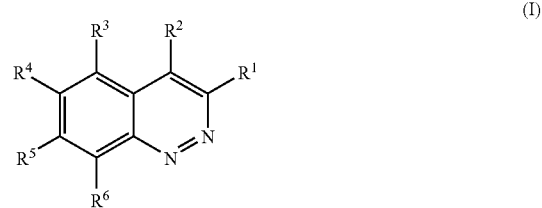

(I)

In some embodiments, $R^1$ can be hydrogen.

In some embodiments, $R^1$ can be $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkyl or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, each of which can be optionally substituted with from 1-10 (e.g., 1, 2, 3, 4, 5, 6, 7, 8, 9, or 10) $R^a$.

In some embodiments, $R^1$ can be $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which can be optionally substituted with from 1-10 (e.g., 1, 2, 3, 4, 5, 6, 7, 8, 9, or 10) $R^b$.

In some embodiments, $R^1$ can be $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl, heteroaralkyl including 6-20 (e.g., 6, 7, 8, 9, 10, 11, 12, 13, 14, 15, 16, 17, 18, 19, or 20) atoms, each of which can be optionally substituted with from 1-10 (e.g., 1, 2, 3, 4, 5, 6, 7, 8, 9, or 10) $R^c$.

In some embodiments, $R^1$ can be $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^d$.

In some embodiments, $R^1$ can be $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{13}$, $C_{19}$, or $C_{20}$) halocycloalkyl, optionally substituted with from 1-10 (e.g., 1, 2, 3, 4, 5, 6, 7, 8, 9, or 10) $R^e$.

In some embodiments, $R^1$ can be $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$.

In some embodiments, $R^1$ can be —C(O)NR$^g$R$^h$; —OC(O)NR$^g$R$^h$; —C(O)R$^i$; —C(O)OR$^i$; —OC(O)R$^i$; —C(O)SR$^i$; —SC(O)R$^i$; —C(S)SR$^i$; —SC(S)R$^i$; —NR$^j$C(O)R$^i$; —NR$^j$C(O)OR$^i$; —NR$^j$C(O)NR$^g$R$^h$; —S(O)$_n$R$^k$; —NR$^j$S(O)$_n$R$^i$; —C(NR$^m$)R$^i$; or —P(O)(OR$^g$)(OR$^h$).

In some embodiments, $R^2$ can be $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which can be optionally substituted with from 1-10 (e.g., 1, 2, 3, 4, 5, 6, 7, 8, 9, or 10) $R^b$.

In some embodiments, $R^2$ can be $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl, heteroaralkyl including 6-20 (e.g., 6, 7, 8, 9, 10, 11, 12, 13, 14, 15, 16, 17, 18, 19, or 20) atoms, each of which can be optionally substituted with from 1-10 (e.g., 1, 2, 3, 4, 5, 6, 7, 8, 9, or 10) $R^c$.

In some embodiments, $R^2$ can be $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) $R^e$.

In some embodiments, $R^2$ can be $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$.

Each of $R^3$, $R^4$, $R^5$, and $R^6$ can be, independently of one another:

(i) hydrogen, halo; $NR^gR^h$; nitro; azido, hydroxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkoxy or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or $C_{20}$) haloalkoxy, each of which is optionally substituted with from 1-10 (e.g., 1, 2, 3, 4, 5, 6, 7, 8, 9, or 10) $R^a$; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy or heteroaryloxy including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy or heteroaralkoxy including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy, each of which is optionally substituted with from 1-10 (e.g., 1, 2, 3, 4, 5, 6, 7, 8, 9, or 10) $R^e$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy, heterocyclyloxy including 3-20 (e.g., 3, 4, 5, 6, 7, 8, 9, 10, 11, 12, 13, 14, 15, 16, 17, 18, 19, or 20) atoms, or heterocycloalkenyloxy including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioalkoxy or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohaloalkoxy, each of which is optionally substituted with from 1-10 (e.g., 1, 2, 3, 4, 5, 6, 7, 8, 9, or 10) $R^a$; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy or thioheteroaryloxy including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy or thioheteroaralkoxy including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy, each of which is optionally substituted with from 1-10 (e.g., 1, 2, 3, 4, 5, 6, 7, 8, 9, or 10) $R^e$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkenyloxy, thioheterocyclyloxy including 3-20 (e.g., 3, 4, 5, 6, 7, 8, 9, 10, 11, 12, 13, 14, 15, 16, 17, 18, 19, or 20) atoms, or thioheterocycloalkenyloxy including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$; cyano; formyl; $C_1$-$C_3$ (e.g., $C_1$, $C_2$, or $C_3$) alkylenedioxy; —C(O)$NR^gR^h$; —OC(O)$NR^gR^h$; —C(O)$R^i$, —C(O)O$R^i$; —OC(O)$R^i$; —C(O)S$R^i$; —SC(O)$R^i$; —C(S)S$R^i$; —SC(S)$R^i$; —$NR^j$C(O)$R^i$; —$NR^j$C(O)O$R^i$; —$NR^c$(O)$NR^gR^i$; —S(O)$_n R^k$; —$NR^j$S(O)$_n R^i$; —C($NR^m$)$R^i$; or —P(O)(O$R^g$)(O$R^h$); or (ii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$)alkyl or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, each of which is optionally substituted with from 1-10 (e.g., 1, 2, 3, 4, 5, 6, 7, 8, 9, or 10) $R^a$; or (iii) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) $R^e$; or (iv) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$; or (v) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^d$; or (vi) $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl or heteroaralkyl including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$; or (vii) $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$.

Each $R^a$ can be, independently of one another, $NR^gR^h$; nitro; azido; hydroxy; oxo; thioxo; =$NR^m$; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy or heteroaryloxy including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy or heteroaralkoxy including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy; heterocyclyloxy including 3-20 (e.g., 3, 4, 5, 6, 7, 8, 9, 10, 11, 12, 13, 14, 15, 16, 17, 18, 19, or 20) atoms; heterocycloalkenyloxy including 3-20 (e.g., 3, 4, 5, 6, 7, 8, 9, 10, 11, 12, 13, 14, 15, 16, 17, 18, 19, or 20) atoms; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioalkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{18}$, or $C_{20}$) thiohaloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy; thioheteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy; thioheteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkenyloxy; thioheterocyclyloxy including 3-20 (e.g., 3, 4, 5, 6, 7, 8, 9, 10, 11, 12, 13, 14, 15, 16, 17, 18, 19, or 20) atoms; thioheterocycloalkenyloxy including 3-20 (e.g., 3, 4, 5, 6, 7, 8, 9, 10, 11, 12, 13, 14, 15, 16, 17, 18, 19, or 20) atoms; cyano; formyl; $C_1$-$C_3$ (e.g., $C_1$, $C_2$, or $C_3$) alkylenedioxy; —C(O)NR$^g$R$^h$; —OC(O)NR$^g$R$^h$; —C(O)R$^i$, —C(O)OR$^i$; —OC(O)R$^i$; —C(O)SR$^i$; —SC(O)R$^i$; —C(S)SR$^i$; —SC(S)R$^i$; —NR$^j$C(O)R$^i$; —NR$^j$C(O)OR$^i$; —NR$^j$C(O)NR$^g$R$^h$; —S(O)$_n$R$^k$; —NR$^j$S(O)$_n$R$^i$; —C(NR$^m$)R$^i$; or —P(O)(OR$^g$)(OR$^h$).

Each $R^b$ can be, independently of one another:

(i) halo; NR$^g$R$^h$; nitro; azido; hydroxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkoxy or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkoxy, each of which is optionally substituted with from 1-10 (e.g., 1, 2, 3, 4, 5, 6, 7, 8, 9, or 10) $R^a$; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy or heteroaryloxy including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$ or $R^{b'}$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy or heteroaralkoxy including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy, each of which is optionally substituted with from 1-10 (e.g., 1, 2, 3, 4, 5, 6, 7, 8, 9, or 10) $R^e$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy, heterocyclyloxy including 3-20 (e.g., 3, 4, 5, 6, 7, 8, 9, 10, 11, 12, 13, 14, 15, 16, 17, 18, 19, or 20) atoms, or heterocycloalkenyloxy including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioalkoxy or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohaloalkoxy, each of which is optionally substituted with from 1-10 (e.g., 1, 2, 3, 4, 5, 6, 7, 8, 9, or 10) $R^a$; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy or thioheteroaryloxy including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$ or $R^{b'}$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy or thioheteroaralkoxy including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy, each of which is optionally substituted with from 1-10 (e.g., 1, 2, 3, 4, 5, 6, 7, 8, 9, or 10) $R^e$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_3$, $C_{14}$, $C_{15}$, $C_{16}$, $C_{17}$, $C_{18}$, $C_{19}$, or $C_{20}$) thiocycloalkenyloxy, thioheterocyclyloxy including 3-20 (e.g., 3, 4, 5, 6, 7, 8, 9, 10, 11, 12, 13, 14, 15, 16, 17, 18, 19, or 20) atoms, or thioheterocycloalkenyloxy including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$; cyano; formyl; $C_1$-$C_3$ (e.g., $C_1$, $C_2$, or $C_3$) alkylenedioxy; —C(O)NR$^g$R$^h$; —OC(O)NR$^g$R$^h$; —C(O)R$^i$, —C(O)OR$^i$; —OC(O)R$^i$; —C(O)SR$^i$; —SC(O)R$^i$; —C(S)SR$^i$; —SC(S)R$^i$; —NR$^j$C(O)R$^i$; —NR$^j$C(O)OR$^i$; —NR$^j$C(O)NR$^g$R$^h$; —S(O)$_n$R$^k$; —NR$^j$S(O)$_n$R$^i$; —C(NR$^m$)R$^i$; or —P(O)(OR$^g$)(OR$^h$);

(ii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$)alkyl or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, each of which is optionally substituted with from 1-10 (e.g., 1, 2, 3, 4, 5, 6, 7, 8, 9, or 10) $R^a$; or (iii) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) $R^e$; or (iv) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^f$; or (v) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^d$; or (vi) $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl or heteroaralkyl including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$; or (vii) $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$.

Each $R^{b'}$ can be, independently of one another, halo; NR$^g$R$^h$; nitro; azido; hydroxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy; heteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy; heteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy; heterocyclyloxy including 3-20 (e.g., 3, 4, 5, 6, 7, 8, 9, 10, 11, 12, 13, 14, 15, 16, 17, 18, 19, or 20) atoms; heterocycloalkenyloxy including 3-20 (e.g., 3, 4, 5, 6, 7, 8, 9, 10, 11, 12, 13, 14, 15, 16, 17, 18, 19, or 20) atoms; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioalkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohaloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy; thioheteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy; thioheteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkenyloxy; thioheterocyclyloxy including 3-20 (e.g., 3, 4, 5, 6, 7, 8, 9, 10, 11, 12, 13, 14, 15, 16, 17, 18, 19, or 20) atoms; thioheterocycloalkenyloxy including 3-20 (e.g., 3, 4, 5, 6, 7, 8, 9, 10, 11, 12, 13, 14, 15, 16, 17, 18, 19, or 20) atoms; cyano; formyl; $C_1$-$C_3$ (e.g., $C_1$, $C_2$, or $C_3$) alkylenedioxy; —C(O)NR$^g$R$^h$; —OC(O)NR$^g$R$^h$; —C(O)R$^i$, —C(O)OR$^i$; —OC(O)R$^i$; —C(O)SR$^i$; —SC(O) R$^i$; —C(S)SR$^i$; —SC(S)R$^i$; —NR$^j$C(O)R$^i$; —NR$^j$C(O)OR$^i$; —NR$^j$C(O)NR$^g$R$^h$; —S(O)$_n$R$^k$; —NR$^j$S(O)$_n$R$^i$; —C(NR$^m$) R$^i$; or —P(O)(OR$^g$)(OR$^h$)

Each R$^c$ can be, independently of one another:

(i) halo; NR$^g$R$^h$; nitro; azido; hydroxy; oxo; thioxo; =NR$^m$; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkoxy or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkoxy, each of which is optionally substituted with from 1-10 (e.g., 1, 2, 3, 4, 5, 6, 7, 8, 9, or 10) R$^a$; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy or heteroaryloxy including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) R$^b$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy or heteroaralkoxy including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) R$^c$ or R$^{c'}$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy, each of which is optionally substituted with from 1-10 (e.g., 1, 2, 3, 4, 5, 6, 7, 8, 9, or 10) R$^e$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy, heterocyclyloxy including 3-20 (e.g., 3, 4, 5, 6, 7, 8, 9, 10, 11, 12, 13, 14, 15, 16, 17, 18, 19, or 20) atoms, or heterocycloalkenyloxy including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) R$^f$; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_2$, $C_{13}$, $C_{14}$, $C_{15}$, $C_{16}$, $C_{17}$, $C_{18}$, $C_{19}$, or $C_{20}$) thioalkoxy or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohaloalkoxy, each of which is optionally substituted with from 1-10 (e.g., 1, 2, 3, 4, 5, 6, 7, 8, 9, or 10) R$^a$; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy or thioheteroaryloxy including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) R$^b$; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy or thioheteroaralkoxy including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) R$^c$ or R$^{c'}$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy, each of which is optionally substituted with from 1-10 (e.g., 1, 2, 3, 4, 5, 6, 7, 8, 9, or 10) R$^e$; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkenyloxy, thioheterocyclyloxy including 3-20 (e.g., 3, 4, 5, 6, 7, 8, 9, 10, 11, 12, 13, 14, 15, 16, 17, 18, 19, or 20) atoms, or thioheterocycloalkenyloxy including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) R$^f$; cyano; formyl; $C_1$-$C_3$ (e.g., $C_1$, $C_2$, or $C_3$) alkylenedioxy; —C(O)NR$^g$R$^h$; —OC(O)NR$^g$R$^h$; —C(O)R$^i$, —C(O)OR$^i$; —OC(O)R$^i$; —C(O)SR$^i$; —SC(O)R$^i$; —C(S) SR$^i$; —SC(S)R$^i$; —NR$^j$C(O)R$^i$; —NR$^j$C(O)OR$^i$; —NR$^j$C(O) NR$^g$R$^h$; —S(O)$_n$R$^k$; —NR$^j$S(O)$_n$R$^i$; —C(NR$^m$)R$^i$; or —P(O) (OR$^g$)(OR$^h$);

(ii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$)alkyl or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, each of which is optionally substituted with from 1-10 (e.g., 1, 2, 3, 4, 5, 6, 7, 8, 9, or 10) R$^a$; or (iii) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) R$^e$; or (iv) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) R$^f$; or (v) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) R$^d$; or (vi) $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl or heteroaralkyl including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) $R^c$ or $R^{c'}$; or (vii) $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$.

Each $R^{c'}$ can be, independently of one another, oxo; thioxo; =$NR^m$; or $R^{b'}$;

Each $R^d$ can be, independently of one another, halo; $NR^gR^h$; nitro; azido; hydroxy; oxo; thioxo; =$NR^m$; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{18}$, or $C_{20}$) alkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy; heteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy; heteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy; heterocyclyloxy including 3-20 (e.g., 3, 4, 5, 6, 7, 8, 9, 10, 11, 12, 13, 14, 15, 16, 17, 18, 19, or 20) atoms; heterocycloalkenyloxy including 3-20 (e.g., 3, 4, 5, 6, 7, 8, 9, 10, 11, 12, 13, 14, 15, 16, 17, 18, 19, or 20) atoms; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioalkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohaloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy; thioheteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy; thioheteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkenyloxy; thioheterocyclyloxy including 3-20 (e.g., 3, 4, 5, 6, 7, 8, 9, 10, 11, 12, 13, 14, 15, 16, 17, 18, 19, or 20) atoms; thioheterocycloalkenyloxy including 3-20 (e.g., 3, 4, 5, 6, 7, 8, 9, 10, 11, 12, 13, 14, 15, 16, 17, 18, 19, or 20) atoms; cyano; formyl; $C_1$-$C_3$ (e.g., $C_1$, $C_2$, or $C_3$) alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$).

Each $R^e$ can be, independently of one another:

(i) $NR^gR^h$; nitro; azido; hydroxy; oxo; thioxo; =$NR^m$; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy; heteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy; heteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy; heterocyclyloxy including 3-20 (e.g., 3, 4, 5, 6, 7, 8, 9, 10, 11, 12, 13, 14, 15, 16, 17, 18, 19, or 20) atoms; heterocycloalkenyloxy including 3-20 (e.g., 3, 4, 5, 6, 7, 8, 9, 10, 11, 12, 13, 14, 15, 16, 17, 18, 19, or 20) atoms; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioalkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohaloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy; thioheteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy; thioheteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkenyloxy; thioheterocyclyloxy including 3-20 (e.g., 3, 4, 5, 6, 7, 8, 9, 10, 11, 12, 13, 14, 15, 16, 17, 18, 19, or 20) atoms; thioheterocycloalkenyloxy including 3-20 (e.g., 3, 4, 5, 6, 7, 8, 9, 10, 11, 12, 13, 14, 15, 16, 17, 18, 19, or 20) atoms; cyano; formyl; $C_1$-$C_3$ (e.g., $C_1$, $C_2$, or $C_3$) alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$);

(ii) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) $R^d$; or (iii) $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) $R^b$.

Each $R^f$ can be, independently of one another:

(i) halo; $NR^gR^h$; nitro; azido; hydroxy; oxo; thioxo; =$NR^m$; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryloxy; heteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkoxy; heteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyloxy; heterocyclyloxy including 3-20 (e.g., 3, 4, 5, 6, 7, 8, 9, 10, 11, 12, 13, 14, 15, 16, 17, 18, 19, or 20) atoms; heterocycloalkenyloxy including 3-20 (e.g., 3, 4, 5, 6, 7, 8, 9, 10, 11, 12, 13, 14, 15, 16, 17, 18, 19, or 20) atoms; mercapto; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioalkoxy; $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohaloalkoxy; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) thioaryloxy; thioheteroaryloxy including 5-16 (e.g., 5, 6, 7, 8, 9, 10, 11, 12, 13, 14, 15, or 16) atoms; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thioaralkoxy; thioheteroaralkoxy including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiohalocycloalkoxy; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) thiocycloalkenyloxy; thioheterocyclyloxy including 3-20 (e.g., 3, 4, 5, 6, 7, 8, 9, 10, 11, 12, 13, 14, 15, 16, 17, 18, 19, or 20) atoms; thioheterocycloalkenyloxy including 3-20 (e.g., 3, 4, 5, 6, 7, 8, 9, 10, 11, 12, 13, 14, 15, 16, 17, 18, 19, or 20) atoms; cyano; formyl; $C_1$-$C_3$ (e.g., $C_1$, $C_2$, or $C_3$) alkylenedioxy; —C(O)NR$^g$R$^h$; —OC(O)NR$^g$R$^h$; —C(O)R$^i$, —C(O)OR$^i$; —OC(O)R$^i$; —C(O)SR$^i$; —SC(O)R$^i$; —C(S)SR$^i$; —SC(S)R$^i$; —NR$^j$C(O)R$^i$; —NR$^j$C(O)OR$^i$; —NR$^j$C(O)NR$^g$R$^h$; —S(O)$_n$R$^k$; —NR$^j$S(O)$_n$R$^i$; —C(NR$^m$)R$^i$; or —P(O)(OR$^g$)(OR$^h$);

(ii) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) R$^d$; or (iii) $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) R$^b$.

Each R$^g$, R$^h$, R$^i$, and R$^j$ can be, independently of one another:

(i) hydrogen; or (ii) $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$)alkyl or $C_1$-$C_{20}$ (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) haloalkyl, each of which is optionally substituted with from 1-10 (e.g., 1, 2, 3, 4, 5, 6, 7, 8, 9, or 10) R$^a$; or (iii) $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl or $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl, each of which is optionally substituted with from 1-10 (e.g., 1, 2, 3, 4, 5, 6, 7, 8, 9, or 10) R$^d$;

(iv) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl, heterocyclyl including 3-20 (e.g., 3, 4, 5, 6, 7, 8, 9, 10, 11, 12, 13, 14, 15, 16, 17, 18, 19, or 20) atoms, or heterocycloalkenyl including 3-20 (e.g., 3, 4, 5, 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) R$^f$; or (v) $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl or $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) halocycloalkyl, optionally substituted with from 1-10 (e.g., 1, 2, 3, 4, 5, 6, 7, 8, 9, or 10) R$^e$; or (vi) $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl or heteroaralkyl including 6-20 (e.g., 6, 7, 8, 9, 10, 11, 12, 13, 14, 15, 16, 17, 18, 19, or 20) atoms, each of which is optionally substituted with from 1-10 (e.g., 1, 2, 3, 4, 5, 6, 7, 8, 9, or 10) R$^c$ or R$^{c'}$; or (vii) $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl or heteroaryl including 5-16 (e.g., 5, 6, 7, 8, 9, 10, 11, 12, 13, 14, 15, or 16) atoms, each of which is optionally substituted with from 1-10 (e.g., 1, 2, 3, 4, 5, 6, 7, 8, 9, or 10) R$^b$.

Each R$^k$ can be, independently of one another, R$^i$, OR$^i$, or NR$^g$R$^h$.

Each R$^m$ can be, independently of one another, hydrogen; $C_1$-$C_{12}$ (e.g., $C_1$, $C_2$, $C_3$, $C_4$, $C_5$, $C_6$, $C_7$, $C_8$, $C_9$, $C_{10}$, Cu, or $C_{12}$) alkyl or $C_1$-$C_{12}$ (e.g., $C_1$, $C_2$, $C_3$, $C_4$, $C_5$, $C_6$, $C_7$, $C_8$, $C_9$, $C_{10}$, $C_{11}$, or $C_{12}$) haloalkyl, each of which is optionally substituted with from 1-5 (e.g., 1, 2, 3, 4, or 5) R$^a$; $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkenyl; $C_2$-$C_{20}$ (e.g., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) alkynyl; $C_7$-$C_{20}$ (e.g., $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) aralkyl; heteroaralkyl including 6-20 (e.g., 6, 7, 8, 9, 10, 11, 12, 13, 14, 15, 16, 17, 18, 19, or 20) atoms; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkyl; $C_3$-$C_{20}$ (e.g., $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$) cycloalkenyl; heterocyclyl including 3-20 (e.g., 3, 4, 5, 6, 7, 8, 9, 10, 11, 12, 13, 14, 15, 16, 17, 18, 19, or 20) atoms; heterocycloalkenyl including 3-20 (e.g., 3, 4, 5, 6, 7, 8, 9, 10, 11, 12, 13, 14, 15, 16, 17, 18, 19, or 20) atoms; $C_6$-$C_{18}$ (e.g., $C_6$, $C_7$, $C_8$, $C_9$, $C_{10}$, $C_{11}$, $C_{12}$, $C_{13}$, $C_{14}$, $C_{15}$, $C_{16}$, $C_{17}$, or $C_{18}$) aryl; heteroaryl including 5-16 (e.g., 5, 6, 7, 8, 9, 10, 11, 12, 13, 14, 15, or 16) atoms; NR$^g$R$^h$, or OR$^i$.

Each n can be 0, 1, or 2.

For ease of exposition, it is understood that any recitation of ranges (e.g., $C_1$-$C_{20}$) or subranges of a particular range (e.g., $C_1$-$C_4$, $C_2$-$C_6$) for any of R$^1$, R$^2$, R$^3$, R$^4$, R$^5$, R$^6$, n, R$^a$, R$^b$, R$^{b'}$, R$^c$, R$^{c'}$, R$^d$ R$^e$, R$^f$, R$^g$, R$^h$, R$^i$, R$^j$, R$^k$, or R$^m$ expressly includes each of the individual values that fall within the recited range, including the upper and lower limits of the recited range. For example, the range $C_1$-$C_4$ alkyl is understood to mean (e.g., $C_1$, $C_2$, $C_3$, or $C_4$) alkyl.

In some embodiments, R$^2$ can be $C_6$-$C_{18}$ (e.g., $C_6$-$C_{14}$, $C_6$-$C_{10}$, $C_6$) aryl optionally substituted with from 1-10 (e.g., 1-5, 1-4, 1-3, 1-2, 1) R$^b$; $C_7$-$C_{20}$ (e.g., $C_7$-$C_{16}$, $C_7$-$C_{12}$, $C_7$-$C_{10}$) aralkyl optionally substituted with from 1-10 (e.g., 1-5, 1-4, 1-3, 1-2, 1) R$^c$; $C_3$-$C_{20}$ (e.g., $C_3$-$C_{16}$, $C_3$-$C_{12}$, $C_3$-$C_8$) cycloalkyl or $C_3$-$C_{20}$ (e.g., $C_3$-$C_{16}$, $C_3$-$C_{12}$, $C_3$-$C_8$) halocycloalkyl, optionally substituted with from 1-10 (e.g., 1-5, 1-4, 1-3, 1-2, 1) R$^e$; or $C_3$-$C_{20}$ (e.g., $C_3$-$C_{16}$, $C_3$-$C_{12}$, $C_3$-$C_8$) cycloalkenyl optionally substituted with from 1-10 (e.g., 1-5, 1-4, 1-3, 1-2, 1) R$^f$.

In some embodiments, R$^2$ can be $C_6$-$C_{18}$ (e.g., $C_6$-$C_{14}$, $C_6$-$C_{10}$, $C_6$) aryl or heteroaryl including 5-16 (e.g., 5-14, 5-10, 5-6) atoms, each of which can be optionally substituted with from 1-10 (e.g., 1-5, 1-4, 1-3, 1-2, 1) R$^b$.

In some embodiments, R$^2$ can be $C_6$-$C_{18}$ (e.g., $C_6$-$C_{14}$, $C_6$-$C_{10}$, phenyl) aryl optionally substituted with from 1-10 (e.g., 1-5, 1-4, 1-3, 1-2, 1) R$^b$.

In some embodiments, R$^2$ can be $C_6$-$C_{10}$ aryl, optionally substituted with from 1-5 (e.g., 1-4, 1-3, 1-2, 1) R$^b$.

In some embodiments, R$^2$ can be phenyl, optionally substituted with from 1-5 (e.g., 1-4, 1-3, 1-2, 1) R$^b$. In certain embodiments, R$^2$ can be unsubstituted phenyl. In certain embodiments, R$^2$ can be phenyl substituted with 1, 2, 3, or 4 R$^b$. In certain embodiments, R$^2$ can be phenyl substituted with 2 R$^b$ or R$^2$ can be phenyl substituted with 1 R$^b$. In these embodiments, each R$^b$ can be attached to a carbon that is ortho, meta, or para to the phenyl carbon atom that is attached to the 4-position of the cinnoline ring.

In some embodiments, when $R^2$ is substituted with $R^b$, each $R^b$ can be, independently of one another:

(i) halo; $NO_2$; $NR^gR^h$; hydroxy; $C_1$-$C_{20}$ (e.g., $C_1$-$C_{10}$, $C_1$-$C_6$, $C_1$-$C_3$) alkoxy or $C_1$-$C_{20}$ (e.g., $C_1$-$C_{10}$, $C_1$-$C_6$, $C_1$-$C_3$) haloalkoxy, each of which is optionally substituted with from 1-10 (e.g., 1-5, 1-4, 1-3, 1-2, 1) $R^a$; $C_6$-$C_{18}$ (e.g., $C_6$-$C_{14}$, $C_6$-$C_{10}$, phenyl) aryloxy or heteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; $C_7$-$C_{20}$ (e.g., $C_7$-$C_{16}$, $C_7$-$C_{12}$, $C_7$-$C_{10}$) aralkoxy or heteroaralkoxy including 6-20 (e.g., 6-14, 6-12, 6-10) atoms, each of which is optionally substituted with from 1-10 (e.g., 1-5, 1-4, 1-3, 1-2, 1) $R^c$; $C_3$-$C_{20}$ (e.g., $C_3$-$C_{16}$, $C_3$-$C_{12}$, $C_3$-$C_8$) cycloalkoxy or $C_3$-$C_{20}$ (e.g., $C_3$-$C_{16}$, $C_3$-$C_{12}$, $C_3$-$C_8$) halocycloalkoxy, each of which is optionally substituted with from 1-10 (e.g., 1-5, 14, 1-3, 1-2, 1) $R^e$; $C_3$-$C_{20}$ (e.g., $C_3$-$C_{16}$, $C_3$-$C_{12}$, $C_3$-$C_8$) cycloalkenyloxy, heterocyclyloxy including 3-20 (e.g., 3-16, 3-12, 3-8) atoms, or heterocycloalkenyloxy including 3-20 (e.g., 3-16, 3-12, 3-8) atoms, each of which is optionally substituted with from 1-10 (e.g., 1-5, 1-4, 1-3, 1-2, 1) $R^f$; mercapto; $C_1$-$C_{20}$ (e.g., $C_1$-$C_{10}$, $C_1$-$C_6$, $C_1$-$C_3$) thioalkoxy or $C_1$-$C_{20}$ (e.g., $C_1$-$C_{10}$, $C_1$-$C_6$, $C_1$-$C_3$) thiohaloalkoxy, each of which is optionally substituted with from 1-10 (e.g., 1-5, 1-4, 1-3, 1-2, 1) $R^a$; $C_6$-$C_{18}$ (e.g., $C_6$-$C_{14}$, $C_6$-$C_{10}$, phenyl) thioaryloxy or thioheteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; $C_7$-$C_{20}$ (e.g., $C_7$-$C_{16}$, $C_7$-$C_{12}$, $C_7$-$C_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) $R^c$; $C_3$-$C_{20}$ (e.g., $C_3$-$C_{16}$, $C_3$-$C_{12}$, $C_3$-$C_8$) thiocycloalkoxy or $C_3$-$C_{20}$ (e.g., $C_3$-$C_{16}$, $C_3$-$C_{12}$, $C_3$-$C_8$) thiohalocycloalkoxy, each of which is optionally substituted with from 1-10 (e.g., 1-5, 1-4, 1-3, 1-2, 1) $R^e$; $C_3$-$C_{20}$ (e.g., $C_3$-$C_{16}$, $C_3$-$C_{12}$, $C_3$-$C_8$) thiocycloalkenyloxy, thioheterocyclyloxy including 3-20 (e.g., 3-16, 3-12, 3-8) atoms, or thioheterocycloalkenyloxy including 3-20 (e.g., 3-16, 3-12, 3-8) atoms, each of which is optionally substituted with from 1-10 (e.g., 1-5, 1-4, 1-3, 1-2, 1) $R^f$; cyano; —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^i$; —$NR^jC(O)NR^gR^h$; —S(O)$_nR^k$; —$NR^jS(O)_nR^i$; —C($NR^m$)$R^i$; or —P(O)(O$R^g$)(O$R^h$);

(ii) $C_1$-$C_{20}$ (e.g., $C_1$-$C_{10}$, $C_1$-$C_6$, $C_1$-$C_3$) alkyl or $C_1$-$C_{20}$ (e.g., $C_1$-$C_{10}$, $C_1$-$C_6$, $C_1$-$C_3$) haloalkyl, each of which is optionally substituted with from 1-10 (e.g., 1-5, 1-4, 1-3, 1-2, 1) $R^a$; or (vi) $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$; or (vii) $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^{b'}$.

In some embodiments, when $R^2$ is substituted with $R^b$, each $R^b$ can be, independently of one another:

(i) halo; $NO_2$; $NR^gR^h$; hydroxy; $C_1$-$C_{20}$ (e.g., $C_1$-$C_{10}$, $C_1$-$C_6$, $C_1$-$C_3$) alkoxy optionally substituted with from 1-10 (e.g., 1-5, 1-4, 1-3, 1-2, 1) $R^a$; $C_6$-$C_{18}$ (e.g., $C_6$-$C_{14}$, $C_6$-$C_{10}$, phenyl) aryloxy or heteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; $C_7$-$C_{20}$ (e.g., $C_7$-$C_{16}$, $C_7$-$C_{12}$, $C_7$-$C_{10}$) aralkoxy or heteroaralkoxy including 6-20 (e.g., 6-14, 6-12, 6-10) atoms, each of which is substituted with from 1-10 (e.g., 1-5, 1-4, 1-3, 1-2, 1) $R^c$; $C_6$-$C_{18}$ (e.g., $C_6$-$C_{14}$, $C_6$-$C_{10}$, phenyl) thioaryloxy or thioheteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; $C_7$-$C_{20}$ (e.g., $C_7$-$C_{16}$, $C_7$-$C_{12}$, $C_7$-$C_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_{20}$ (e.g., $C_1$-$C_{10}$, $C_1$-$C_6$, $C_1$-$C_3$) alkyl or $C_1$-$C_{20}$ (e.g., $C_1$-$C_{10}$, $C_1$-$C_6$, $C_1$-$C_3$) haloalkyl, each of which is optionally substituted with from 1-10 (e.g., 1-5, 1-4, 1-3, 1-2, 1) $R^a$; or (vi) $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$; or (vii) $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^{b'}$.

In certain embodiments, when $R^2$ is substituted with $R^b$, each $R^b$ can be, independently of one another:

(i) halo; $NO_2$; $NR^gR^h$; hydroxy; $C_1$-$C_{10}$ alkoxy optionally substituted with from 1-5 $R^a$; $C_6$-$C_{14}$ aryloxy or heteroaryloxy including 5-14 atoms, each of which is optionally substituted with from 1-10 $R^{b'}$; $C_7$-$C_{20}$ aralkoxy or heteroaralkoxy including 6-20 atoms, each of which is substituted with from 1-10 $R^c$; $C_6$-$C_{14}$ thioaryloxy or thioheteroaryloxy including 5-14 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_{10}$ alkyl or $C_1$-$C_{10}$ haloalkyl, each of which is optionally substituted with from 1-5 $R^a$; or (vi) $C_7$-$C_{16}$ aralkyl or heteroaralkyl including 6-16 atoms, each of which is optionally substituted with from 1-10 $R^c$; or (vii) $C_6$-$C_{14}$ aryl or heteroaryl including 5-14 atoms, each of which is optionally substituted with from 1-10 $R^{b'}$.

In certain embodiments, when $R^2$ is substituted with $R^b$, each $R^b$ can be, independently of one another:

(i) halo; $NO_2$; $NR^gR^h$; hydroxy; $C_1$-$C_6$ alkoxy optionally substituted with from 1-3 $R^a$; $C_6$-$C_{10}$ aryloxy or heteroaryloxy including 5-10 atoms, each of which is optionally substituted with from 1-5 $R^{b'}$; $C_7$-$C_{16}$ aralkoxy or heteroaralkoxy including 6-16 atoms, each of which is substituted with from 1-5 $R^c$; $C_6$-$C_{10}$ thioaryloxy or thioheteroaryloxy including 5-14 atoms, each of which is optionally substituted with from 1-5 $R^{b'}$; $C_7$-$C_{16}$ thioaralkoxy or thioheteroaralkoxy including 6-16 atoms, each of which is optionally substituted with from 1-5 $R^c$; cyano; —C(O)$NR^gR^h$; —C(O)$R^i$; —$NR^jC(O)R^i$; —$NR^jC(O)NR^gR^h$; or —S(O)$_nR^k$; or (ii) $C_1$-$C_6$ alkyl or $C_1$-$C_6$ haloalkyl, each of which is optionally substituted with from 1-3 $R^a$; or (vi) $C_7$-$C_{12}$ aralkyl or heteroaralkyl including 6-12 atoms, each of which is optionally substituted with from 1-5 $R^c$; or (vii) $C_6$-$C_{10}$ aryl or heteroaryl including 5-10 atoms, each of which is optionally substituted with from 1-5 $R^{b'}$.

In certain embodiments, when $R^2$ is substituted with $R^b$, each $R^b$ can be, independently of one another:

(i) halo; $NO_2$; $NR^gR^h$; hydroxy; $C_1$-$C_3$ alkoxy optionally substituted with from 1-2 $R^a$; $C_6$-aryloxy or heteroaryloxy including 5 or 6 atoms, each of which is optionally substituted with from 1-5 $R^{b'}$; $C_7$-$C_{12}$ aralkoxy or heteroaralkoxy including 6-12 atoms, each of which is substituted with from 1-5 R$^c$; C$_6$-thioaryloxy or thioheteroaryloxy including 5 or 6 atoms, each of which is optionally substituted with from 1-5 R$^{b'}$; C$_7$-C$_{12}$ thioaralkoxy or thioheteroaralkoxy including 6-12 atoms, each of which is optionally substituted with from 1-5 R$^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) C$_1$-C$_3$ alkyl or C$_1$-C$_3$ haloalkyl, each of which is optionally substituted with from 1-2 R$^a$; or (vi) C$_7$-C$_{10}$ aralkyl or heteroaralkyl including 6-20 atoms, each of which is optionally substituted with from 1-5 R$^c$; or (vii) phenyl or heteroaryl including 5 or 6 atoms, each of which is optionally substituted with from 1-5 R$^{b'}$.

A subset of compounds includes those in which R$^2$ has formula (II-A). In certain embodiments, R$^2$ can have formula (II-B):

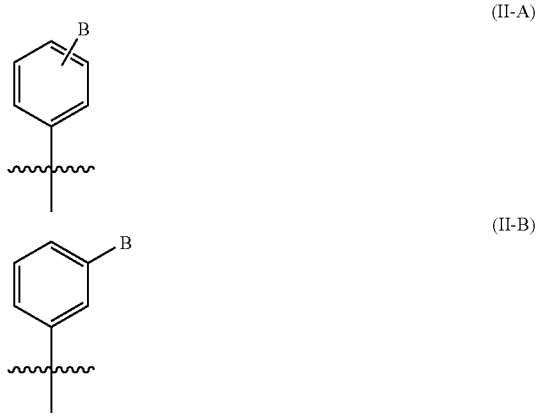

In some embodiments, B can be hydrogen (i.e., R$^2$ can be an unsubstituted phenyl group).

In some embodiments, B can be:

(i) halo; NO$_2$; NR$^g$R$^h$; hydroxy; C$_1$-C$_{20}$ (e.g., C$_1$-C$_{10}$, C$_1$-C$_6$, C$_1$-C$_3$) alkoxy optionally substituted with from 1-10 (e.g., 1-5, 1-4, 1-3, 1-2, 1) R$^a$; C$_6$-C$_{18}$ (e.g., C$_6$-C$_{14}$, C$_6$-C$_{10}$, phenyl) aryloxy or heteroaryloxy including 5-16 (e.g., 5-14, 5-10, 5-6) atoms, each of which is optionally substituted with from 1-10 (e.g., 1-5, 1-4, 1-3, 1-2, 1) R$^{b'}$; C$_7$-C$_{20}$ (e.g., C$_7$-C$_{16}$, C$_7$-C$_{12}$, C$_7$-C$_{10}$) aralkoxy or heteroaralkoxy including 6-20 (e.g., 6-14, 6-12, 6-10) atoms, each of which is substituted with from 1-10 (e.g., 1-5, 1-4, 1-3, 1-2, 1) R$^c$; C$_6$-C$_{18}$ (e.g., C$_6$-C$_{14}$, C$_6$-C$_{10}$, phenyl) thioaryloxy or thioheteroaryloxy including 5-16 (e.g., 5-14, 5-10, 5-6) atoms, each of which is optionally substituted with from 1-10 (e.g., 1-5, 1-4, 1-3, 1-2, 1) R$^{b'}$; C$_7$-C$_{20}$ (e.g., C$_7$-C$_{16}$, C$_7$-C$_{12}$, C$_7$-C$_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) R$^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) C$_1$-C$_{20}$ (e.g., C$_1$-C$_{10}$, C$_1$-C$_6$, C$_1$-C$_3$) alkyl or C$_1$-C$_{20}$ (e.g., C$_1$-C$_{10}$, C$_1$-C$_6$, C$_1$-C$_3$) haloalkyl, each of which is optionally substituted with from 1-10 (e.g., 1-5, 1-4, 1-3, 1-2, 1) R$^a$; or (vi) C$_7$-C$_{20}$ (e.g., C$_7$-C$_{16}$, C$_7$-C$_{12}$, C$_7$-C$_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) R$^c$; or (vii) C$_6$-C$_{18}$ (e.g., C$_6$-C$_{14}$, C$_6$-C$_{10}$, phenyl) aryl or heteroaryl including 5-16 (e.g., 5-14, 5-10, 5-6) atoms, each of which is optionally substituted with from 1-10 (e.g., 1-5, 14, 1-3, 1-2, 1) R$^{b'}$.

In certain embodiments, B can be:

(i) halo; NO$_2$; NR$^g$R$^h$; hydroxy; C$_1$-C$_{10}$ (e.g., C$_1$-C$_6$, C$_1$-C$_3$) alkoxy optionally substituted with from 1-5 (e.g., 1-4, 1-3, 1-2, 1) R$^a$; C$_6$-C$_{14}$ (e.g., C$_6$-C$_{10}$, phenyl) aryloxy or heteroaryloxy including 5-14 (e.g., 5-10, 5-6) atoms, each of which is optionally substituted with from 1-10 (e.g., 1-5, 1-4, 1-3, 1-2, 1) R$^{b'}$; C$_7$-C$_{20}$ (e.g., C$_7$-C$_{16}$, C$_7$-C$_{12}$, C$_7$-C$_{10}$) aralkoxy or heteroaralkoxy including 6-20 (e.g., 6-14, 6-12, 6-10) atoms, each of which is substituted with from 1-10 (e.g., 1-5, 1-4, 1-3, 1-2, 1) R$^c$; C$_6$-C$_{14}$ (e.g., C$_6$-C$_{10}$, phenyl) thioaryloxy or thioheteroaryloxy including 5-14 (e.g., 5-10, 5-6) atoms, each of which is optionally substituted with from 1-10 (e.g., 1-5, 1-4, 1-3, 1-2, 1) R$^{b'}$; C$_7$-C$_{20}$ (e.g., C$_7$-C$_{16}$, C$_7$-C$_{12}$, C$_7$-C$_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) R$^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) C$_1$-C$_{10}$ (e.g., C$_1$-C$_6$, C$_1$-C$_3$) alkyl or C$_1$-C$_{10}$ (e.g., C$_1$-C$_6$, C$_1$-C$_3$) haloalkyl, each of which is optionally substituted with from 1-5 (e.g., 1-4, 1-3, 1-2, 1) R$^a$; or (vi) C$_7$-C$_{16}$ (e.g., C$_7$-C$_{12}$, C$_7$-C$_{10}$) aralkyl or heteroaralkyl including 6-16 (e.g., 6-14, 6-12, 6-10) atoms, each of which is optionally substituted with from 1-10 (e.g., 1-5, 1-4, 1-3, 1-2, 1) R$^c$; or (vii) C$_6$-C$_{14}$ (e.g., C$_6$-C$_{10}$, phenyl) aryl or heteroaryl including 5-14 atoms, each of which is optionally substituted with from 1-10 (e.g., 1-5, 1-4, 1-3, 1-2, 1) R$^{b'}$.

In certain embodiments, B can be:

(i) halo; NO$_2$; NR$^g$R$^h$; hydroxy; C$_1$-C$_6$ alkoxy optionally substituted with from 1-3 R$^a$; C$_6$-C$_{10}$ aryloxy or heteroaryloxy including 5-10 atoms, each of which is optionally substituted with from 1-5 R$^{b'}$; C$_7$-C$_{16}$ aralkoxy or heteroaralkoxy including 6-16 atoms, each of which is substituted with from 1-5 R$^c$; C$_6$-C$_{10}$ thioaryloxy or thioheteroaryloxy including 5-14 atoms, each of which is optionally substituted with from 1-5 R$^{b'}$; C$_7$-C$_{16}$ thioaralkoxy or thioheteroaralkoxy including 6-16 atoms, each of which is optionally substituted with from 1-5 R$^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) C$_1$-C$_6$ alkyl or C$_1$-C$_6$ haloalkyl, each of which is optionally substituted with from 1-3 R$^a$; or (vi) C$_7$-C$_{12}$ aralkyl or heteroaralkyl including 6-12 atoms, each of which is optionally substituted with from 1-5 R$^c$; or (vii) C$_6$-C$_{10}$ aryl or heteroaryl including 5-10 atoms, each of which is optionally substituted with from 1-5 R$^{b'}$.

In certain embodiments, B can be:

(i) halo; NO$_2$; NR$^g$R$^h$; hydroxy; C$_1$-C$_3$ alkoxy optionally substituted with from 1-2 R$^a$; C$_6$-aryloxy or heteroaryloxy including 5 or 6 atoms, each of which is optionally substituted with from 1-5 R$^{b'}$; C$_7$-C$_{12}$ aralkoxy or heteroaralkoxy including 6-12 atoms, each of which is substituted with from 1-5 R$^c$; C$_6$-thioaryloxy or thioheteroaryloxy including 5 or 6 atoms, each of which is optionally substituted with from 1-5 R$^{b'}$; C$_7$-C$_{12}$ thioaralkoxy or thioheteroaralkoxy including 6-12 atoms, each of which is optionally substituted with from 1-5 R$^c$; cyano; —C(O)NR$^g$R$^h$; —C(O)R$^i$; —NR$^j$C(O)R$^i$; —NR$^j$C(O)NR$^g$R$^h$; or —S(O)$_n$R$^k$; or (ii) C$_1$-C$_3$ alkyl or C$_1$-C$_3$ haloalkyl, each of which is optionally substituted with from 1-2 R$^a$; or (vi) C$_7$-C$_{10}$ aralkyl or heteroaralkyl including 6-20 atoms, each of which is optionally substituted with from 1-5 R$^c$; or (vii) phenyl or heteroaryl including 5 or 6 atoms, each of which is optionally substituted with from 1-5 $R^{b'}$.

In some embodiments, B can be hydroxy.

In some embodiments, B can be $NH_2$.

In some embodiments, B can be $-NR^jC(O)NR^gR^h$.

In certain embodiments, $R^j$ can be hydrogen or $C_1$-$C_6$ alkyl (e.g., $C_1$-$C_3$ alkyl). In certain embodiments, $R^j$ can be hydrogen.

In certain embodiments, one of $R^g$ and $R^h$ can be hydrogen, and the other can be $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$; or $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^b$.

When B is $-NR^jC(O)NR^gR^h$, B can have formula (III):

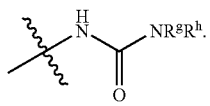

(III)

In certain embodiments, one of $R^g$ and $R^h$ can be hydrogen, and the other can be $C_7$-$C_{20}$ (e.g., $C_7$-$C_{16}$, $C_7$-$C_{12}$, $C_7$-$C_{10}$) aralkyl optionally substituted with from 1-10 (e.g., 1-5, 1-4, 1-3, 1-2, 1) $R^c$; or $C_6$-$C_{18}$ (e.g., $C_6$-$C_{14}$, $C_6$-$C_{10}$, phenyl) aryl optionally substituted with from 1-10 $R^b$.

In certain embodiments, one of $R^g$ and $R^h$ can be hydrogen, and the other can be $C_6$-$C_{18}$ (e.g., $C_6$-$C_{14}$, $C_6$-$C_{10}$, phenyl) aryl optionally substituted with from 1-10 (e.g., 1-5, 1-4, 1-3, 1-2, 1) $R^b$.

In certain embodiments, one of $R^g$ and $R^h$ can be hydrogen, and the other can be $C_6$-$C_{10}$ aryl optionally substituted with from 1-5 (e.g., 1-4, 1-3, 1-2, 1) $R^b$.

In certain embodiments, one of $R^g$ and $R^h$ can be hydrogen, and the other can be unsubstituted phenyl.

In certain embodiments, one of $R^g$ and $R^h$ can be hydrogen, and the other can be phenyl substituted with from 1-5 (e.g., 1-4, 1-3, 1-2, 1) $R^b$.

In certain embodiments, each $R^b$ can be, independently of one another, halo; $NO_2$; hydroxy; $C_1$-$C_{10}$ (e.g., $C_1$-$C_6$, $C_1$-$C_3$) alkoxy; cyano; $-C(O)R^i$; $C_1$-$C_{10}$ (e.g., $C_1$-$C_6$, $C_1$-$C_3$) alkyl; or $C_1$-$C_{10}$ (e.g., $C_1$-$C_6$, $C_1$-$C_3$) haloalkyl.

In certain embodiments, each $R^b$ can be, independently of one another, halo; $NO_2$; hydroxy; $C_1$-$C_6$ alkoxy; cyano; $-C(O)R^i$; $C_1$-$C_6$ alkyl; or $C_1$-$C_6$ haloalkyl.

In certain embodiments, each $R^b$ can be, independently of one another, halo; $NO_2$; hydroxy; $C_1$-$C_3$ alkoxy; cyano; $-C(O)R^i$; $C_1$-$C_3$ alkyl; or $C_1$-$C_3$ haloalkyl (e.g., $C_1$-$C_3$ haloalkyl having 1, 2, 3, 4, or 5 halogens (e.g., fluoro) or $C_1$-$C_3$ perhaloalkyl (e.g., $C_1$-$C_3$ perfluoroalkyl).

In some embodiments, B can be:

(i-B) $NR^gR^h$, wherein one of $R^g$ and $R^h$ is hydrogen, and the other is $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$; or $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^b$; or (ii-B) $C_6$-$C_{18}$ (e.g., $C_6$-$C_{14}$, $C_6$-$C_{10}$, phenyl) aryloxy or heteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; or $C_7$-$C_{20}$ (e.g., $C_7$-$C_{16}$, $C_7$-$C_{12}$, $C_7$-$C_{10}$) aralkoxy or heteroaralkoxy including 6-20 (e.g., 6-14, 6-12, 6-10) atoms, each of which is optionally substituted with from 1-10 (e.g., 1-5, 1-4, 1-3, 1-2, 1) $R^c$; or (iii-B) $C_6$-$C_{18}$ (e.g., $C_6$-$C_{14}$, $C_6$-$C_{10}$, phenyl) thioaryloxy or thioheteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; or $C_7$-$C_{20}$ (e.g., $C_7$-$C_{16}$, $C_7$-$C_{12}$, $C_7$-$C_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) $R^c$; or (vi-B) $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^{b'}$; or $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$.

In certain embodiments, B can be:

(i-B') $NR^gR^h$ wherein one of $R^g$ and $R^h$ is hydrogen, and the other is $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$;

(ii-B') $C_7$-$C_{20}$ (e.g., $C_7$-$C_{16}$, $C_7$-$C_{12}$, $C_7$-$C_{10}$) aralkoxy or heteroaralkoxy including 6-20 (e.g., 6-14, 6-12, 6-10) atoms, each of which is optionally substituted with from 1-10 (e.g., 1-5, 1-4, 1-3, 1-2, 1) $R^c$; or (iii-B') $C_7$-$C_{20}$ (e.g., $C_7$-$C_{16}$, $C_7$-$C_{12}$, $C_7$-$C_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) $R^c$; or (iv-B') $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$.

In these embodiments (i.e., when B is as described in (i-B), (ii-B), (iii-B), (iv-B), (i-B'), (ii-B'), (iii-B'), (iv-B')), B can be unsubstituted or substituted. When B is substituted, each $R^b$, $R^{b'}$, and $R^c$ can be, independently of one another, halo; $NO_2$; hydroxy; $C_1$-$C_{10}$ (e.g., $C_1$-$C_6$, $C_1$-$C_3$) alkoxy; $C_1$-$C_{10}$ (e.g., $C_1$-$C_6$, $C_1$-$C_3$) haloalkoxy; cyano; $-C(O)R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or $-C(O)OR^i$.

In certain embodiments, each $R^b$, $R^{b'}$, and $R^c$ can be, independently of one another, halo; $NO_2$; hydroxy; $C_1$-$C_6$ alkoxy; $C_1$-$C_6$ haloalkoxy; cyano; $-C(O)R^i$; $C_1$-$C_6$ alkyl or $C_1$-$C_6$ haloalkyl, each of which is optionally substituted with from 1-3 $R^a$; or $-C(O)OR^i$.

In certain embodiments, each $R^b$, $R^{b'}$, and $R^c$ can be, independently of one another, halo; $NO_2$; hydroxy; $C_1$-$C_3$ alkoxy; $C_1$-$C_3$ haloalkoxy; cyano; $-C(O)R^i$ (e.g., $-C(O)$(heterocyclyl including 3-20 atoms); $C_1$-$C_4$ alkyl or $C_1$-$C_4$ haloalkyl (e.g., $C_1$-$C_4$ perhaloalkyl, e.g., $C_1$-$C_4$ perfluoroalkyl), each of which is optionally substituted with from 1-2 $R^a$ (e.g., $-C(O)OH$ or $-C(O)OCH_3$); or $-C(O)OR^i$.

In certain embodiments, each $R^b$, $R^{b'}$, and $R^c$ can be, independently of one another, F; Cl; Br; OH; $OCH_3$; $OCF_3$; $-C(O)$(morpholino); $CH_3$; $CH_3$ substituted with from 1-2 $R^a$ (e.g., $-C(O)OH$ or $-C(O)OCH_3$); $CF_3$; $-C(O)OH$; or $-C(O)OCH_3$.

In certain embodiments, when B is as described in (i-B), (ii-B), (iii-B), (iv-B), (i-B'), (ii-B'), (iii-B'), (iv-B'), B can have formula (IV):

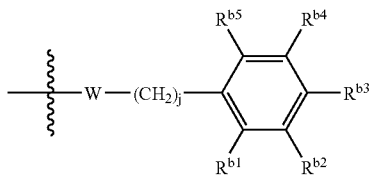

in which W can be $NR^j$, O, S, or is absent;

j can be 0, 1, 2, 3, 4, or 5; and each $R^{b1}$, $R^{b2}$, $R^{b3}$, $R^{b4}$, and $R^{b5}$ can be, independently of one another, hydrogen, halo; $NO_2$; hydroxy; $C_1$-$C_{10}$ (e.g., $C_1$-$C_6$, $C_1$-$C_3$) alkoxy; $C_1$-$C_{10}$ (e.g., $C_1$-$C_6$, $C_1$-$C_3$) haloalkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$.

In certain embodiments, W can be $NR^j$, O, or S. In certain embodiments, $R^j$ can be hydrogen or $C_1$-$C_6$ alkyl (e.g., $C_1$-$C_3$ alkyl). In certain embodiments, $R^j$ can be hydrogen, and W is NH.

In certain embodiments, j can be 0 or 1. In certain embodiments, j can be 1.

In certain embodiments, each of $R^{b1}$, $R^{b2}$, $R^{b3}$, $R^{b4}$, and $R^{b5}$ can be hydrogen.

In certain embodiments, each of $R^{b1}$, $R^{b2}$, $R^{b3}$, $R^{b4}$, and $R^{b5}$ can be, independently of one another, hydrogen; halo; $NO_2$; hydroxy; $C_1$-$C_6$ alkoxy; $C_1$-$C_6$ haloalkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$.

In certain embodiments, each of $R^{b1}$, $R^{b2}$, $R^{b3}$, $R^{b4}$, and $R^{b5}$ can be, independently of one another, hydrogen; halo; $NO_2$; hydroxy; $C_1$-$C_3$ alkoxy; $C_1$-$C_3$ haloalkoxy; cyano; —C(O)$R^i$ (e.g., —C(O)(heterocyclyl including 3-20 atoms); $C_1$-$C_4$ alkyl or $C_1$-$C_4$ haloalkyl (e.g., $C_1$-$C_4$ perhaloalkyl, e.g., $C_1$-$C_4$ perfluoroalkyl), each of which is optionally substituted with from 1-2 $R^a$ (e.g., —C(O)OH or —C(O)OCH$_3$); or —C(O)O$R^i$.

In certain embodiments, each of $R^{b1}$, $R^{b2}$, $R^{b3}$, $R^{b4}$, and $R^{b5}$ can be, independently of one another, hydrogen; F; Cl; Br; OH; OCH$_3$; OCF$_3$; —C(O)(morpholino); CH$_3$; CH$_3$ substituted with from 1-2 $R^a$ (e.g., —C(O)OH or —C(O)OCH$_3$); CF$_3$; —C(O)OH; or —C(O)OCH$_3$.

In certain embodiments, any 1, 2, 3, or 4 of $R^{b1}$, $R^{b2}$, $R^{b3}$, $R^{b4}$, and $R^{b5}$ can be, independently of one another, halo; $NO_2$; hydroxy; $C_1$-$C_{10}$ (e.g., $C_1$-$C_6$, $C_1$-$C_3$) alkoxy; $C_1$-$C_{10}$ (e.g., $C_1$-$C_6$, $C_1$-$C_3$) haloalkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$; and the other(s) can be hydrogen.

In certain embodiments, any 1, 2, 3, or 4 of $R^{b1}$, $R^{b2}$, $R^{b3}$, $R^{b4}$, and $R^{b5}$ can be, independently of one another, halo; $NO_2$; hydroxy; $C_1$-$C_6$ alkoxy; $C_1$-$C_6$ haloalkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$; and the other(s) can be hydrogen.

In certain embodiments, any 1, 2, 3, or 4 of $R^{b1}$, $R^{b2}$, $R^{b3}$, $R^{b4}$, or $R^{b5}$ can be, independently of one another, halo; $NO_2$; hydroxy; $C_1$-$C_3$ alkoxy; $C_1$-$C_3$ haloalkoxy; cyano; —C(O)$R^i$ (e.g., —C(O)(heterocyclyl including 3-20 atoms); $C_1$-$C_4$ alkyl or $C_1$-$C_4$ haloalkyl (e.g., $C_1$-$C_4$ perhaloalkyl, e.g., $C_1$-$C_4$ perfluoroalkyl), each of which is optionally substituted with from 1-2 $R^a$ (e.g., —C(O)OH or —C(O)OCH$_3$); or —C(O)O$R^i$; and the other(s) can be hydrogen.

In certain embodiments, any 1, 2, 3, or 4 of $R^{b1}$, $R^{b2}$, $R^{b3}$, $R^{b4}$, or $R^{b5}$ can be, independently of one another, F; Cl; Br; OH; OCH$_3$; OCF$_3$; —C(O)(morpholino); CH$_3$; CH$_3$ substituted with from 1-2 $R^a$ (e.g., —C(O)OH or —C(O)OCH$_3$); CF$_3$; —C(O)OH; or —C(O)OCH$_3$; and the other(s) can be hydrogen.

In certain embodiments, each of $R^{b1}$, $R^{b2}$, $R^{b3}$, $R^{b4}$, and $R^{b5}$ can be other than hydrogen.

In certain embodiments, any one of $R^{b1}$, $R^{b2}$, $R^{b3}$, $R^{b4}$, or $R^{b5}$ (e.g., $R^{b1}$ or $R^{b5}$; $R^{b2}$ or $R^{b4}$; or $R^{b3}$) can be halo; $NO_2$; hydroxy; $C_1$-$C_{10}$ (e.g., $C_1$-$C_6$, $C_1$-$C_3$) alkoxy; $C_1$-$C_{10}$ (e.g., $C_1$-$C_6$, $C_1$-$C_3$) haloalkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$; and the other four can be hydrogen.

In certain embodiments, any one of $R^{b1}$, $R^{b2}$, $R^{b3}$, $R^{b4}$, or $R^{b5}$ (e.g., $R^{b1}$ or $R^{b5}$; $R^{b2}$ or $R^{b4}$; or $R^{b3}$) can be halo; $NO_2$; hydroxy; $C_1$-$C_6$ alkoxy; $C_1$-$C_6$ haloalkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$; and the other four can be hydrogen.

In certain embodiments, any one of $R^{b1}$, $R^{b2}$, $R^{b3}$, $R^{b4}$, or $R^{b5}$ (e.g., $R^{b1}$ or $R^{b5}$; $R^{b2}$ or $R^{b4}$; or $R^{b3}$) can be halo; $NO_2$; hydroxy; $C_1$-$C_3$ alkoxy; $C_1$-$C_3$ haloalkoxy; cyano; —C(O)$R^i$ (e.g., —C(O)(heterocyclyl including 3-20 atoms); $C_1$-$C_4$ alkyl or $C_1$-$C_4$ haloalkyl (e.g., $C_1$-$C_4$ perhaloalkyl, e.g., $C_1$-$C_4$ perfluoroalkyl), each of which is optionally substituted with from 1-2 $R^a$ (e.g., —C(O)OH or —C(O)OCH$_3$); or —C(O)O$R^i$; and the other four can be hydrogen.

In certain embodiments, any one of $R^{b1}$, $R^{b2}$, $R^{b3}$, $R^{b4}$, or $R^{b5}$ ($R^{b1}$ or $R^{b5}$; $R^{b2}$ or $R^{b4}$; or $R^{b3}$) can be F; Cl; Br; OH; OCH$_3$; OCF$_3$; —C(O)(morpholino); CH$_3$; CH$_3$ substituted with from 1-2 $R^a$ (e.g., —C(O)OH or —C(O)OCH$_3$); CF$_3$; —C(O)OH; or —C(O)OCH$_3$; and the other four can be hydrogen.

In certain embodiments, $R^{b3}$ can be $C_1$-$C_4$ alkyl substituted with 1 $R^a$, and each of $R^{b1}$, $R^{b2}$, $R^{b4}$, and $R^{b5}$ can be hydrogen. In certain embodiments, $R^a$ can be C(O)O$R^i$, in which $R^i$ can be hydrogen or $C_1$-$C_4$ alkyl (e.g., CH$_3$). In certain embodiments, $R^{b3}$ can be —CH$_2$C(O)OH, —CH$_2$C(O)OCH$_3$, —C(CH$_3$)$_2$C(O)OH, or —C(CH$_3$)$_2$C(O)OCH$_3$. In certain embodiments, $R^{b3}$ can be —C(O)O$R^i$ (e.g., COOH).

In certain embodiments, $R^{b2}$ can be $C_1$-$C_4$ haloalkyl (e.g., $C_1$-$C_4$ perhaloalkyl, e.g., $C_1$-$C_4$ perfluoroalkyl, e.g., CF$_3$); or —C(O)$R^i$ (e.g., —C(O)(heterocyclyl including 3-20 atoms), e.g., —C(O)(morpholino)); or —C(O)O$R^i$ (e.g., COOH); and each of $R^{b1}$, $R^{b3}$, $R^{b4}$, and $R^{b5}$ can be hydrogen.

In certain embodiments, $R^{b1}$ can be halo (e.g., Cl) or $C_1$-$C_6$ haloalkoxy (e.g., OCF$_3$), and each of $R^{b1}$, $R^{b2}$, $R^{b4}$, and $R^{b5}$ can be hydrogen.

In certain embodiments, any two of $R^{b1}$, $R^{b2}$, $R^{b3}$, $R^{b4}$, or $R^{b5}$ ($R^{b1}$ and $R^{b2}$; $R^{b1}$ and $R^{b3}$; $R^{b1}$ and $R^{b4}$; $R^{b1}$ and $R^{b5}$; $R^{b2}$ and $R^{b3}$; $R^{12}$ and $R^{b1}$; $R^{b2}$ and $R^{b5}$; etc., e.g., $R^{b1}$ and $R^{b2}$; $R^{b1}$ and $R^{b4}$; or $R^{b2}$ and $R^{b3}$) can be, independently of one another, halo; $NO_2$; hydroxy; $C_1$-$C_{10}$ (e.g., $C_1$-$C_6$, $C_1$-$C_3$) alkoxy; $C_1$-$C_{10}$ (e.g., $C_1$-$C_6$, $C_1$-$C_3$) haloalkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$; and the other three can be hydrogen.

In certain embodiments, any two of $R^{b1}$, $R^{b2}$, $R^{b3}$, $R^{b4}$, or $R^{b5}$ ($R^{b1}$ and $R^{b2}$; $R^{b1}$ and $R^{b2}$; $R^{b1}$ and $R^{b4}$; $R^{b1}$ and $R^{b5}$; $R^{b2}$ and $R^{b3}$; $R^{b2}$ and $R^{b4}$; $R^{b2}$ and $R^{b5}$; etc., e.g., $R^{b1}$ bland $R^{b2}$; $R^{b1}$ and $R^{b4}$; or $R^{b2}$ and $R^{b3}$) can be, independently of one another, halo; $NO_2$; hydroxy; $C_1$-$C_6$ alkoxy; $C_1$-$C_6$ haloalkoxy; cyano; —C(O)$R^i$; $C_1$-$C_6$ alkyl or $C_1$-$C_6$ haloalkyl, each of which is optionally substituted with from 1-3 $R^a$; or —C(O)O$R^i$; and the other(s) can be hydrogen.

In certain embodiments, any two of $R^{b1}$, $R^{b2}$, $R^{b3}$, $R^{b4}$ or $R^{b5}$ ($R^{b1}$ and $R^{b2}$; $R^{b1}$ and $R^{b3}$; $R^{b1}$ and $R^{b4}$; $R^{b1}$ and $R^{b5}$; $R^{b2}$ and $R^{b3}$; $R^{b2}$ and $R^{b4}$; $R^{b2}$ and $R^{b5}$; etc., e.g., $R^{b1}$ band $R^{b2}$; $R^{b1}$ and $R^{b4}$; or $R^{b2}$ and $R^{b3}$) can be, independently of one another, halo; $NO_2$; hydroxy; $C_1$-$C_3$ alkoxy; $C_1$-$C_3$ haloalkoxy; cyano; —C(O)$R^i$ (e.g., —C(O)(heterocyclyl including 3-20 atoms); $C_1$-$C_4$ alkyl or $C_1$-$C_4$ haloalkyl (e.g., $C_1$-$C_4$ perhaloalkyl, e.g., $C_1$-$C_4$ perfluoroalkyl), each of which is optionally substituted with from 1-2 $R^a$ (e.g., —C(O)OH or —C(O)O$CH_3$); or —C(O)O$R^i$; and the other(s) can be hydrogen.

In certain embodiments, any two of $R^{b1}$, $R^{b2}$, $R^{b3}$, $R^{b4}$, or $R^{b5}$ ($R^{b1}$ and $R^{b2}$; $R^{b1}$ and $R^{b2}$; $R^{b1}$ and $R^{b4}$; $R^{b1}$ and $R^{b4}$; $R^{b2}$ and $R^{b3}$; $R^{b2}$ and $R^{b4}$; $R^{b2}$ and $R^{b5}$; etc., e.g., $R^{b1}$ and $R^{b2}$; $R^{b1}$ and $R^{b4}$; or $R^{b2}$ and $R^{b3}$) can be, independently of one another, F; Cl; Br; OH; O$CH_3$; O$CF_3$; —C(O)(morpholino); $CH_3$; $CH_3$ substituted with from 1-2 $R^a$ (e.g., —C(O)OH or —C(O)O$CH_3$); $CF_3$; —C(O)OH; or —C(O)O$CH_3$; and the other(s) can be hydrogen.

In certain embodiments, $R^{b1}$ and $R^{b4}$ can both be $C_1$-$C_4$ alkyl (e.g., $CH_3$), and each of $R^{b2}$, $R^{b3}$, and $R^{b5}$ can be hydrogen.

In certain embodiments, $R^{b1}$ can be $C_1$-$C_4$ haloalkyl (e.g., $CF_3$), $R^{b4}$ can be halo (e.g., F, Cl), and each of $R^{b2}$, $R^{b3}$, and $R^{b5}$ can be hydrogen.

In certain embodiments, $R^{b1}$ and $R^{b4}$ can both be $C_1$-$C_4$ haloalkyl (e.g., $CF_3$), and each of $R^{b2}$, $R^{b3}$, and $R^{b5}$ can be hydrogen.

In certain embodiments, $R^{b1}$ can be halo (e.g., F, Br); $R^{b4}$ can be $C_1$-$C_4$ alkyl (e.g., $CH_3$), or $C_1$-$C_4$ haloalkyl (e.g., $CF_3$), or $C_1$-$C_3$ alkoxy (e.g., O$CH_3$), or halo (e.g., Br); and each of $R^{b2}$, $R^{b3}$, and $R^{b5}$ can be hydrogen.

In certain embodiments, $R^{b1}$ can be $C_1$-$C_3$ alkoxy (e.g., O$CH_3$), $R^{b4}$ can be halo (e.g., Br), and each of $R^{b2}$, $R^{b3}$, and $R^{b5}$ can be hydrogen.

In certain embodiments, $R^{b1}$ and $R^{b2}$ can both be $C_1$-$C_4$ alkyl (e.g., $CH_3$), and each of $R^{b3}$, $R^{b4}$, and $R^{b5}$ can be hydrogen.

In certain embodiments, $R^{b1}$ can be halo (e.g., F, Cl), $R^{b2}$ can be $C_1$-$C_4$ haloalkyl (e.g., $CF_3$), and each of $R^{b3}$, $R^{b4}$, and $R^{b5}$ can be hydrogen.

In certain embodiments, $R^{b2}$ and $R^{b3}$ can both be halo (e.g., Cl), and each of $R^{b1}$, $R^{b4}$, and $R^{b5}$ can be hydrogen.

In certain embodiments, $R^{b2}$ can be halo (e.g., F, Cl), $R^{b3}$ can be $C_1$-$C_4$ haloalkyl (e.g., $CF_3$), and each of $R^{b1}$, $R^{14}$, and $R^{b5}$ can be hydrogen.

In certain embodiments, $R^{b2}$ and $R^{b3}$ can each be, independently, $C_1$-$C_6$ alkoxy (e.g., O$CH_3$) or —C(O)O$R^i$ (e.g., COOH); and each of $R^{b1}$, $R^{b4}$, and $R^{b5}$ can be hydrogen.

In certain embodiments, $R^{b1}$ and $R^{b5}$ can both be halo (e.g., chloro), and each of $R^{b2}$, $R^{b3}$, and $R^{b4}$ can be hydrogen.

In certain embodiments, $R^{b1}$ can be halo (e.g., chloro), $R^{b3}$ can be —C(O)O$R^i$ (e.g., COOH), and each of $R^{b2}$, $R^{b4}$, and $R^{b5}$ can be hydrogen.

When B is as described in (i-B), (ii-B), (iii-B), (iv-B), (i-B'), (ii-B'), (iii-B'), (iv-B')), B can also be W—($CH_2$)$_j$-(bicyclic or tricyclic aryl) or W—($CH_2$)$_j$-(heteroaryl), in which W and j can be as described elsewhere for Formula (IV).

B can be —NH—$CH_2$-naphthyl (e.g., the methylene group can be attached to the 1 or 2 position of the naphthyl ring, and the naphthyl ring can optionally be substituted in one or more positions, e.g., with 1-5, 1-4, 1-3, 1-2, or 1 $R^c$).

In certain embodiments, B can be —NH—$CH_2$-indolyl or —O—$CH_2$-indolyl (e.g., the methylene group can be attached to the 2 or 7 position of the indole ring, and the indole ring can be optionally substituted in one or more positions, e.g., with 1-5, 1-4, 1-3, 1-2, or 1 $R^c$, e.g., at the 1-position with $CH_3$ and/or at the 5-position with halo (e.g., fluoro) and/or at the 3-position with COO$R^i$ (e.g., COOH).

In certain embodiments, B can be —NH—$CH_2$-benzothienyl (e.g., the methylene group can be attached to the 2 or 3 position of the benzothienyl ring, and the benzothienyl ring can be optionally substituted in one or more positions, e.g., with 1-5, 1-4, 1-3, 1-2, or 1 $R^c$, e.g., at the 3-position with $C_1$-$C_6$ alkyl (e.g., $CH_3$) or at the 4-position with $C_1$-$C_4$ haloalkyl (e.g., $CF_3$)).

In some embodiments, B can be —C(O)N$R^g R^h$; —C(O)$R^i$; —N$R^j$C(O)$R^i$; —N$R^j$C(O)N$R^g R^h$; or —S(O)$_n R^k$.

In certain embodiments, $R^j$ can be hydrogen or $C_1$-$C_6$ alkyl (e.g., $C_1$-$C_3$ alkyl). In certain embodiments, $R^j$ can be hydrogen.

In certain embodiments, each of $R^i$ and $R^k$ can be, independently of one another, $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^{b'}$; or $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$. In certain embodiments, $R^{b'}$ and $R^c$ can each be, independently of one another, halo; $NO_2$; hydroxy; $C_1$-$C_{10}$ (e.g., $C_1$-$C_6$, $C_1$-$C_3$) alkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$.

In certain embodiments, each of $R^j$ and $R^k$ can be, independently of one another, $C_6$-$C_{18}$ (e.g., $C_6$-$C_{14}$, $C_6$-$C_{10}$, phenyl) aryl optionally substituted with from 1-10 (e.g., 1-5, 1-4, 1-3, 1-2, 1) $R^{b'}$; or $C_7$-$C_{20}$ (e.g., $C_7$-$C_{16}$, $C_7$-$C_{12}$, $C_7$-$C_{10}$) aralkyl optionally substituted with from 1-10 (e.g., 1-5, 1-4, 1-3, 1-2, 1) $R^c$. In certain embodiments, $R^{b'}$ and $R^c$ can each be, independently of one another, halo; $NO_2$; hydroxy; $C_1$-$C_{10}$ (e.g., $C_1$-$C_6$, $C_1$-$C_3$) alkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$.

In certain embodiments, one of $R^g$ or $R^h$ can be hydrogen, and the other can be $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^{b'}$; or $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$. In certain embodiments, $R^{b'}$ and $R^c$ can each be, independently of one another, halo; $NO_2$; hydroxy; $C_1$-$C_{10}$ (e.g., $C_1$-$C_6$, $C_1$-$C_3$) alkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$.

In certain embodiments, one of $R^g$ or $R^h$ can be hydrogen, and the other can be $C_6$-$C_{18}$ (e.g., $C_6$-$C_{14}$, $C_6$-$C_{10}$, phenyl) aryl optionally substituted with from 1-10 (e.g., 1-5, 1-4, 1-3, 1-2, 1) $R^{b'}$; or $C_7$-$C_{20}$ (e.g., $C_7$-$C_{16}$, $C_7$-$C_{12}$, $C_7$-$C_{10}$) aralkyl optionally substituted with from 1-10 (e.g., 1-5, 1-4, 1-3, 1-2, 1) $R^c$. In certain embodiments, $R^{b'}$ and $R^c$ can each be, independently of one another, halo; $NO_2$; hydroxy; $C_1$-$C_{10}$ (e.g., $C_1$-$C_6$, $C_1$-$C_3$) alkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)O$R^i$.

In some embodiments, B can be $C_1$-$C_{20}$ (e.g., $C_1$-$C_{10}$, $C_1$-$C_6$, $C_1$-$C_3$) alkyl or $C_1$-$C_{20}$ (e.g., $C_1$-$C_{10}$, $C_1$-$C_6$, $C_1$-$C_3$) haloalkyl, each of which is optionally substituted with from 1-10 (e.g., 1-5, 1-4, 1-3, 1-2, 1) $R^a$.

In certain embodiments, B can be $C_1$-$C_{20}$ (e.g., $C_1$-$C_{10}$, $C_1$-$C_6$, $C_1$-$C_3$) alkyl optionally substituted with from 1-10 (e.g., 1-5, 1-4, 1-3, 1-2, 1) $R^a$.

In certain embodiments, B can be $C_1$-$C_{20}$ (e.g., $C_1$-$C_{10}$, $C_1$-$C_6$, $C_1$-$C_3$) alkyl substituted with from 1-10 (e.g., 1-5, 1-4, 1-3, 1-2, 1) $R^a$.

In certain embodiments, B can be $C_1$-$C_{10}$ (e.g., $C_1$-$C_6$, $C_1$-$C_3$) alkyl substituted with from 1-5 (e.g., 1-4, 1-3, 1-2, 1) $R^a$.

In certain embodiments, B can be $C_1$-$C_6$ (e.g., $C_1$-$C_3$) alkyl optionally substituted with from 1-3 (e.g., 1-2, 1) $R^a$.

In certain embodiments, B can be $C_1$-$C_3$ alkyl optionally substituted with from 1-2 (e.g., 1) $R^a$.

When B is $C_1$-$C_{20}$ (e.g., $C_1$-$C_{10}$, $C_1$-$C_6$, $C_1$-$C_3$) alkyl substituted with from 1-10 (e.g., 1-5, 1-4, 1-3, 1-2, 1) $R^a$, each $R^a$ can be, independently of one another, $NR^gR^h$; $C_6$-$C_{18}$ (e.g., $C_6$-$C_{14}$, $C_6$-$C_{10}$, phenyl) aryloxy or heteroaryloxy including 5-16 (e.g., 5-14, 5-10, 5-6) atoms, each of which is optionally substituted with from 1-10 (e.g., 1-5, 1-4, 1-3, 1-2, 1) $R^b$; $C_7$-$C_{20}$ (e.g., $C_7$-$C_{16}$, $C_7$-$C_{12}$, $C_7$-$C_{10}$) aralkoxy or heteroaralkoxy including 6-20 (e.g., 6-14, 6-12, 6-10) atoms, each of which is optionally substituted with from 1-10 $R^c$; $C_6$-$C_{18}$ (e.g., $C_6$-$C_{14}$, $C_6$-$C_{10}$, phenyl) thioaryloxy or thioheteroaryloxy including 5-16 atoms, each of which is optionally substituted with from 1-10 $R^b$; or $C_7$-$C_{20}$ (e.g., $C_7$-$C_{16}$, $C_7$-$C_{12}$, $C_7$-$C_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) $R^c$. In certain embodiments, B can be $C_1$-$C_6$ alkyl, optionally substituted with 1 $R^a$ (e.g., B can be a substituted $CH_3$ group).

In certain embodiments, $R^a$ can be a $C_1$-$C_6$ alkyl (e.g., B can be a substituted $CH_3$ group) substituted with $NR^gR^h$. For example, one of $R^g$ and $R^h$ can be hydrogen, and the other can be $C_6$-$C_{18}$ aryl or heteroaryl including 5-16 atoms, each of which can be optionally substituted with from 1-10 $R^b$. In some embodiments, one of $R^g$ and $R^h$ can be hydrogen, and the other can be a phenyl or napthyl group, each of which is optionally substituted with from 1-5 (e.g., 1-3) $R^b$ (e.g., $C_1$-$C_4$ alkyl (e.g., $CH_3$) optionally substituted with 1 $R^a$ (e.g., COOH)). For example, one of $R^g$ and $R^h$ can be hydrogen, and the other can be a phenyl ring in which an ortho position, a meta position, and the para position are each substituted with a combination of $CH_3$ and $CH_2C(O)OH$ groups.

Other embodiments can include one or more of the following features (e.g., the various embodiments described elsewhere for $R^2$ can also be combined with one or more of the following features).

In some embodiments, $R^1$ can be hydrogen.

In some embodiments, $R^1$ can be:

(ii) $C_1$-$C_{20}$ (e.g., $C_1$-$C_{10}$, $C_1$-$C_6$, $C_1$-$C_3$) alkyl or $C_1$-$C_{20}$ (e.g., $C_1$-$C_{10}$, $C_1$-$C_6$, $C_1$-$C_3$) haloalkyl, each of which is optionally substituted with from 1-10 (e.g., 1-5, 1-4, 1-3, 1-2, 1) $R^a$; or (iii) $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$; or (iv) $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^b$; or (viii) —$C(O)NR^gR^h$; —$OC(O)NR^gR^h$; —$C(O)R^i$, —$C(O)OR^i$; —$OC(O)R^i$; —$C(O)SR^i$; —$SC(O)R^i$; —$C(S)SR^i$; —$SC(S)R^i$; —$NR^jC(O)R^i$; —$NR^jC(O)OR^i$; —$NR^jC(O)NR^gR^h$; —$S(O)_nR^k$; —$NR^jS(O)_nR^i$; —$C(NR^m)R^i$; or —$P(O)(OR^g)(OR^h)$.

In certain embodiments, $R^1$ can be:

(ii) $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or (iii) $C_7$-$C_{16}$ (e.g., $C_7$-$C_{12}$, $C_7$-$C_{10}$) aralkyl or heteroaralkyl including 6-16 (e.g., 6-14, 6-12, 6-10) atoms, each of which is optionally substituted with from 1-5 (e.g., 1-4, 1-3, 1-2, 1) $R^c$; or (iv) $C_6$-$C_{10}$ aryl or heteroaryl including 5-10 atoms, each of which is optionally substituted with from 1-5 (e.g., 1-4, 1-3, 1-2, 1) $R^b$; or (viii) —$C(O)NR^gR^h$; —$OC(O)NR^gR^h$; —$C(O)R^i$, —$C(O)OR^i$; —$OC(O)R^i$; —$C(O)SR^i$; —$SC(O)R^i$; —$C(S)SR^i$; —$SC(S)R^i$; —$NR^jC(O)R^i$; —$NR^jC(O)OR^i$; —$NR^c(O)$—$S(O)_nR^k$; —$NR^jS(O)_nR^i$; —$C(NR^m)R^i$; or —$P(O)(OR^g)(OR^h)$.

In certain embodiments, $R^1$ can be:

(ii) $C_1$-$C_{20}$ (e.g., $C_1$-$C_{10}$, $C_1$-$C_6$, $C_1$-$C_3$) alkyl optionally substituted with from 1-10 (e.g., 1-5, 1-4, 1-3, 1-2, 1) $R^a$; or (iii) $C_6$-$C_{18}$ (e.g., $C_6$-$C_{14}$, $C_6$-$C_{10}$, phenyl) aryl optionally substituted with from 1-10 (e.g., 1-5, 1-4, 1-3, 1-2, 1) $R^b$; or (iv) $C_7$-$C_{20}$ (e.g., $C_7$-$C_{16}$, $C_7$-$C_{12}$, $C_7$-$C_{10}$) aralkyl optionally substituted with from 1-10 (e.g., 1-5, 1-4, 1-3, 1-2, 1) $R^c$; or (viii) —$C(O)NR^gR^h$; —$OC(O)NR^gR^h$; —$C(O)R^i$, —$C(O)OR^i$; —$OC(O)R^i$; —$C(O)SR^i$; —$SC(O)R^i$; —$C(S)SR^i$; —$SC(S)R^i$; —$NR^jC(O)R^i$; —$NR^jC(O)OR^i$; —$NR^jC(O)NR^gR^h$; —$S(O)_nR^k$; —$NR^jS(O)_nR^i$; —$C(NR^m)R^i$; or —$P(O)(OR^g)(OR^h)$.

In certain embodiments, $R^1$ can be:

(ii) $C_1$-$C_{10}$ (e.g., $C_1$-$C_6$, $C_1$-$C_3$) alkyl optionally substituted with from 1-5 (e.g., 1-4, 1-3, 1-2, 1) $R^a$; or (iii) $C_6$-$C_{10}$ aryl optionally substituted with from 1-5 (e.g., 1-4, 1-3, 1-2, 1) $R^b$; or (iv) $C_7$-$C_{16}$ (e.g., $C_7$-$C_{12}$, $C_7$-$C_{10}$) aralkyl optionally substituted with from 1-5 (e.g., 1-4, 1-3, 1-2, 1) $R^c$; or (viii) —$C(O)NR^gR^h$; —$OC(O)NR^gR^h$; —$C(O)R^i$, —$C(O)OR^i$; —$OC(O)R^i$; —$C(O)SR^i$; —$SC(O)R^i$; —$C(S)SR^i$; —$SC(S)R^i$; —$NR^jC(O)R^i$; —$NR^jC(O)OR^i$; —$NR^j(O)NR^gR^h$; —$S(O)_nR^k$; —$NR^jS(O)_nR^i$; —$C(NR^m)R^i$; or —$P(O)(OR^g)(OR^h)$.

In certain embodiments, $R^1$ can be $C_1$-$C_{20}$ (e.g., $C_1$-$C_{10}$, $C_1$-$C_6$, $C_1$-$C_3$) alkyl optionally substituted with from 1-10 (e.g., 1-5, 1-4, 1-3, 1-2, 1) $R^a$.

In certain embodiments, $R^1$ can be $C_1$-$C_{10}$ (e.g., $C_1$-$C_6$, $C_1$-$C_3$) alkyl optionally substituted with from 1-5 (e.g., 1-4, 1-3, 1-2, 1) $R^a$.

In certain embodiments, $R^1$ can be $C_1$-$C_6$ (e.g., $C_1$-$C_3$) alkyl optionally substituted with from 1-3 (e.g., 1-2, 1) $R^a$.

In certain embodiments, $R^1$ can be $CH_3$.

In certain embodiments, $R^1$ can be $C_6$-$C_{18}$ (e.g., $C_6$-$C_{14}$, $C_6$-$C_{10}$, phenyl) aryl, optionally substituted with from 1-10 (e.g., 1-5, 1-4, 1-3, 1-2, 1) $R^b$.

In certain embodiments, $R^1$ can be $C_6$-$C_{10}$ (e.g., phenyl) aryl, optionally substituted with from 1-5 (e.g., 1-4, 1-3, 1-2, 1) $R^b$.

In certain embodiments, $R^1$ can be phenyl.

In certain embodiments, $R^1$ can be phenyl substituted with 1, 2, 3, 4, or 5 $R^b$.

In certain embodiments, when $R^1$ is phenyl substituted with 1, 2, 3, 4, or 5 $R^b$, each $R^b$ can be, independently of one another, $C_1$-$C_6$ (e.g., $C_1$-$C_3$) alkyl, $C_1$-$C_6$ (e.g., $C_1$-$C_3$)

haloalkyl, $C_1$-$C_6$ (e.g., $C_1$-$C_3$) alkoxy, $C_1$-$C_6$ (e.g., $C_1$-$C_3$) haloalkoxy, halo, $NO_2$, $NR^gR^h$, or cyano.

In certain embodiments, each $R^b$ can be, independently of one another, $C_1$-$C_6$ (e.g., $C_1$-$C_3$) alkyl, $C_1$-$C_6$ (e.g., $C_1$-$C_3$) haloalkyl, $C_1$-$C_6$ (e.g., $C_1$-$C_3$) alkoxy, halo, $NO_2$, $NR^gR^h$, or cyano.

In certain embodiments, each $R^b$ can be, independently of one another, $C_1$-$C_3$ alkyl, $C_1$-$C_3$ haloalkyl (e.g., $C_1$-$C_3$ haloalkyl having 1, 2, 3, 4, or 5 halogens (e.g., fluoro) or $C_1$-$C_3$ perhaloalkyl (e.g., $C_1$-$C_3$ perfluoroalkyl)); $C_1$-$C_3$ alkoxy, halo, $NO_2$, $NH_2$, or cyano.

In certain embodiments, each $R^b$ can be, independently of one another, $C_1$-$C_3$ alkyl, $C_1$-$C_3$ haloalkyl (e.g., $C_1$-$C_3$ haloalkyl having 1, 2, 3, 4, or 5 halogens (e.g., fluoro) or $C_1$-$C_3$ perhaloalkyl (e.g., $C_1$-$C_3$ perfluoroalkyl)); or $C_1$-$C_3$ alkoxy (e.g., compound of formula (I) in which $R^2$ is phenyl substituted (e.g., meta-substituted) with —$NR^jC(O)NR^gR^h$).

In certain embodiments, $R^1$ can be $C_7$-$C_{20}$ (e.g., $C_7$-$C_{16}$, $C_7$-$C_{12}$, $C_7$-$C_{10}$) aralkyl optionally substituted with from 1-10 (e.g., 1-5, 1-4, 1-3, 1-2, 1) $R^c$.

In certain embodiments, $R^1$ can be $C_7$-$C_{12}$ aralkyl optionally substituted with from 1-5 (e.g., 1-4, 1-3, 1-2, 1) $R^c$.

In certain embodiments, $R^1$ can be benzyl.

In certain embodiments, $R^1$ can be —$C(O)R^i$, in which $R^i$ can be $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^b$. In certain embodiments, $R^i$ can be phenyl or phenyl substituted with 1, 2, 3, 4, or 5 $R^b$. In certain embodiments, each $R^b$ can be, independently of one another, $C_1$-$C_6$ (e.g., $C_1$-$C_3$) alkyl, $C_1$-$C_6$ (e.g., $C_1$-$C_3$) haloalkyl, $C_1$-$C_6$ (e.g., $C_1$-$C_3$) alkoxy, $C_1$-$C_6$ (e.g., $C_1$-$C_3$) haloalkoxy, halo, $NO_2$, $NR^gR^h$, or cyano. In certain embodiments, each $R^b$ can be, independently of one another, $C_1$-$C_3$ alkyl, $C_1$-$C_3$ haloalkyl (e.g., $C_1$-$C_3$ haloalkyl having 1, 2, 3, 4, or 5 halogens (e.g., fluoro) or $C_1$-$C_3$ perhaloalkyl (e.g., $C_1$-$C_3$ perfluoroalkyl)); $C_1$-$C_3$ alkoxy, $C_1$-$C_3$ haloalkoxy, halo, $NO_2$, $NH_2$, or cyano.

In some embodiments, each of $R^3$, $R^4$ and $R^5$ can be, independently of one another, hydrogen or halo (e.g., fluoro). In certain embodiments, each of $R^3$, $R^4$ and $R^5$ can be hydrogen.

In some embodiments, $R^6$ can be hydrogen, halo, $C_1$-$C_{10}$ (e.g., $C_1$-$C_6$, $C_1$-$C_3$) alkyl, or $C_1$-$C_{10}$ (e.g., $C_1$-$C_6$, $C_1$-$C_3$) haloalkyl.

In certain embodiments, $R^6$ can be hydrogen, halo, $C_1$-$C_6$ alkyl, or $C_1$-$C_6$ haloalkyl.

In certain embodiments, $R^6$ can be hydrogen, halo, $C_1$-$C_3$ alkyl, or $C_1$-$C_3$ haloalkyl.

In certain embodiments, $R^6$ can be hydrogen, Br, Cl, $CH_3$ or $CF_3$.

In certain embodiments, $R^6$ can be halo, $C_1$-$C_{10}$ (e.g., $C_1$-$C_6$, $C_1$-$C_3$) alkyl, or $C_1$-$C_{10}$ (e.g., $C_1$-$C_6$, $C_1$-$C_3$) haloalkyl.

In certain embodiments, $R^6$ can be halo, $C_1$-$C_6$ alkyl, or $C_1$-$C_6$ haloalkyl.

In certain embodiments, $R^6$ can be halo, $C_1$-$C_3$ alkyl, or $C_1$-$C_3$ haloalkyl.

In certain embodiments, $R^6$ can be Br, Cl, $CH_3$ or $CF_3$.

In certain embodiments, $R^6$ can be Br or Cl. In certain embodiments, $R^6$ can be Cl.

In certain embodiments, $R^6$ can be $CH_3$.

In certain embodiments, $R^6$ can be $CF_3$.

In certain embodiments, $R^6$ can be hydrogen.

In certain embodiments, each of $R^3$, $R^4$, $R^5$, and $R^6$ can be, independently of one another:

(i) hydrogen, halo; $NO_2$; $NR^gR^h$; hydroxy; $C_1$-$C_{20}$ (e.g., $C_1$-$C_{10}$, $C_1$-$C_6$, $C_1$-$C_3$) alkoxy or $C_1$-$C_{20}$ (e.g., $C_1$-$C_{10}$, $C_1$-$C_6$, $C_1$-$C_3$) haloalkoxy, each of which is optionally substituted with from 1-10 (e.g., 1-5, 1-4, 1-3, 1-2, 1) $R^a$; $C_6$-$C_{18}$ (e.g., $C_6$-$C_{14}$, $C_6$-$C_{10}$, phenyl) aryloxy or heteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; $C_7$-$C_{20}$ (e.g., $C_7$-$C_{16}$, $C_7$-$C_{12}$, $C_7$-$C_{10}$) aralkoxy or heteroaralkoxy including 6-20 (e.g., 6-14, 6-12, 6-10) atoms, each of which is optionally substituted with from 1-10 (e.g., 1-5, 1-4, 1-3, 1-2, 1) $R^c$; $C_3$-$C_{20}$ (e.g., $C_3$-$C_{16}$, $C_3$-$C_{12}$, $C_3$-$C_8$) cycloalkoxy or $C_3$-$C_{20}$ (e.g., $C_3$-$C_{16}$, $C_3$-$C_{12}$, $C_3$-$C_8$) halocycloalkoxy, each of which is optionally substituted with from 1-10 (e.g., 1-5, 1-4, 1-3, 1-2, 1) $R^e$; $C_3$-$C_{20}$ (e.g., $C_3$-$C_{16}$, $C_3$-$C_{12}$, $C_3$-$C_8$) cycloalkenyloxy, heterocyclyloxy including 3-20 (e.g., 3-16, 3-12, 3-8) atoms, or heterocycloalkenyloxy including 3-20 (e.g., 3-16, 3-12, 3-8) atoms, each of which is optionally substituted with from 1-10 (e.g., 1-5, 1-4, 1-3, 1-2, 1) $R^f$; mercapto; $C_1$-$C_{20}$ (e.g., $C_1$-$C_{10}$, $C_1$-$C_6$, $C_1$-$C_3$) thioalkoxy or $C_1$-$C_{20}$ (e.g., $C_1$-$C_{10}$, $C_1$-$C_6$, $C_1$-$C_3$) thiohaloalkoxy, each of which is optionally substituted with from 1-10 (e.g., 1-5, 1-4, 1-3, 1-2, 1) $R^a$; $C_6$-$C_{18}$ (e.g., $C_6$-$C_{14}$, $C_6$-$C_{10}$, phenyl) thioaryloxy or thioheteroaryloxy including 5-16 (e.g., 5-14, 5-10, 5-6) atoms, each of which is optionally substituted with from 1-10 (e.g., 1-5, 1-4, 1-3, 1-2, 1) $R^{b'}$; $C_7$-$C_{20}$ (e.g., $C_7$-$C_{16}$, $C_7$-$C_{12}$, $C_7$-$C_{10}$) thioaralkoxy or thioheteroaralkoxy including 6-20 (e.g., 6-14, 6-12, 6-10) atoms, each of which is optionally substituted with from 1-10 (e.g., 1-5, 1-4, 1-3, 1-2, 1) $R^c$; $C_3$-$C_{16}$ (e.g., $C_3$-$C_{16}$, $C_3$-$C_{12}$, $C_3$-$C_8$) thiocycloalkoxy or $C_3$-$C_{16}$ (e.g., $C_3$-$C_{16}$, $C_3$-$C_{12}$, $C_3$-$C_8$) thiohalocycloalkoxy, each of which is optionally substituted with from 1-10 (e.g., 1-5, 1-4, 1-3, 1-2, 1) $R^e$; $C_3$-$C_{20}$ (e.g., $C_3$-$C_{16}$, $C_3$-$C_{12}$, $C_3$-$C_8$) thiocycloalkenyloxy, thioheterocyclyloxy including 3-20 (e.g., 3-16, 3-12, 3-8) atoms, or thioheterocycloalkenyloxy including 3-20 (e.g., 3-16, 3-12, 3-8) atoms, each of which is optionally substituted with from 1-10 (e.g., 1-5, 1-4, 1-3, 1-2, 1) $R^f$; cyano; —$C(O)NR^gR^h$; —$OC(O)NR^gR^h$; —$C(O)R^i$; —$C(O)OR^i$; —$OC(O)R^i$; —$C(O)SR^i$; —$SC(O)R^i$; —$C(S)SR^i$; —$SC(S)R^i$; —$NR^jC(O)R^i$; —$NR^jC(O)OR^i$; —$NR^jC(O)NR^gR^h$; —$S(O)_nR^k$; —$NR^jS(O)_nR^i$; —$C(NR^m)R^i$; or —$P(O)(OR^g)(OR^h)$; or (ii) $C_1$-$C_{20}$ (e.g., $C_1$-$C_{10}$, $C_1$-$C_6$, $C_1$-$C_3$) alkyl or $C_1$-$C_{20}$ (e.g., $C_1$-$C_{10}$, $C_1$-$C_6$, $C_1$-$C_3$) haloalkyl, each of which is optionally substituted with from 1-10 (e.g., 1-5, 1-4, 1-3, 1-2, 1) $R^a$; or (iii) $C_3$-$C_{20}$ (e.g., $C_3$-$C_{16}$, $C_3$-$C_{12}$, $C_3$-$C_8$) cycloalkyl or $C_3$-$C_{20}$ (e.g., $C_3$-$C_{16}$, $C_3$-$C_{12}$, $C_3$-$C_8$) halocycloalkyl, optionally substituted with from 1-10 (e.g., 1-5, 1-4, 1-3, 1-2, 1) $R^e$; or (iv) $C_3$-$C_{20}$ (e.g., $C_3$-$C_{16}$, $C_3$-$C_{12}$, $C_3$-$C_8$) cycloalkenyl, heterocyclyl including 3-20 (e.g., 3-16, 3-12, 3-8) atoms, or heterocycloalkenyl including 3-20 (e.g., 3-16, 3-12, 3-8) atoms, each of which is optionally substituted with from 1-10 $R^f$; or (v) $C_2$-$C_{20}$ alkenyl or $C_2$-$C_{20}$ alkynyl, each of which is optionally substituted with from 1-10 $R^d$; or (vi) $C_7$-$C_{20}$ (e.g., $C_7$-$C_{16}$, $C_7$-$C_{12}$, $C_7$-$C_{10}$) aralkyl or heteroaralkyl including 6-20 (e.g., 6-14, 6-12, 6-10) atoms, each of which is optionally substituted with from 1-10 (e.g., 1-5, 1-4, 1-3, 1-2, 1) $R^c$; or (vii) $C_6$-$C_{18}$ (e.g., $C_6$-$C_{14}$, $C_6$-$C_{10}$, phenyl) aryl or heteroaryl including 5-16 (e.g., 5-14, 5-10, 5-6) atoms, each of which is optionally substituted with from 1-10 (e.g., 1-5, 1-4, 1-3, 1-2, 1) $R^{b'}$.

In some embodiments, the cinnoline-based, LXR modulators can have formula (V):

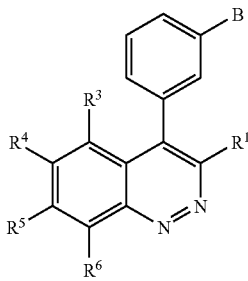

(V)

in which $R^1$, $R^3$, $R^4$, $R^5$, $R^6$, and B are as defined elsewhere for compounds having formula (V).

In certain embodiments, $R^1$ can be $C_1$-$C_{20}$ (e.g., $C_1$-$C_{10}$, $C_1$-$C_6$, $C_1$-$C_3$) alkyl optionally substituted with from 1-10 (e.g., 1-5, 1-4, 1-3, 1-2, 1) $R^a$. In certain embodiments, $R^1$ can be $CH_3$.

In certain embodiments, $R^1$ can be $C_6$-$C_{18}$ (e.g., $C_6$-$C_{14}$, $C_6$-$C_{10}$, phenyl) aryl optionally substituted with from 1-10 (e.g., 1-5, 1-4, 1-3, 1-2, 1) $R^b$. In certain embodiments, $R^1$ can be phenyl.

In certain embodiments, $R^1$ can be $C_7$-$C_{20}$ (e.g., $C_7$-$C_{16}$, $C_7$-$C_{12}$, $C_7$-$C_{10}$) aralkyl optionally substituted with from 1-10 (e.g., 1-5, 1-4, 1-3, 1-2, 1) $R^c$. In certain embodiments, $R^1$ can be benzyl.

$R^1$ can be H.

In certain embodiments, $R^6$ can be hydrogen, halo, $C_1$-$C_{10}$ (e.g., $C_1$-$C_6$, $C_1$-$C_3$) alkyl, or $C_1$-$C_{10}$ (e.g., $C_1$-$C_6$, $C_1$-$C_3$) haloalkyl. In certain embodiments, $R^6$ can be hydrogen, Br, Cl, $CH_3$ or $CF_3$.

In certain embodiments, each of $R^3$, $R^4$ and $R^5$ can be, independently of one another, hydrogen or halo (e.g., fluoro). In certain embodiments, each of $R^3$, $R^4$ and $R^5$ can be hydrogen.

In certain embodiments, B can be hydrogen, $NH_2$, or OH.

In certain embodiments, B can have formula (III), in which one of $R^g$ and $R^h$ can be hydrogen, and the other can be $C_6$-$C_{18}$ (e.g., $C_6$-$C_{14}$, $C_6$-$C_{10}$, phenyl) aryl optionally substituted with from 1-10 (e.g., 1-5, 1-4, 1-3, 1-2, 1) $R^b$. E.g., one of $R^g$ and $R^h$ can be hydrogen, and the other can be phenyl.

In certain embodiments, B can have formula (IV), in which W can be NH, O, or S, j can be 1, and each of $R^{b1}$, $R^{b2}$, $R^{b3}$, $R^{b4}$, and $R^{b5}$ can be as defined elsewhere.

In certain embodiments, each of $R^{b1}$, $R^{b2}$, $R^{b3}$, $R^{b4}$, and $R^{b5}$ can be hydrogen.

In certain embodiments, any one of $R^{b1}$, $R^{b2}$, $R^{b3}$, $R^{b4}$, or $R^{b5}$ (e.g., $R^{b1}$ or $R^{b5}$; $R^{b2}$ or $R^{b4}$; or $R^{b3}$) or any two of $R^{b1}$, $R^{b2}$, $R^{b3}$, $R^{b4}$, or $R^{b5}$ ($R^{b1}$ and $R^{b2}$; $R^{b1}$ and $R^{b3}$; $R^{b1}$ and $R^{b4}$; $R^{b1}$ and $R^{b5}$; $R^{b2}$ and $R^{b3}$; $R^{b2}$ and $R^{b4}$; $R^{b2}$ and $R^{b5}$; etc., e.g., $R^{b1}$ and $R^{b2}$; $R^{b1}$ and $R^{b4}$; or $R^{b2}$ and $R^{b3}$) can be, independently of one another, halo; $NO_2$; hydroxy; $C_1$-$C_{10}$ (e.g., $C_1$-$C_6$, $C_1$-$C_3$) alkoxy; $C_1$-$C_{10}$ (e.g., $C_1$-$C_6$, $C_1$-$C_3$) haloalkoxy; cyano; —C(O)$R^i$; $C_1$-$C_{10}$ (e.g., $C_1$-$C_6$, $C_1$-$C_3$) alkyl or $C_1$-$C_{10}$ (e.g., $C_1$-$C_6$, $C_1$-$C_3$) haloalkyl, each of which is optionally substituted with from 1-5 (e.g., 1-4, 1-3, 1-2, 1) $R^a$; or —C(O)$OR^i$; and the other(s) can be hydrogen.

In certain embodiments, any one of $R^{b1}$, $R^{b2}$, $R^{b3}$, $R^{b4}$, or $R^{b5}$ (e.g., $R^{b1}$ or $R^{b5}$; $R^{b2}$ or $R^{b4}$; or $R^{b3}$) or any two of $R^{b1}$, $R^{b2}$, $R^{b3}$, $R^{b4}$, or $R^{b5}$ ($R^{b1}$ and $R^{b2}$; $R^{b1}$ and $R^{b3}$; $R^{b1}$ and $R^{b4}$; $R^{b1}$ and $R^{b5}$; $R^{b2}$ and $R^{b3}$; $R^{b2}$ and $R^{b4}$; $R^{b2}$ and $R^{b5}$; etc., e.g., $R^{b1}$ and $R^{b2}$; $R^{b1}$ and $R^{b4}$; or $R^{b2}$ and $R^{b3}$) can be, independently of one another, halo; $NO_2$; hydroxy; $C_1$-$C_6$ alkoxy; $C_1$-$C_6$ haloalkoxy; cyano; —C(O)$R^i$; $C_1$-$C_6$ alkyl or $C_1$-$C_6$ haloalkyl, each of which is optionally substituted with from 1-3 $R^a$; or —C(O)$OR^i$; and the other(s) can be hydrogen.

In certain embodiments, any one of $R^{b1}$, $R^{b2}$, $R^{b3}$, $R^{b4}$, or $R^{b5}$ (e.g., $R^{b1}$ or $R^{b5}$; $R^{b2}$ or $R^{b4}$; or $R^{b3}$) or any two of $R^{b1}$, $R^{b2}$, $R^{b3}$, $R^{b4}$, or $R^{b5}$ ($R^{b1}$ and $R^{b2}$; $R^{b1}$ and $R^{b3}$; $R^{b1}$ and $R^{b4}$; $R^{b1}$ and $R^{b5}$; $R^{b2}$ and $R^{b3}$; $R^{b2}$ and $R^{b4}$; $R^{b2}$ and $R^{b5}$; etc., e.g., $R^{b1}$ and $R^{b2}$; $R^{b1}$ and $R^{b4}$; or $R^{b2}$ and $R^{b3}$) can be, independently of one another, halo; $NO_2$; hydroxy; $C_1$-$C_3$ alkoxy; $C_1$-$C_3$ haloalkoxy; cyano; —C(O)$R^i$ (e.g., —C(O)(heterocyclyl including 3-20 atoms); $C_1$-$C_4$ alkyl or $C_1$-$C_4$ haloalkyl (e.g., $C_1$-$C_4$ perhaloalkyl, e.g., $C_1$-$C_4$ perfluoroalkyl), each of which is optionally substituted with from 1-2 $R^a$ (e.g., —C(O)OH or —C(O)$OCH_3$); or —C(O)$OR^i$; and the other(s) can be hydrogen.

In certain embodiments, any one of $R^{b1}$, $R^{b2}$, $R^{b3}$, $R^{b4}$, or $R^{b5}$ (e.g., $R^{b1}$ or $R^{b5}$; $R^{b2}$ or $R^{b4}$; or $R^{b3}$) or any two of $R^{b1}$, $R^{b2}$, $R^{b3}$, $R^{b4}$, or $R^{b5}$ ($R^{b1}$ and $R^{b2}$; $R^{b1}$ and $R^{b3}$; $R^{b1}$ and $R^{b4}$; $R^{b1}$ and $R^{b5}$; $R^{b2}$ and $R^{b3}$; $R^{b2}$ and $R^{b4}$; $R^{b2}$ and $R^{b5}$; etc., e.g., $R^{b1}$ and $R^{b2}$; $R^{b1}$ and $R^{b4}$; or $R^{b2}$ and $R^{b3}$) can be, independently of one another, F; Cl; Br; OH; $OCH_3$; $OCF_3$; —C(O)(morpholino); $CH_3$; $CH_3$ substituted with from 1-2 $R^a$ (e.g., —C(O)OH or —C(O)$OCH_3$); $CF_3$; —C(O)OH; or —C(O)$OCH_3$; and the other(s) can be hydrogen.

In certain embodiments, $R^{b3}$ can be $C_1$-$C_4$ alkyl substituted with 1 $R^a$, and each of $R^{b1}$, $R^{b2}$, $R^{b4}$, and $R^{b5}$ can be hydrogen. In certain embodiments, $R^a$ can be C(O)$OR^i$, in which $R^i$ can be hydrogen or $C_1$-$C_4$ alkyl (e.g., $CH_3$). In certain embodiments, $R^{b3}$ can be —$CH_2$C(O)OH, —$CH_2$C(O)$OCH_3$, —C($CH_3$)$_2$C(O)OH, or —C($CH_3$)$_2$C(O)$OCH_3$. In certain embodiments, $R^{b3}$ can be —C(O)$OR^i$ (e.g., COOH).

In certain embodiments, $R^{b2}$ can be $C_1$-$C_4$ haloalkyl (e.g., $C_1$-$C_4$ perhaloalkyl, e.g., $C_1$-$C_4$ perfluoroalkyl, e.g., $CF_3$); or —C(O)$R^i$ (e.g., —C(O)(heterocyclyl including 3-20 atoms), e.g., —C(O)(morpholino)); or —C(O)$OR^i$ (e.g., COOH); and each of $R^{b1}$, $R^{b3}$, $R^{b4}$, and $R^{b5}$ can be hydrogen.

In certain embodiments, $R^{b1}$ can be halo (e.g., Cl) or $C_1$-$C_6$ haloalkoxy (e.g., $OCF_3$), and each of $R^{b1}$, $R^{b3}$, $R^{b4}$, and $R^{b5}$ can be hydrogen.

In certain embodiments, $R^{b1}$ and $R^{b4}$ can both be $C_1$-$C_4$ alkyl (e.g., $CH_3$), and each of $R^{b2}$, $R^{b3}$, and $R^{b5}$ can be hydrogen.

In certain embodiments, $R^{b1}$ can be $C_1$-$C_4$ haloalkyl (e.g., $CF_3$), $R^{b4}$ can be halo (e.g., F, Cl), and each of $R^{b2}$, $R^{b3}$, and $R^{b5}$ can be hydrogen.

In certain embodiments, $R^{b1}$ and $R^{b4}$ can both be $C_1$-$C_4$ haloalkyl (e.g., $CF_3$), and each of $R^{b2}$, $R^{b3}$, and $R^{b5}$ can be hydrogen.

In certain embodiments, $R^{b1}$ can be halo (e.g., F, Br); $R^{b4}$ can be $C_1$-$C_4$ alkyl (e.g., $CH_3$), or $C_1$-$C_4$ haloalkyl (e.g., $CF_3$), or $C_1$-$C_3$ alkoxy (e.g., $OCH_3$), or halo (e.g., Br); and each of $R^{b2}$, $R^{b3}$, and $R^{b5}$ can be hydrogen.

In certain embodiments, $R^{b1}$ can be $C_1$-$C_3$ alkoxy (e.g., $OCH_3$), $R^{b4}$ can be halo (e.g., Br), and each of $R^{b2}$, $R^{b3}$, and $R^{b5}$ can be hydrogen.

In certain embodiments, $R^{b1}$ and $R^{b2}$ can both be $C_1$-$C_4$ alkyl (e.g., $CH_3$), and each of $R^{b3}$, $R^{b4}$, and $R^{b5}$ can be hydrogen.

In certain embodiments, $R^{b1}$ can be halo (e.g., F, Cl), $R^{b2}$ can be $C_1$-$C_4$ haloalkyl (e.g., $CF_3$), and each of $R^{b3}$, $R^{b4}$, and $R^{b5}$ can be hydrogen.

In certain embodiments, $R^{b2}$ and $R^{b3}$ can both be halo (e.g., Cl), and each of $R^{b1}$, $R^{b4}$, and $R^{b5}$ can be hydrogen.

In certain embodiments, $R^{b2}$ can be halo (e.g., F, Cl), $R^{b3}$ can be $C_1$-$C_4$ haloalkyl (e.g., $CF_3$), and each of $R^{b1}$, $R^{b4}$, and $R^{b5}$ can be hydrogen.

In certain embodiments, $R^{b2}$ and $R^{b3}$ can each be, independently, $C_1$-$C_6$ alkoxy (e.g., $OCH_3$) or —C(O)$OR^i$ (e.g., COOH); and each of $R^{b1}$, $R^{b4}$, and $R^{b5}$ can be hydrogen.

In certain embodiments, $R^{b1}$ and $R^{b5}$ can both be halo (e.g., chloro), and each of $R^{b2}$, $R^{b3}$, and $R^{b4}$ can be hydrogen.

In certain embodiments, $R^{b1}$ can be halo (e.g., chloro), $R^{b3}$ can be —C(O)$OR^i$ (e.g., COOH), and each of $R^{b2}$, $R^{b4}$, and $R^{b5}$ can be hydrogen.

When B is as described in (i-B), (ii-B), (iii-B), (iv-B), (i-B'), (ii-B'), (iii-B'), (iv-B')), B can also be W—$(CH_2)_j$-(bicyclic or tricyclic aryl) or W—$(CH_2)_j$-(heteroaryl), in which W and j can be as described elsewhere for Formula (IV).

B can be —NH—$CH_2$-naphthyl (e.g., the methylene group can be attached to the 1 or 2 position of the naphthyl ring, and the naphthyl ring can optionally be substituted in one or more positions, e.g., with 1-5, 1-4, 1-3, 1-2, or 1 $R^c$).

In certain embodiments, B can be —NH—$CH_2$-indolyl or —O—$CH_2$-indolyl (e.g., the methylene group can be attached to the 2 or 7 position of the indole ring, and the indole ring can be optionally substituted in one or more positions, e.g., with 1-5, 1-4, 1-3, 1-2, or 1 $R^c$, e.g., at the 1-position with $CH_3$ and/or at the 5-position with halo (e.g., fluoro) and/or at the 3-position with $COOR^i$ (e.g., COOH).

In certain embodiments, B can be —NH—$CH_2$-benzothienyl (e.g., the methylene group can be attached to the 2 or 3 position of the benzothienyl ring, and the benzothienyl ring can be optionally substituted in one or more positions, e.g., with 1-5, 1-4, 1-3, 1-2, or 1 $R^c$, e.g., at the 3-position with $C_1$-$C_6$ alkyl (e.g., $CH_3$) or at the 4-position with $C_1$-$C_4$ haloalkyl (e.g., $CF_3$)).

In some embodiments, the cinnoline-based, LXR modulators can have formula (VI):

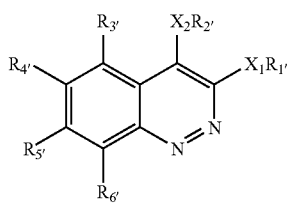

(VI)

in which $X_1$, $R_{1'}$, $X_2$, $R_{2'}$, $R_{3'}$, $R_{4'}$, $R_{5'}$, $R_{6'}$ can be as defined elsewhere.

In certain embodiments:

$X_1$ can be a bond, —C(O)—, —O—, —S(O)$_t$—, —$NR_8$—, or —$CR_8R_9$—.

$R_{1'}$ can be $C_1$ to $C_6$ alkyl, phenyl, or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR_8R_9$, —CN, —OH, and $C_1$ to $C_3$ alkyl substituted with 1 to 5 fluorines, or $R_{1'}$ can be a heterocycle selected from the group consisting of pyridine, thiophene, benzisoxazole, benzothiophene, oxadiazole, pyrrole, pyrazole, and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —$NO_2$, —$NR_8R_9$, —CN, and $C_1$ to $C_3$ alkyl substituted with 1 to 5 fluorines.

$X_2$ can be a bond or —$CH_2$—.

$R_{2'}$ can be phenyl, naphthyl, or phenyl or naphthyl substituted independently by one to four groups independently selected from $C_1$ to $C_3$ alkyl, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R_{10}$, —C(O)$NR_{10}R_{11}$, —C(O)$NR_{11}$A, —C≡$CR_8$, —CH=$CHR_8$, —W'A, —C≡CA, —CH=CHA, —W'YA, —W'$YR_{10}$, —W'Y$(CH_2)_j$A, —W'$CHR_{11}(CH_2)_j$A, —W'$(CH_2)_j$A, —W' $(CH_2)_j R_{10}$, —$CHR_{11}$W'$(CH_2)_j R_{10}$, —$CHR_{11}$W'$(CH_2)_j$A, —$CHR_{11}NR_{12}$YA, —$CHR_{11}NR_{12}YR_{10}$, and pyrrole, or $R_{2'}$ can be a heterocycle selected from pyridine, pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$ alkyl, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R^{10}$, —C(O)$NR_{10}R_{11}$, —C(O)$NR_{11}$A, —C≡$CR_8$, —CH=$CHR_8$, —W'A, —C≡CA, —CH=CHA, —W'YA, —W'$YR_{10}$, —W'Y$(CH_2)_j$A, —W'$(CH_2)_j$A, —W'$(CH_2)_j R_{10}$, —$CHR_{11}$W'$(CH_2)_j R_{10}$, —$CHR_{11}$W'$(CH_2)_j$A, —$CHR_{11}NR^{12}$YA, and —$CHR_{11}NR_{12}YR_{10}$.

W' can be a bond, —O—, —S—, —S(O)—, —S(O)$_2$—, —$NR_{11}$—, or —$N(COR_{12})$—.

Y can be —CO—, —S(O)$_2$—, —$CONR_{13}$, —$CONR_{13}$CO—, —$CONR_{13}SO_2$—, —C(NCN)—, —$CSNR_{13}$, —C(NH)$NR_{13}$, or —C(O)O—.

j can be 0 to 3.

t can be 0 to 2.

A can be phenyl, naphthyl, tetrahydronaphthyl, or phenyl substituted by one to four groups independently selected from halogen, $C_1$ to $C_3$ alkyl, $C_2$ to $C_4$ alkenyl, $C_2$ to $C_4$ alkynyl, acyl, $C_1$ to $C_3$ alkoxy, hydroxy, halogen, —CN, —$NO_2$, —$CO_2R_{11}$, —$CH_2CO_2R_{11}$, phenyl, phenoxy, $C_1$ to $C_3$ perfluoroalkoxy, $C_1$ to $C_3$ perfluoroalkyl, —$NR_{10}R_{11}$, —$CH_2NR_{10}R_{11}$, —$SR_{11}$, $C_1$ to $C_3$ alkyl substituted with 1 to 5 fluorines, $C_1$ to $C_6$ alkyl substituted with 1 to 2-OH groups, and $C_1$ to $C_6$ alkoxy optionally substituted with 1 to 5 fluorines; or A can be a heterocycle selected from pyrrole, pyridine, pyrimidine, thiophene, furan, quinoline, oxazole, thiazole, imidazole, isoxazole, indole, benzo[1,3]-dioxole, benzo[1,2,5]-oxadiazole, isochromen-1-one, and 3-H-isobenzofuran-1-one, each of which may be optionally substituted by one to three groups independently selected from halogen, $C_1$ to $C_3$ alkyl, acyl, $C_1$ to $C_3$ alkoxy, hydroxy, halogen, —CN, —$NO_2$, $C_1$ to $C_3$ perfluoroalkyl, —$NR_{10}R_{11}$, —$CH_2NR_{10}R_{11}$, —$SR_{11}$, $C_1$ to $C_6$ alkyl substituted with 1 to 5 fluorines, and $C_1$ to $C_6$ alkoxy optionally substituted with 1 to 5 fluorines.

$R_{3'}$, $R_{4'}$, $R_{5'}$ can each be, independently, —H.

$R_{6'}$ can be $C_1$ to $C_4$ alkyl, $C_1$ to $C_4$ perfluoroalkyl, or halogen.

Each $R_8$ can be independently —H, or $C_1$ to $C_2$ alkyl.

Each $R_9$ can be independently —H, or $C_1$ to $C_2$ alkyl.

Each $R_{10}$ can be independently —H, $C_1$ to $C_7$ alkyl, $C_2$ to $C_7$ alkenyl, or $C_3$ to $C_7$ cycloalkyl;

Each $R_{11}$ can be independently —H, or $C_1$ to $C_3$ alkyl.

Each $R_{12}$ can be independently —H, or $C_1$ to $C_3$ alkyl.

In certain embodiments:

$X_1$ can be a bond, —C(O)—, or —$CR_8R_9$—.

$R_{1'}$ can be phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR_8R_9$, —CN, —OH, and $C_1$ to $C_3$ alkyl substituted with 1 to 5 fluorines, or $R_{1'}$ can be a heterocycle selected from the group consisting of pyridine, thiophene, and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —$NO_2$, —$NR_8R_9$, CN, and $C_1$ to $C_3$ alkyl substituted with 1 to 5 fluorines, $X_2$ can be a bond.

$R_{2'}$ can be phenyl substituted independently by one to four groups independently selected from hydroxy, halogen, $C_1$ to $C_3$ perfluoroalkyl, $C_1$ to $C_3$ alkyl substituted with 1 to 5 fluorines, —C≡$CR_8$, —CH=$CHR_8$, —W'A, —C≡CA, —W'YA, —W'Y$(CH_2)_j$A, —W'$(CH_2)_j$A, —W'$CHR_{11}$$(CH_2)_j$A, and —$CHR_{11}$W'$(CH_2)_j$A.

In certain embodiments:

$X_1$ can be a bond, —C(O)—, —O—, —S(O)$_t$—, —$NR_8$—, —$CR_8R_9$—, or —$CR_8(OR_9)$—.

$R_1$ can be $C_1$ to $C_6$ alkyl, $C_2$ to $C_6$ alkenyl, $C_2$ to $C_6$ alkynyl, $C_3$ to $C_8$ cycloalkyl, —$CH_2OH$, $CF_3$, CN, phenyl, or phenyl substituted by one to four groups independently selected from $C_1$ to $C_3$ alkyl, $C_1$ to $C_3$ alkoxy, $C_1$ to $C_2$ perfluoroalkyl, halogen, —$NO_2$, —$NR_8R_9$, —CN, and $C_1$ to $C_2$ alkyl substituted with 1 to 3 fluorines, or $R_{1'}$ can be a heterocycle selected from pyridine, thiophene, and furan, each of which may be optionally substituted with one to three groups independently selected from $C_1$ to $C_3$ alkyl, $C_1$ to $C_3$ alkoxy, $C_1$ to $C_2$ perfluoroalkyl, halogen, —$NO_2$, —$NR_8R_9$, —CN, and $C_1$ to $C_2$ alkyl substituted with 1 to 3 fluorines.

$X_2$ can be a bond or —$CH_2$—.

$R_{2'}$ can be phenyl substituted by —W'$(CH_2)_j$A$(CH_2)_k$D$(CH_2)_p$Z, —W'$(CR_{18}R_{19})$A$(CH_2)_k$D$(CH_2)_p$Z, —$(CH_2)_j$W'A$(CH_2)_k$D$(CH_2)_p$Z, —CH=CHA$(CH_2)_k$D$(CH_2)_p$Z, —C≡CA$(CH_2)_k$D$(CH_2)_p$Z, or W'$(CH_2)_j$C≡CA$(CH_2)_k$D$(CH_2)_p$Z, and further optionally substituted with one or two groups independently selected from $C_1$ to $C_2$ alkyl, $C_1$ to $C_2$ perfluoroalkyl, halogen, and —CN, or $R_{2'}$ can be a heterocycle selected from pyridine, pyrimidine, thiophene, and furan, each of which is optionally substituted by —W'$(CH_2)_j$A$(CH_2)_k$D$(CH_2)_p$Z, —W'$(CR_{18}R_{19})$A$(CH_2)_k$D$(CH_2)_p$Z, —$(CH_2)_j$W'A$(CH_2)_k$D$(CH_2)_p$Z, —CH=CHA$(CH_2)_k$D$(CH_2)_p$Z, —C≡CA$(CH_2)_k$D$(CH_2)_p$Z, or —W'$(CH_2)_j$C≡CA$(CH_2)_k$D$(CH_2)_p$Z.

W' can be a bond, —O—, —S—, —S(O)—, —S(O)$_2$—, —$NR_{11}$—, or —N(COR$_{12}$)—.

j can be 0 to 3.

k can be 0 to 3.

t can be 0 to 2.

D can be a bond, —CH=CH—, —C≡C—, phenyl, —O—, —NH—, —S—, —$CHR_{14}$—, —$CR_{14}R_{15}$—, —$OCHR_{14}$—, —$OCR_{14}R_{15}$—, or —CH(OH)CH(OH)—.

p can be 0 to 3.

Z can be —$CO_2R_{11}$, —$CONR_{10}R_{11}$, —C(=$NR_{10}$)$NR_{11}R_{12}$, —$CONH_2NH_2$, —CN, —$CH_2OH$, —$NR_{16}R_{17}$, $CONHCH(R_{20})CO_{12}$, phthalimide, pyrrolidine-2,5-dione, thiazolidine-2,4-dione, tetrazolyl, pyrrole, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —$CO_2CH_3$, —$CO_2H$, —$COCH_3$, and —CN; wherein said $C_1$ to $C_7$ amines are optionally substituted with one to two substituents independently selected from the group consisting of —OH, halogen, —$OCH_3$, and —C≡CH; and wherein said $C_3$ to $C_7$ cyclic amines are optionally substituted with one or two substituents independently selected from the group consisting of —OH —$CH_2OH$, —$CH_2OCH_3$, —$CO_2CH_3$, and —$CONH_2$.

A can be phenyl, or phenyl substituted by one to four groups independently selected from halogen, acyl, $C_1$ to $C_3$ alkyl, $C_1$ to $C_3$ alkoxy, hydroxy, halogen, —CN, —$NO_2$, $C_1$ to $C_3$ perfluoroalkyl, —$NR_{10}R_{11}$, —$CH_2NR_{10}R_{11}$, —$SR_{11}$, and $C_1$ to $C_2$ alkyl substituted with 1 to 3 fluorines; or A can be a heterocycle selected from pyrrole, pyridine, pyrimidine, thiophene, indole, oxazole, and furan, which may be optionally substituted by one to three groups independently selected from halogen, acyl, $C_1$ to $C_3$ alkyl, $C_1$ to $C_3$ alkoxy, hydroxy, —CN, —$NO_2$, $C_1$ to $C_3$ perfluoroalkyl, —$NR_{10}R_{11}$, —$CH_2NR_{10}R_{11}$, —$SR_{11}$, and $C_1$ to $C_2$ alkyl substituted with 1 to 3 fluorines.

$R_{3'}$, $R_{4'}$, $R_{5'}$ can be —H.

$R_{6'}$ can be hydrogen, $C_1$ to $C_4$ alkyl, $C_1$ to $C_4$ perfluoroalkyl, or halogen.

Each $R_8$ can be independently —H, or $C_1$ to $C_2$ alkyl.

Each $R_9$ can be independently —H, or $C_1$ to $C_2$ alkyl.

Each $R_{10}$ is independently —H, or $C_1$ to $C_3$ alkyl.

Each $R_{11}$ is independently —H, or $C_1$ to $C_3$ alkyl; or $R_{10}$ and $R_{11}$, when attached to the same atom, together with said atom form:

(i) a 5 to 7 membered saturated ring, optionally substituted by 1 to 2 groups independently selected from $C_1$ to $C_3$ alkyl, OH and $C_1$-$C_3$ alkoxy, or (ii) a 5 to 7 membered ring containing 1 or 2 heteroatoms, optionally substituted by 1 to 2 groups independently selected from $C_1$ to $C_3$ alkyl, OH and $C_1$-$C_3$ alkoxy;

Each $R_{12}$ is independently —H, or $C_1$ to $C_3$ alkyl.

Each $R_{14}$, and $R_{15}$ is, independently, $C_1$ to $C_7$ alkyl, $C_3$ to $C_8$ cycloalkyl, $C_2$ to $C_7$ alkenyl, $C_2$ to $C_7$ alkynyl, —OH, —F, $C_7$ to $C_{14}$ arylalkyl, where said arylalkyl is optionally substituted with 1 to 3 groups independently selected from $NO_2$, $C_1$ to $C_6$ alkyl, $C_1$ to $C_3$ perhaloalkyl, halogen and $C_1$ to $C_3$ alkoxy, or $R_{14}$ and $R_{15}$ together with the atom to which they are attached can form a 3 to 7 membered saturated ring.

Each $R_{16}$ and $R_{17}$ can be, independently, hydrogen, $C_1$ to $C_3$ alkyl, $C_1$ to $C_3$ alkenyl, $C_1$ to $C_3$ alkynyl, or $C_3$ to $C_8$ cycloalkyl, wherein said $C_1$ to $C_3$ alkyl is optionally substituted with one OH group; or $R_{16}$ and $R_{17}$, together with the atom to which they are attached, can form a 3 to 8 membered heterocycle which is optionally substituted with one or two substituents independently selected from the group consisting of $C_1$ to $C_3$ alkyl, —OH, $CH_2OH$, —$CH_2OCH_3$, —$CO_2CH_3$, and —$CONH_2$.

Each $R_{18}$ and $R_{19}$ is, independently $C_1$ to $C_3$ alkyl.

In certain embodiments:

$X_1$ can be a bond, —C(O)—, or —$CR_8R_9$—.

$R_{1'}$ can be $C_1$ to $C_6$ alkyl, $CF_3$, CN, phenyl, or phenyl substituted by one to four groups independently selected from $C_1$ to $C_2$ perfluoroalkyl, halogen, and $C_1$ to $C_2$ alkyl substituted with 1 to 3 fluorines, or $R_{1'}$ can be a heterocycle selected from thiophene, and furan, which may be optionally substituted with one to three groups independently selected from $C_1$ to $C_2$ perfluoroalkyl, halogen, and $C_1$ to $C_2$ alkyl substituted with 1 to 3 fluorines.

$X_2$ can be a bond.

$R_{2'}$ can be phenyl substituted by —W'$(CH_2)_j$A$(CH_2)_k$D$(CH_2)_p$Z, —W'$(CR_{18}R_{19})$A$(CH_2)_k$D$(CH_2)_p$Z, —C≡CA$(CH_2)_k$D$(CH_2)_p$Z, or —$(CH_2)_j$W'A$(CH_2)_k$D$(CH_2)_p$Z, and further optionally substituted with one or two groups independently selected from $C_1$ to $C_2$ perfluoroalkyl, halogen, and —CN, or $R_{2'}$ can be a heterocycle selected from pyridine, pyrimidine, thiophene, and furan which is substituted by —W'$(CH_2)_j$A$(CH_2)_k$D$(CH_2)_p$Z, —W'$(CR_{18}R_{19})$A$(CH_2)_k$D$(CH_2)_p$Z, or —$(CH_2)_j$W'A$(CH_2)_k$D$(CH_2)_p$Z.

D can be a bond, —O—, —NH—, —S—, —$CHR_{14}$—, —$OCR_{14}R_{15}$—, —$OCHR_{14}$—, or —$OCR_{14}R_{15}$—.

Z can be —$CO_2R_{11}$, —$CONR_{10}R_{11}$, —CN, —$CH_2OH$, or —$NR_{16}R_{17}$.

A can be phenyl, or phenyl substituted by one to four groups independently selected from halogen, —CN, $C_1$ to $C_3$ perfluoroalkyl, and $C_1$ to $C_2$ alkyl substituted with 1 to 3 fluorines, or A can be a heterocycle selected from pyrrole, pyridine, pyrimidine, and thiophene, each of which may be optionally substituted by one to three groups independently selected from halogen, —CN, $C_1$ to $C_3$ perfluoroalkyl, and $C_1$ to $C_2$ alkyl substituted with 1 to 3 fluorines.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species.

The compounds described herein can be synthesized according to methods described herein and/or conventional, organic chemical synthesis methods from commercially available starting materials and reagents. The compounds described herein can be separated from a reaction mixture and further purified by a method such as column chromatography, high-pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

In some embodiments, the cinnoline compounds described herein can generally be prepared as delineated in Schemes 1-7.

In some embodiments, cinnoline compounds having alkyl groups (e.g., C1 to C3 alkyl) as the substituent corresponding to $R^1$ in formula (I) can be prepared, e.g., according to Scheme 1. Compound 1 can be converted to the N-methyl, N-methoxy amide 2 ("Weinreb amide") under conventional amidation conditions. Reaction of the amide 2 with a lithio or Grignard reagent of formula $R_2Li$ or $R_2MgBr$ at low temperature can provide the ketone 3. Conversion of the ketone 3 into the aniline 4 can be accomplished with ammonium hydroxide at elevated temperature. Intermediate 5 is prepared by reacting 4 with $R_1XCH_2MgBr$ followed by dehydration, which typically can occur spontaneously. Cinnoline 6 (X=bond) can be prepared via diazotisation (e.g., $NaNO_2/HCl$) of the O-aminoaryl-ethylene 5 followed by a cyclization.

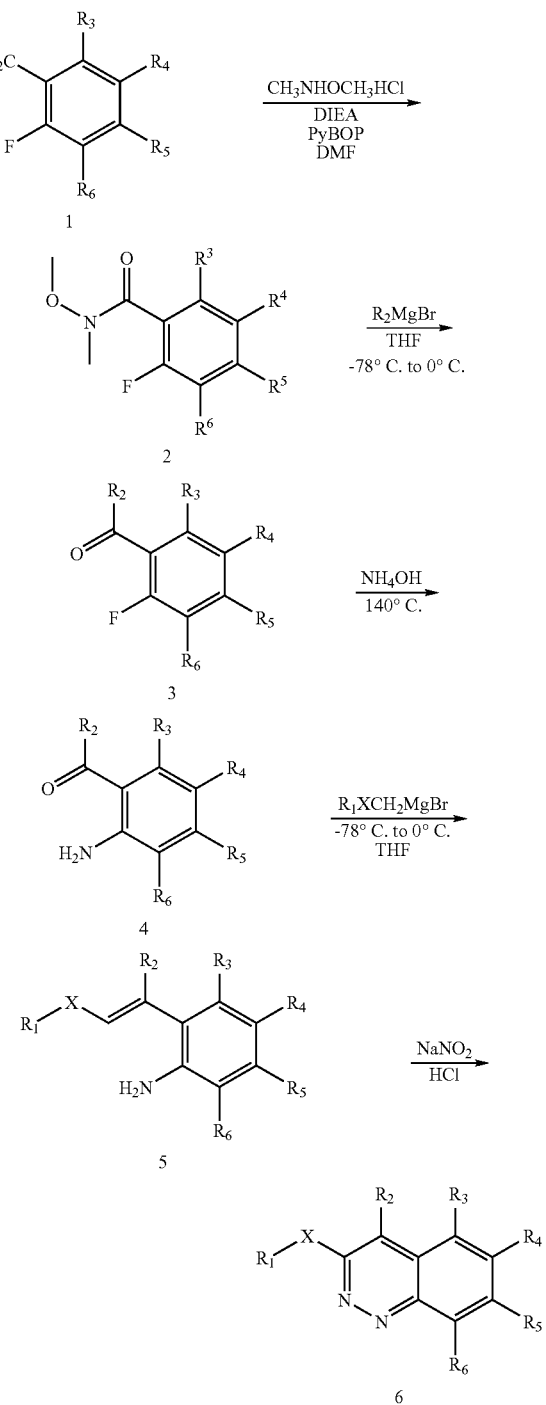

In some embodiments, cinnoline compounds having $R_1=R_2$ (i.e., the substituent corresponding to R1 in formula (I) is the same as the substituent corresponding to R1 in formula (I)) can be prepared, e.g., according to Scheme 2. The hydrazine compound 7 can be condensed with 1,2-diaryl-ethane-1,2-dione using conventional procedures to give hydrazone 8. Acid-mediated (e.g., $H_2SO_4$) cyclization of the hydrazone 8 can provide cinnoline 9.

Scheme 2

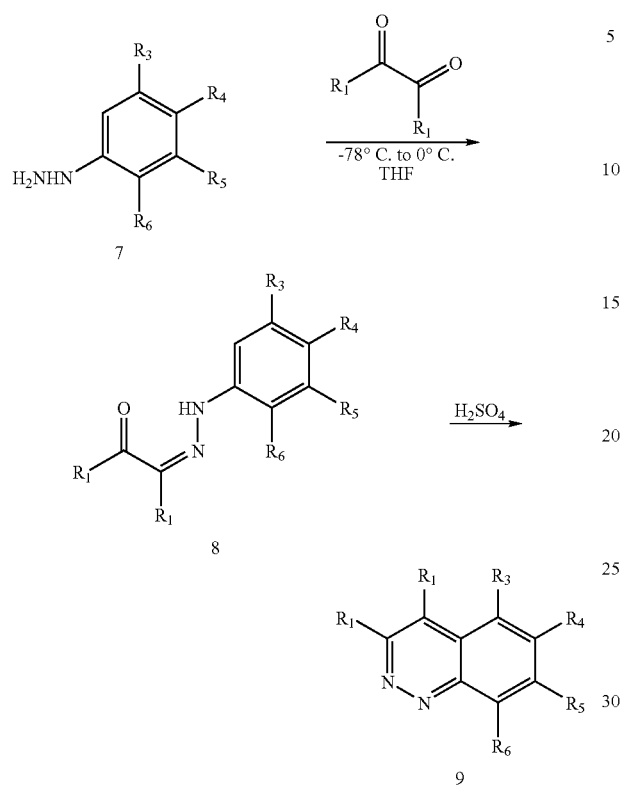

In some embodiments, the cinnoline compounds of formula (I) can also be prepared according to Scheme 3. The 4-hydroxy cinnoline 12 can be synthesized in two steps by Friedel-Crafts acylation of the aniline 10 followed by ring closure under the diazotisation conditions. Conversion to 13 can be effected with conventional halogenating agents, e.g., $POBr_3$ or $SOCl_2$. Reaction of 13 with a boronic acid reagent of formula $R_2B(OH)_2$ in the presence of a palladium catalyst can provide 14.

Scheme 3

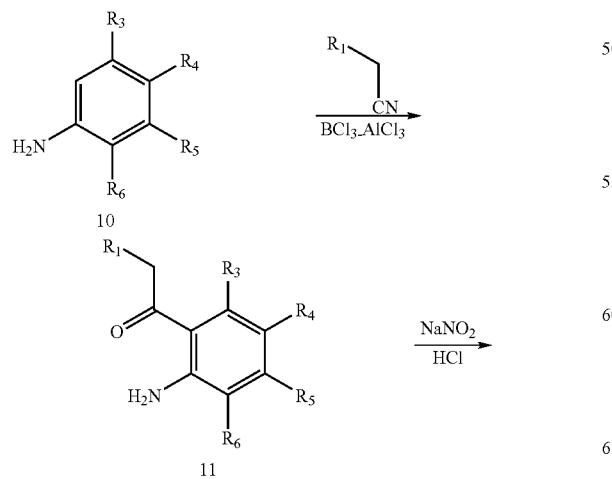

In some embodiments, cinnoline compounds having an amino-substituted aryl group as the substituent corresponding to $R^2$ in formula (I) can be prepared according to Scheme 4. Treatment of the free amine 15 with a sulfonyl chloride, an acid chloride or an isocyanate can provide compound 16, in which Y can be $SO_2$, CO, or CONH, and A can be, e.g. aryl (e.g., phenyl) (X=bond).

Scheme 4

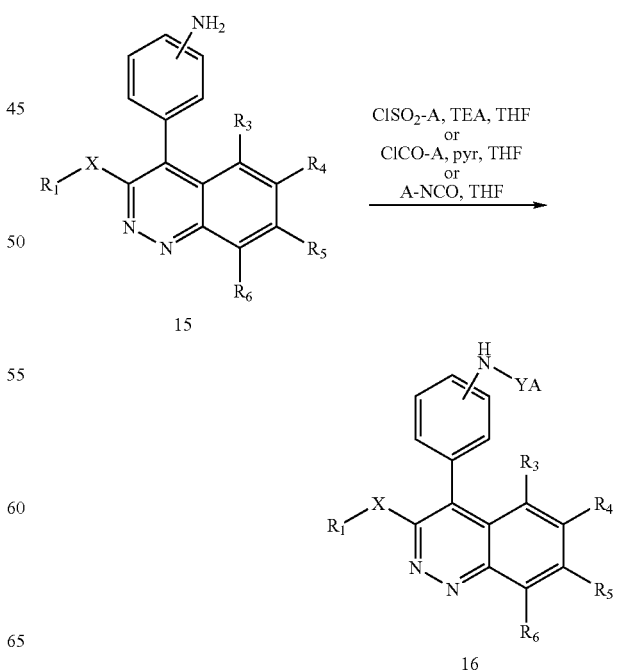

In some embodiments, compounds of formula (I) can be prepared according to Scheme 5. Treatment of the free amine 17, wherein j is 0-3, with an aldehyde (A-CHO) and a reducing agent such as NaBH(OAc)$_3$, can result in the secondary amine 18. Alternatively, the secondary amine 18 can also be obtained upon treating the starting primary amine 17 with an alkylating agent (e.g., A-X') in the presence of a base. If the A group of the compound of formula (I) contains a carboxylic acid ester moiety this moiety can be transformed to the carboxylic acid upon treatment with aqueous lithium, sodium or potassium hydroxide in water mixed with a suitable organic solvent (X=bond).

Scheme 5

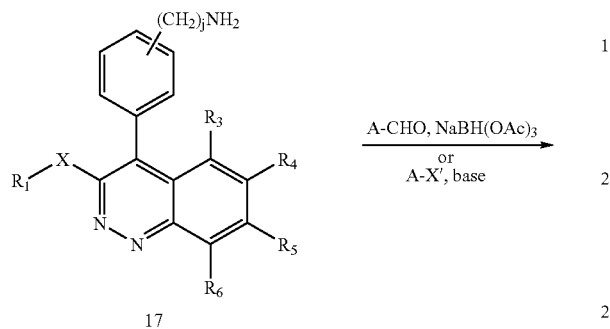

In some embodiments, compounds of formula (I) can be prepared according to Scheme 6. Alkylation of the hydroxy group of 19 with an alkylating agent (e.g., A-X') using potassium carbonate as the base can provide the alkylated compound 200 is 0-3). Alternatively, if j is 1 or more and A-OH is a phenol or substituted phenol, or, j is 0 and A-OH is an alcohol where the OH is connected to an sp3 hybridized carbon, then the alcohol of formula 19 and the A-OH can be reacted with triphenylphosphine (PPh$_3$) and diisopropylazodicarboxylate (DIAD) to form the ether of formula 20. If the A group of the compound of formula (I) contains a carboxylic acid ester moiety this moiety can be transformed to the carboxylic acid upon treatment with aqueous lithium, sodium or potassium hydroxide in a suitable organic solvent.

Scheme 6

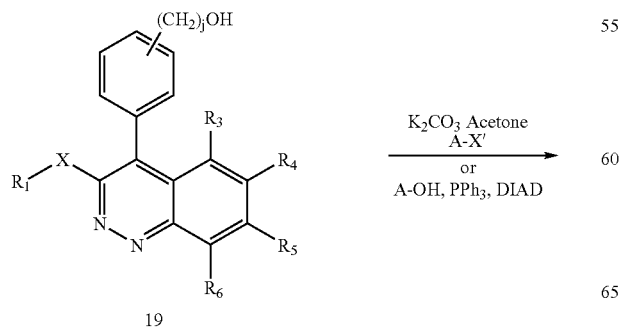

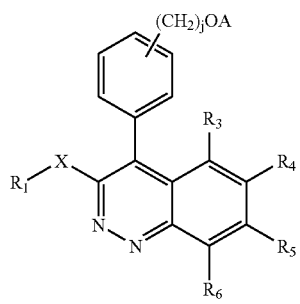

In some embodiments, the cinnoline compounds of formula (I) can also be prepared according to Scheme 7. The 4-hydroxy cinnoline 23 can be synthesized in two steps by Grignard reagent addition to the amide 21 followed by ring closure under the diazotisation conditions. Conversion to 24 can be effected with conventional halogenating agents, e.g., POBr$_3$ or SOCl$_2$. Reaction of 24 with a boronic acid reagent of formula R$_2$B(OH)$_2$ in the presence of a palladium catalyst can provide 25.

Scheme 7

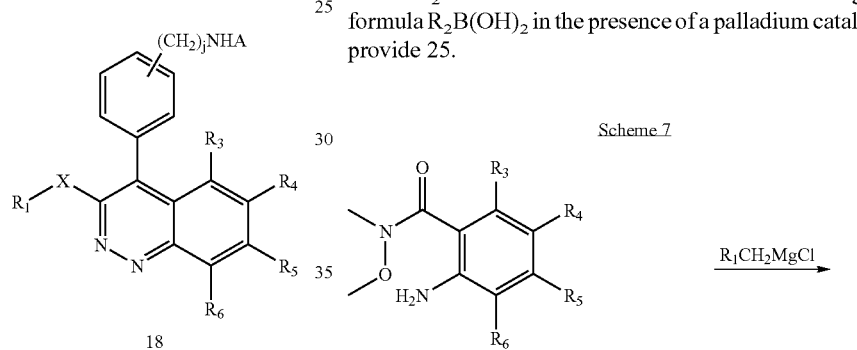

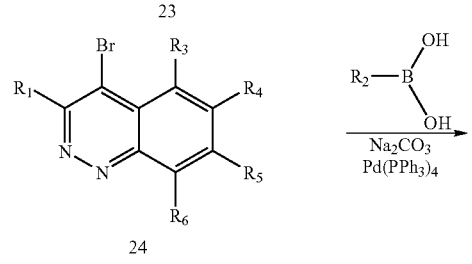

-continued

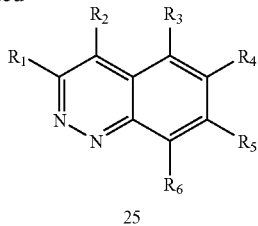

25

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also contain linkages (e.g., carbon-carbon bonds, carbon-nitrogen bonds such as amide bonds) wherein bond rotation is restricted about that particular linkage, e.g. restriction resulting from the presence of a ring or double bond. Accordingly, all cis/trans and E/Z isomers and rotational isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active compounds.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

The term "pharmaceutically acceptable carrier or adjuvant" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

In general, the compounds described herein can be used for treating, controlling, ameliorating, preventing, delaying the onset of, or reducing the risk of developing one or more diseases, disorders, conditions or symptoms mediated by LXRs (e.g., cardiovascular diseases (e.g., acute coronary syndrome, restenosis), atherosclerosis, atherosclerotic lesions, type I diabetes, type II diabetes, Syndrome X, obesity, lipid disorders (e.g., dyslipidemia, hyperlipidemia, hypertriglyceridemia, hypercholesterolemia, low HDL and high LDL), cognitive disorders (e.g., Alzheimer's disease, dementia), inflammatory diseases (e.g., multiple sclerosis, rheumatoid arthritis, inflammatory bowel disease, Crohn's disease, endometriosis, LPS-induced sepsis, acute contact dermatitis of the ear, chronic atherosclerotic inflammation of the artery wall), celiac, or thyroiditis)). A disorder or physiological condition that is mediated by LXR refers to a disorder or condition wherein LXR can trigger the onset of the condition, or where inhibition of a particular LXR can affect signaling in such a way so as to treat, control, ameliorate, prevent, delay the onset of, or reduce the risk of developing the disorder or condition. Examples of such disorders include, but are not limited to cardiovascular diseases (e.g., acute coronary syndrome, restenosis), atherosclerosis, atherosclerotic lesions, type I diabetes, type II diabetes, Syndrome X, obesity, lipid disorders (e.g., dyslipidemia, hyperlipidemia, hypertriglyceridemia, hypercholesterolemia, low HDL and high LDL), cognitive disorders (e.g., Alzheimer's disease, dementia), inflammatory diseases (e.g., multiple sclerosis, rheumatoid arthritis, inflammatory bowel disease, Crohn's disease, endometriosis, LPS-induced sepsis, acute contact dermatitis of the ear, chronic atherosclerotic inflammation of the artery wall), celiac, or thyroiditis).

While not wishing to be bound by theory, it is believed that LXR modulators that activate cholesterol efflux (e.g., upregulate ABCA1), but do not substantially increase SREBP-1c expression and triglyceride synthesis in liver, can both reduce atherosclerotic risk and minimize the likelihood of concomitantly increasing serum and hepatic triglyceride levels. Candidate compounds having differential activity for regulating ABCA1 (ABCG1) vs. SREBP-1c can be can be evaluated using conventional pharmacological test procedures, which measure the affinity of a candidate compound to bind to LXR and to upregulate the gene ABCA1.

In some embodiments, LXR ligands can be identified initially in cell-free LXR beta and LXR alpha competition binding assays. LXR ligands can be further characterized by gene expression profiling for tissue selective gene regulation.

In some embodiments, the compounds described herein have agonist activity for ABCA1 transactivation but do not substantially affect (e.g., inhibit) SREBP-1c gene expression in differentiated THP-1 macrophages. Gene expression analysis in an antagonist mode can be used to further delineate differential regulation of ABCA1 and SREBP-1c gene expression. In certain embodiments, the compounds described herein preferentially antagonize SREBP-1c activation (a marker for genes involved in cholesterol and fatty acid homeostasis) but do not substantially affect (e.g., have relatively minimal or additive effects) on ABCA1 gene expression or genes known to enhance HDL biogenesis (based on a competition assay with known potent synthetic LXR agonists). Cell type or tissue specificity may be further evaluated in additional cell lines, intestinal, CaCo2 or liver, HepG2 and Huh-7 cells where ABCA1 activity is believed to influence net cholesterol absorption and reverse cholesterol transport. The test procedures performed, and results obtained therefrom are described in the Examples section.

In some embodiments, the compounds described herein have agonist activity for ABCA1 and antagonist activity for SREBP-1c (e.g., as determined by gene specific modulation in cell based assays). In certain embodiments, the compounds described herein (in the agonist mode) have at least about 20% efficacy for ABCA1 activation by LXR and do not substantially agonize SREBP-1c (at most about 25% efficacy relative to a reference compound N-(2,2,2-trifluoro-ethyl)-N-[4-(2,2,2-trifluoro-1-hydroxy-1-trifluoromethyl-ethyl)-phenyl]-benzenesulfonamide (Schultz, Joshua R., Genes & Development (2000), 14(22), 2831-2838)). In certain embodiments, the compounds described herein (in the antagonist mode) do not substantially antagonize ABCA1 gene expression. While not wishing to be bound by theory, it is believed that there may be an additive effect on ABCA1 gene expression relative to the reference compound at their $EC_{50}$ concentration. In certain embodiments, the compounds described herein (in the antagonist mode) inhibited agonist-mediated SREBP-1c gene expression in a dose dependent fashion.

In some embodiments, the compounds described herein can be coadministered with one or more other threapeutic agents. In certain embodiments, the additional agents may be administered separately, as part of a multiple dose regimen, from the compounds of this invention (e.g., sequentially, e.g., on different overlapping schedules with the administration of one or more compounds of formula (I), (V) or (VI)). Alternatively, these agents may be part of a single dosage form, mixed together with the compounds of this invention in a single composition. In still another embodiment, these agents can be given as a separate dose that is administered at about the same time that one or more compounds of formula (I), (V) or (VI) are administered (e.g., simultaneously with the administration of one or more compounds of formula (I), (V) or (VI)). When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen.

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/Kg to about 1000 mg/Kg, (e.g., from about 0.01 to about 100 mg/kg, from about 0.1 to about 100 mg/Kg, from about 1 to about 100 mg/Kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of this invention is useful when the desired treatment involves areas or organs readily accessible by topical application. For application topically to the skin, the composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation.

Topically-transdermal patches are also included in this invention. Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

The invention will be further described in the following examples. It should be understood that these examples are for illustrative purposes only and are not to be construed as limiting this invention in any manner.

EXAMPLES

Representative compounds of this invention were evaluated in standard pharmacological test procedures which measured their affinity to bind to LXR and to upregulate the gene ABCA1, which causes cholesterol efflux from atherogenic cells, such as macrophages.

LXR activation can be critical for maintaining cholesterol homeostasis, but its coincident regulation of fatty acid metabolism may lead to increased serum and hepatic triglyceride levels. Selective LXR modulators that activate cholesterol efflux with minimal impact on SREBP-1c expression and triglyceride synthesis in liver would be expected to reduce atherosclerotic risk with an improved therapeutic index and minimize the potential for deleterious effects on metabolic balance. A method is described herein for identifying selective LXR ligands with differential activity for regulating ABCA1 (ABCG1) vs. SREBP-1c.

Accordingly, LXR ligands were identified initially in cell-free LXR beta and LXR alpha competition binding assays. LXR ligands were further characterized by gene expression profiling for tissue selective gene regulation. Selective LXR modulators demonstrate agonist activity for ABCA1 transactivation but exhibit no effect or inhibition of SREBP-1c gene expression in differentiated THP-1 macrophages. Gene expression analysis in an antagonist mode was used to further delineate differential regulation of ABCA1 and SREBP-1c gene expression. In a competition assay with known potent synthetic LXR agonists, selective LXR ligands preferentially antagonize SREBP-1c activation (a marker for genes involved in cholesterol and fatty acid homeostasis) but have minimal or additive effects on ABCA1 gene expression or genes known to enhance HDL biogenesis. Cell type or tissue specificity may be further evaluated in additional cell lines, intestinal, CaCo2 or liver, HepG2 and Huh-7 cells where ABCA1 activity influences net cholesterol absorption and reverse cholesterol transport.

The test procedures performed, and results obtained are briefly described below.

Ligand-Binding Test Procedure for Human LXRβ.

Ligand-binding to the human LXRβ was demonstrated for representative compounds of this invention by the following procedure.

Materials and Methods:
Buffer: 100 mM KCl, 100 mM TRIS (pH 7.4 at +4° C.), 8.6% glycerol, 0.1 mM PMSF*, 2 mM MTG*, 0.2% CHAPS (* not used in wash buffer)
Tracer: $^3$H T0901317
Receptor source: E. coli extract from cells expressing biotinylated hLXRβ. Extract was made in a similar buffer as above, but with 50 mM TRIS.

Day 1
Washed streptavidin and coated flash plates with wash buffer.
Diluted receptor extract to give Bmax ~4000 cpm and add to the wells.
Wrapped the plates in aluminum foil and stored them at +4° C. over night.

Day 2
Made a dilution series in DMSO of the test ligands.
Made a 5 nM solution of the radioactive tracer in buffer.
Mixed 250 µl diluted tracer with 5 µl of the test ligand from each concentration of the dilution series.
Washed the receptor-coated flash plates.
Added 200 µl per well of the ligand/radiolabel mixture to the receptor-coated flash plates.
Wrapped the plates in aluminum foil and incubate at +4° C. over night.

Day 3
Aspirated wells, and wash the flashed plates. Sealed the plate. Measured the remaining radioactivity in the plate.

Results:
Representative compounds of this invention had activity (IC50 values) in the LXRβ ligand binding assay in the range between 0.001 to 20 uM.

Quantitative Analysis of ABCA1 Gene Regulation in THP-1 Cells.

The compounds of formula (I) effect on the regulation of the ABCA1 gene was evaluated using the following procedure.

Materials and Methods

Cell culture: The THP-1 monocytic cell line (ATCC # TIB-202) was obtained from American Type Culture Collection (Manassas, Va.) and cultured in RPMI 1640 medium (Gibco, Carlsbad, Calif.) containing 10% FBS, 2 mM L-glutamine, and 55 uM beta-Mercaptoethanol (BME). Cells were plated in 96-well format at a density of $7.5\times10^4$ in complete medium containing 50-100 ng/ml phorbal 12,13-dibutyrate (Sigma, St. Louis, Mo.) for three days to induce differentiation into adherent macrophages. Differentiated THP-1 cells were treated with test compounds or ligands dissolved in DMSO (Sigma, D-8779) in culture medium lacking phorbal ester. Final concentrations of DMSO did not exceed 0.3% of the media volume. Dose response effects were measured in duplicate, in the range of 0.001 to 30 micromolar concentrations and treated cells were incubated for an additional 18 hrs prior to RNA isolation. Unstimulated cells treated with vehicle were included as negative controls on each plate. An LXR agonist reference, N-(2,2,2-trifluoro-ethyl)-N-[4-(2,2,2-trifluoro-1-hydroxy-1-trifluoromethyl-ethyl)-phenyl]-benzenesulfonamide (Schultz, Joshua R., Genes & Development (2000), 14(22), 2831-2838), was dosed at 1.0 uM and served as a positive control. In antagonist mode, the compound under study is analyzed in the presence of 150 nM GW3965, trifluoromethyl-benzyl)-(2,2-diphenyl-ethyl)-amino]-propoxy]-phenyl)-acetic acid (Collins, J. L., J. Med. Chem. (2000), 45:1963-1966.). Results of antagonist analysis are expressed as % antagonism and IC50 (in µM).

RNA isolation and quantitation: Total cellular RNA was isolated from treated cells cultured in 96-well plates using PrepStation 6100 (Applied Biosystems, Foster City, Calif.), according to the manufacturer's recommendations. RNA was resuspended in ribonuclease-free water and stored at −70° C. prior to analysis. RNA concentrations were quantitated with RiboGreen test procedure, #R-11490 (Molecular Probes, Eugene, Oreg.).

Gene expression analysis: Gene-specific mRNA quantitation was performed by real-time PCR with the Perkin Elmer Corp. chemistry on an ABI Prism 7700 Sequence detection system (Applied Biosystems, Foster City, Calif.) according to the manufacturer's instructions. Samples (50-100 ng) of total RNA were assayed in duplicate or triplicate in 50 µl reactions using one-step RT-PCR and the standard curve method to estimate specific mRNA concentrations. Sequences of gene-specific primer and probe sets were designed with Primer Express Software (Applied Biosystems, Foster City, Calif.). The human ABCA1 primer and probe sequences are: forward, CAACATGAATGCCATTTTCCAA (SEQ ID NO:1), reverse, ATAATCCCCTGAACCCAAGGA (SEQ ID NO:2), and probe, 6FAM-TAAAGCCATGCCCTCTGCAG-GAACA TAMRA (SEQ ID NO:3). RT and PCR reactions were performed according to PE Applied Biosystem's protocol for Taqman Gold RT-PCR or Qiagen's protocol for Quantitect probe RT-PCR. Relative levels of ABCA1 mRNA are normalized using GAPDH mRNA or 18S rRNA probe/primer sets purchased commercially (Applied Biosystems, Foster City, Calif.).

Statistics:
Mean, standard deviation and statistical significance of duplicate evaluations of RNA samples were assessed using ANOVA, one-way analysis of variance using SAS analysis.

Reagents:
GAPDH Probe and Primers—Taqman GAPDH Control Reagents 402869 or 4310884E 18S Ribosomal RNA—Taqman 18S Control Reagents 4308329 10 Pack Taqman PCR Core Reagent Kit 402930
Qiagen Quantitect probe RT-PCR 204443.

Results:

Representative compounds of this invention were shown upregulate the transcription of the ABCA1 gene in THP-1 cells (EC50 value) in range between 0.01 to 15 uM with efficacy values in the range of 20 to 250% when compared to the efficacy shown by 1.0 uM of the reference standard.

Quantitative Analysis of SREBP-1c Gene Regulation in THP-1 Cells.

The compounds of formula (II) effect on the regulation of the SREBP-1c gene was evaluated using the same procedure as described for ABCA1 however, a primer and probe set specific for human SREBP-1c was substituted in gene expression analysis. The human SREBP-1c primer and probe sequences are: forward, AGGGCGGGCGCAGAT (SEQ ID NO:4), reverse, GGTTGTTGATAAGCTGAAGCATGT (SEQ ID NO:5), and probe, 6FAM-TCGAAAGTGCAATC-CATGGCTCCG-TAMRA (SEQ ID NO:6).

Based on the results obtained in the standard pharmacological test procedures, the compounds of this invention can be useful in treating or inhibiting LXR mediated diseases. In particular, the compounds of this invention can be useful in the treatment and inhibition of atherosclerosis and atherosclerotic lesions, lowering LDL cholesterol levels, increasing HDL cholesterol levels, increasing reverse cholesterol transport, inhibiting cholesterol absorption, treatment or inhibition of Alzheimer's disease, type I diabetes, type II diabetes, multiple sclerosis, rheumatoid arthritis, acute coronary syndrome, restenosis, inflammatory bowel disease (IBD), Crohn's disease, endometriosis, celiac, and thyroiditis.

Example 1

3-Benzyl-4-phenyl-8-(trifluoromethyl)cinnoline

Step 1: A suspension of (2-fluoro-3-trifluoromethyl-phenyl)-phenyl-methanone (0.5 g, 1.87 mmol) in 10 ml of ammonium hydroxide (28%) was sealed in a heavy-welled Pyrex tube. The sealed tube was heated at 140° C. overnight. The reaction was poured into water/saturated ammonium chloride solution and extracted with ethyl acetate. The combined organics was dried over MgSO$_4$ and concentrated to give (2-amino-3-trifluoromethyl-phenyl)-phenyl-methanone as an oil (0.45 g, 90%). MS ESI (m/z) 266 ([M+H]$^+$);

Step 2: (2-Amino-3-trifluoromethyl-phenyl)-phenyl-methanone (0.26 g, 1.0 mmol) was taken into diethyl ether (20 mL) and phenyl ethyl magnesium chloride (1.5 mL, 1.5 mmol, 1.0 M solution in diethyl ether) was added dropwise and stirred at room temperature for 1 hour. The reaction was poured into water/saturated ammonium chloride solution and extracted with diethyl ether. The combined organics was dried over MgSO$_4$ and concentrated. The material was purified via column chromatography using 0~10% ethyl actetate in hexane as the eluent to yield 0.08 g (22%) of 2-(1,3-diphenyl-propenyl)-6-trifluoromethyl-phenylamine as an oil. MS ESI (m/z) 354.3 ([M+H]$^+$);

Step 3: 2-(1,3-Diphenyl-propenyl)-6-trifluoromethyl-phenylamine (0.08 g, 0.23 mmol) was dissolved in 5 mL of acetic acid, 4 mL of conc. hydrochloric acid in an ice bath. The mixture was treated with 2.5% of sodium nitrate in water. After addition the reaction was heated to ~40° C. for 20 min, basified with ammonium hydroxide, and extracted with diethyl ether. The combined organics was dried over MgSO$_4$ and concentrated. The material was purified by semi-preparative HPLC (Column: Phenomenex C18 Luna 2.1.6 mm×60 mm, 5 µM; Solvent A: Water (0.1% TFA buffer); Solvent B: Acetonitrile (0.1% TFA buffer); Solvent Gradient: Time 0: 0% B; 10 min: 100% B; Hold 100% B 5 min. Flow Rate: 22.5 mL/min). The product was collected based on UV absorption and concentrated to give the title compound as a brown solid. MS (ESI) m/z 365.

Example 2

8-Methyl-3,4-diphenylcinnoline

Step 1: A mixture of 2-methylphenyl hydrazine hydrochloride (0.79 g, 5.0 mmol) and 1,2-diphenyl-ethane-1,2-dione (1.05 g, 5 mmol) in 20 mL of glacial acetic acid was refluxed for 30 min. The reaction was poured into water and extracted with ethyl acetate. The combined organics was dried over MgSO$_4$ and concentrated to give 1.6 gram of 1,2-diphenylethane-1,2-dione (2-methylphenyl)-hydrazone as an orange solid. MS (ESI) m/z 315 ([M+H]$^+$);

Step 2: 1,2-Diphenylethane-1,2-dione (2-methylphenyl)-hydrazone (0.50 g, 1.59 mmol) was dissolved in 70% of sulfuric acid (10 mL) and the reaction was stirred at room temperature overnight. The reaction was poured into iced water and extracted with ethyl acetate. The combined organics was dried over MgSO$_4$ and concentrated. The material was purified via column chromatography using 5-100% ethyl actetate in hexane as the eluent to yield 0.025 g of the title compound as an orange solid. MS (ESI) m/z 297([M+H]$^+$); HRMS (ESI, [M+H]$^+$) 297.1406.

Example 3

3,4-Diphenyl-8-(trifluoromethyl)cinnoline

Step 1: 1,2-Diphenylethane-1,2-dione [2-(trifluoromethyl)phenyl]hydrazone was prepared from 2-trifluoromethylphenyl hydrazine and 1,2-diphenyl-ethane-1,2-dione according to the procedure of Step 1 Example 2. MS (ESI) m/z 369; MS (ESI) m/z 367;

Step 2: The title compound was prepared from 1,2-diphenylethane-1,2-dione [2-(trifluoromethyl)phenyl]hydrazone according to the procedure of Step 2 Example 2. MS (ESI) m/z 351.

Example 4

8-Bromo-3,4-diphenylcinnoline

Step 1: 1,2-Diphenylethane-1,2-dione (2-bromophenyl)hydrazone was prepared from 2-bromophenyl hydrazine and 1,2-diphenyl-ethane-1,2-dione according to the procedure of Step 1 Example 2. MS m/z 379;

Step 2: The title compound was prepared from 1,2-diphenylethane-1,2-dione (2-bromophenyl)hydrazone according to the procedure of Step 2 Example 2. HRMS (ESI, [M+H]$^+$) 361.0346.

Example 5

8-Chloro-3,4-diphenylcinnoline

Step 1: 1,2-Diphenylethane-1,2-dione (2-chlorophenyl)hydrazone was prepared from 2-chlorophenyl hydrazine and 1,2-diphenyl-ethane-1,2-dione according to the procedure of Step 1 Example 2. MS m/z 335;

Step 2: The title compound was prepared from 1,2-diphenylethane-1,2-dione (2-chlorophenyl)hydrazone according to the procedure of Step 2 Example 2. MS m/z 317; HRMS (ESI, [M+H]$^+$) 317.0833.

Example 6

[4-({[3-(8-Methyl-3-phenylcinnolin-4-yl)phenyl]amino}methyl)phenyl]acetic acid

Step 1: 2-Methyl phenylaniline (2.39 g, 23 mmol) in 25 mL of 1,2-dichloroethane was added dropwise to a solution of 25.3 mL (25.3 mmol) of BCl$_3$ in xylene at 0~5° C. 5.38 g (46 mmol) of benzyl cyanide and 3.37 g (25.3 mmol) of AlCl$_3$ were added to the suspension, and the reaction mixture was stirred at 80° C. for 20 hours and cooled to 0° C.; 2 N HCl was added to the mixture. The mixture was then refluxed for 30 min at 80° C. and extracted with dichloromethane. The organic phase was washed with 1 M NaOH, dried, and evaporated to yield 1.0 g of 1-(2-amino-3-methylphenyl)-2-phenylethanone as a gray solid. MS (ESI) m/z 226;

Step 2: A solution of sodium nitrite (0.20 g, 2.8 mmol) in water (0.5 mL) was added dropwise, to a solution of 1-(2-amino-3-methylphenyl)-2-phenylethanone (0.42 g, 1.9 mmol) in acetic acid (9 mL) and sulfuric acid (1.5 mL). After the solution was stirred for 20 min at 80° C., the solution was poured into iced water. After the pH was adjusted to 6 with 2 N sodium hydroxide. The aqueous layer was extracted with ethyl acetate. The combined organics was dried over MgSO$_4$ and concentrated. The material was purified via column chromatography using 5-50% ethyl actetate in hexane as the eluent to yield 0.10 g of 8-methyl-3-phenylcinnolin-4-ol as a gum. MS (ESI) m/z 237; HRMS (ESI, [M+H]$^+$) 237.102;

Step 3: 2 Drops of DMF was added to a suspension of 8-methyl-3-phenylcinnolin-4-ol (60 mg) in SOCl$_2$ (10 mL) and the reaction was refluxed for 0.5 hours. The reaction was concentrated, dilute with ethyl acetate and washed with water. The organic layer was dried over MgSO$_4$ and concentrated to give crude 4-chloro-8-methyl-3-phenyl-cinnoline which was used for the next reaction without further purification. MS (ESI) m/z 255, 257;

Step 4: Crude 4-chloro-8-methyl-3-phenyl-cinnoline was taken into DME/EtOH (5 mL/1 mL). Then 3-aminophenylboronic acid (0.078 g, 0.5 mmol) was added followed by 2 M Na$_2$CO$_3$ (0.5 mL, 1.0 mmol) and finally Pd(PPh$_3$)$_4$ (0.06 g, 0.05 mmol). The reaction was refluxed for 2 hours. The solvent was removed and the resulting material was purified via column chromatography using 5-50% ethyl acetate in hexane to elute out 0.03 g of 3-(8-methyl-3-phenyl-cinnolin-4-yl)-phenylamine. MS (ESI) m/z 312 ([M+H]$^+$);

Step 5: 3-(8-Methyl-3-phenyl-cinnolin-4-yl)-phenylamine (0.031 g, 0.1 mmol) and (4-formyl-phenyl)-acetic acid methyl ester (0.07 g, 0.4 mmol) were mixed in DMF (4 mL) and then treated with NaBH(OAc)$_3$ (0.43 g, 2.0 mml) and acetic acid (0.4 mL). After stirring at 40° C. for 4 hours the mixture was quenched with water and then extracted with ethyl acetate. The organic residue was purified by silica gel chromatography using 5-50% EtOAc/hexanes as eluent to provide (4-{[3-(8-methyl-3-phenyl-cinnolin-4-yl)-phenylamino]-methyl}-phenyl)-acetic acid methyl ester as a gum which was used for the next reaction. MS (EI) m/z 474;

Step 6: To a stirred solution of (4-{[3-(8-methyl-3-phenyl-cinnolin-4-yl)-phenylamino]-methyl}-phenyl)-acetic acid methyl ester in THF/methanol/water (2:1:1, 10 mL) was added lithium hydroxide monohydrate (0.1 g). The reaction was stirred at 40° C. for 1 hour. The reaction mixture was made acidic (pH 6) with glacial acetic acid, and the solid was collected and dried over P$_2$O$_5$ to give the title compound as an orange solid (0.02 g, 43% for Step 5 and Step 6). MS (ESI) m/z 460; HRMS (ESI, [M+H]$^+$) 460.2012.

Example 7

3-(8-Chloro-3-phenyl-cinnolin-4-yl)-phenylamine

Step 1: 1-(2-Amino-3-chlorophenyl)-2-phenylethanone was prepared from 2-chlorophenylaniline and benzyl cyanide according to the procedure of Step 1 Example 6. MS m/z 246 [M+H]$^+$;

Step 2: 8-Chloro-3-phenylcinnolin-4-ol was prepared from 1-(2-amino-3-chlorophenyl)-2-phenylethanone according to the procedure of Step 2 Example 6. MS m/z 257, 259 [M+H]$^+$;

Step 3: A solution of 8-chloro-3-phenylcinnolin-4-ol (2.40 g, 9.3 mol) and POBr$_3$ (10.0 g, 35 mmol) in DMF (100 mL) was heated to 50° C. for 2 hours. The reaction was poured into ice-water, adjusted to pH to ~10 by diluted ammonium hydroxide and extracted with ethyl acetate. The combined organics were concentrated to yield 4-bromo-8-chloro-3-phenyl-cinnoline (1.40 g) as a pale yellow solid. MS m/z 321, 323 [M+H]$^+$;

Step 4: The title compound was prepared from 4-bromo-8-chloro-3-phenyl-cinnoline according to the procedure of Step 4 Example 6 as a pale yellow solid. MS m/z 332, 334.

Example 8

(4-{[3-(8-Chloro-3-phenyl-cinnolin-4-yl)-phenylamino]-methyl}-phenyl)-acetic acid methyl ester The title compound was prepared from 3-(8-chloro-3-phenyl-cinnolin-4-yl)-phenylamine according to the procedure of Step 5 Example 6. MS m/z 494, 496.

Example 9

[4-({[3-(8-Chloro-3-phenylcinnolin-4-yl)phenyl]amino}methyl)phenyl]acetic acid

The title compound was prepared from (4-{[3-(8-chloro-3-phenyl-cinnolin-4-yl) -phenylamino]-methyl}-phenyl)-acetic acid methyl ester according to the procedure of Step 6 Example 6 as a yellow solid. MS (ES) m/z 477.9; HRMS (ESI, [M+H]$^+$) 480.1462.

Example 10

N-[3-(8-Chloro-3-phenylcinnolin-4-yl)phenyl]-N'-phenylurea

Phenyl isocyanate (0.075 g, 0.63 mmol) was added to a stirred solution of 3-(8-chloro-3-phenyl-cinnolin-4-yl)-phenylamine (0.025 g, 0.076 mmol) in 5 mL of ACN at room temperature. The reaction mixture was stirred for 3 hours and concentrated. The residue was purified by silica gel chromatography using 5-50% EtOAc/hexanes as eluent to provide 0.025 g of the title compound as a gray solid. HRMS (ESI, [M+H]$^+$) 451.1310.

Example 11

3-(8-Chloro-3-phenylcinnolin-4-yl)phenol

The title compound was prepared from 4-bromo-8-chloro-3-phenyl-cinnoline according to the procedure of Step 4 Example 6 as a pale yellow solid. MS (ES) m/z 330.9; HRMS (ESI, [M+H]$^+$) 333.0805.

Example 12

(4-{[3-(8-Chloro-3-phenylcinnolin-4-yl)phenoxy]methyl}phenyl)acetic acid

A mixture of 3-(8-chloro-3-phenylcinnolin-4-yl)phenol (0.05 g, 0.15 mmol), 4-bromomethylphenyl acetic acid (0.10 g, 0.44 mmol), sodium carbonate (0.50 g, 4.7 mmol), and potassium iodine (0.50 g, 3.0 mmol) in DMF (5 mL)/water (1 mL) was heated to 40° C. for 2 hours. The mixture was then poured into water, acidified with acetic acid and extracted with ethyl acetate. The organic residue was purified by semi-preparative HPLC (Column: Phenomenex C18 Luna 21.6 mm×60 mm, 5 µM; Solvent A: Water (0.1% TFA buffer); Solvent B: Acetonitrile (0.1% TFA buffer); Solvent Gradient: Time 0: 0% B; 10 min: 100% B; Hold 100% B 5 min. Flow Rate: 22.5 mL/min). The product was collected based on UV absorption and concentrated to give the title compound as a colored solid. MS (ESI) m/z 481; HRMS (ESI, [M+H]$^+$) 481.1329.

Example 13

3-(8-Chloro-3-methylcinnolin-4-yl)phenol

Step 1: 8-Chloro-3-methylcinnolin-4-ol was prepared from 2-chloroaniline and propionitrile according to the procedures of Step 1 Example 6 and Step 2 Example 6. MS (ES) m/z 195.0;

Step 2: 4-Bromo-8-chloro-3-methylcinnoline was prepared from 8-chloro-3-methylcinnolin-4-ol according the procedure of step 3 Example 7. MS (ES) m/z 256.8; HRMS (ESI, [M+H]$^+$) 256.9467;

Step 3: The title compound was prepared from 4-bromo-8-chloro-3-methylcinnoline according to the procedure of Step 4 Example 6. MS (ES) m/z 268.9; HRMS (ESI, [M+H]$^+$) 271.0631.

Example 14

Methyl (4-{[3-(8-chloro-3-methylcinnolin-4-yl)phenoxy]methyl}phenyl)acetate

A mixture of 3-(8-chloro-3-methylcinnolin-4-yl)phenol (0.21 g, 0.78 mmol), 4-bromomethylphenyl acetic acid methyl ester (0.42 g, 1.64 mmol), and cesium carbonate (1.70 g, 5.2 mmol) in acetone (15 mL) was refluxed for 2 hours. The reaction was quenched with water and extracted with ethyl acetate. The organic residue was purified by silica gel chromatography using 5-50% EtOAc/hexanes as eluent to provide the title compound (0.28 g) as a gum. MS (ESI) m/z 433; HRMS (ESI, [M+H]$^+$) 433.1335.

Example 15

(4-{[3-(8-Chloro-3-methylcinnolin-4-yl)phenoxy]methyl}phenyl)acetic acid

The title compound was prepared from methyl (4-{[3-(8-chloro-3-methylcinnolin-4-yl)phenoxy]methyl}phenyl)acetate according to the procedure of Step 6 Example 6. MS (ESI) m/z 419.

Example 16

[4-({[3-(8-Chloro-3-methylcinnolin-4-yl)phenyl]thio}methyl)phenyl]acetic acid

Step 1: 3-(4-Carboxymethyl-benzylsulfanyl)-phenylboronic acid was prepared from 3-mercaptophenylboronic acid and 4-bromomethylphenyl acetic acid according to the procedure of Example 12;

Step 2: The title compound was prepared from 3-(4-carboxymethyl-benzylsulfanyl)-phenylboronic acid and 4-bromo-8-chloro-3-methylcinnoline according to the procedure of Step 4 Example 6. MS (ESI) m/z 435; HRMS (ESI, [M+H]$^+$ 435.0924.

Example 17

2-(4-{[3-(8-Chloro-3-methylcinnolin-4-yl)phenoxy]methyl}phenyl)-2-methylpropanoic acid NaH (0.12 g, 60% in dispersion in mineral oil, 3 mmol) was added in 3 portions to a stirred solution of methyl (4-{[3-(8-chloro-3-methylcinnolin-4yl)phenoxy]methyl}phenyl)acetate (0.25 g, 0.58 mmol) at room temperature. The mixture was heated to reflux and iodomethane (1.5 mL, 24 mmol) was added in 3 porions. After 14 hours the reaction was quenched with water and extracted with ethyl acetate. The hydrolysis of crude ester followed by semi-preparative HPLC purifications gave the title compound as a pale yellow solid. MS (ESI) m/z 447.

Example 18

8-Chloro-4-{3-[(2,5-dimethylbenzyl)oxy]phenyl}-3-methylcinnoline

The title compound was prepared from 2,5-dimethylbenzyl bromide according the procedure of Example 14. MS (ES) m/z 389.1; HRMS (ESI, [M+H]$^+$) 389.1411.

Example 19

[3-(8-Chloro-3-phenylcinnolin-4-yl)phenyl](2,3-dimethylbenzyl)amine

The title compound was prepared from 3-(8-chloro-3-phenyl-cinnolin-4-yl)-phenylamine and 2,3-dimethylbenzaldehyde according to the procedure of Step 5 Example 6. MS (ES) m/z 450.2.

Example 20

[3-(8-Chloro-3-phenylcinnolin-4-yl)phenyl](2,5-dimethylbenzyl)amine

The title compound was prepared from 3-(8-chloro-3-phenyl-cinnolin-4-yl)-phenylamine and 2,5-dimethylbenzaldehyde according to the procedure of Step 5 Example 6. MS (ES) m/z 450.2.

Example 21

[3-(8-Chloro-3-phenylcinnolin-4-yl)phenyl](1-naphthylmethyl)amine

The title compound was prepared from 3-(8-chloro-3-phenyl-cinnolin-4-yl)-phenylamine and naphthalene-1-carbaldehyde according to the procedure of Step 5 Example 6. MS (ES) m/z 473.

Example 22

[3-(8-Chloro-3-phenylcinnolin-4-yl)phenyl](3,4-dichlorobenzyl)amine

The title compound was prepared from 3-(8-chloro-3-phenyl-cinnolin-4-yl)-phenylamine and 3,4-chlorobenzaldehyde according to the procedure of Step 5 Example 6. MS (ES) m/z 490.

Example 23

[3-(8-Chloro-3-phenylcinnolin-4-yl)phenyl][5-fluoro-2-(trifluoromethyl)benzyl]amine The title compound was prepared from 3-(8-chloro-3-phenyl-cinnolin-4-yl)-phenylamine and 5-fluoro-2-trifluoromethylbenzaldehyde according to the procedure of Step 5 Example 6. MS (ESI) m/z 506.

Example 24

[3-(8-chloro-3-phenylcinnolin-4-yl)phenyl][2-chloro-3-(trifluoromethyl)benzyl]amine The title compound was prepared from 3-(8-chloro-3-phenyl-cinnolin-4-yl)-phenylamine and 2-chloro-3-trifluoromethylbenzaldehyde according to the procedure of Step 5 Example 6. MS (ESI) m/z 522.

Example 25

Methyl 2-[4-({[3-(8-chloro-3-phenylcinnolin-4-yl)phenyl]amino}methyl)phenyl]-2-methylpropanoate The title compound was prepared from 3-(8-chloro-3-phenyl-cinnolin-4-yl)-phenylamine and 2-(4-formyl-phenyl)-2-methyl-propionic acid methyl ester according to the procedure of Step 5 Example 6. MS (ES) m/z 522.2.

Example 26

2-[4-({[3-(8-Chloro-3-phenylcinnolin-4-yl)phenyl]amino}methyl)phenyl]-2-methylpropanoic acid The title compound was prepared from methyl 2-[4-({[3-(8-chloro-3-phenylcinnolin-4-yl)phenyl]amino}methyl)phenyl]-2-methylpropanoate according to the procedure of Step 6 Example 6. MS (ES) m/z 506.2.

Example 27

4-{3-[(2-Bromo-5-methoxybenzyl)oxy]phenyl}-8-chloro-3-phenylcinnoline

The title compound was prepared from 3-(8-chloro-3-phenyl-cinnolin-4-yl)-phenylamine and 2-bromo-5-methoxyl-benzaldehyde according to the procedure of Step 5 Example 6. MS (ES) m/z 531.1.

Example 28

8-Chloro-4-(3-{[5-chloro-2-(trifluoromethyl)benzyl]oxy}phenyl)-3-phenylcinnoline The title compound was prepared from 3-(8-chloro-3-phenyl-cinnolin-4-yl)-phenylamine and 5-chloro-2-trifluoromethylbenzaldehyde according to the procedure of Step 5 Example 6. MS (ES) m/z 525.1.

Example 29

8-Chloro-4-{3-[(3,4-dichlorobenzyl)oxy]phenyl}-3-phenylcinnoline

The title compound was prepared from 3-(8-chloro-3-phenyl-cinnolin-4-yl)-phenylamine and 3,4-dichlorobenzaldehyde according to the procedure of Step 5 Example 6. MS (ES) m/z 491.1.

Example 30

[3-(3-Benzyl-8-chlorocinnolin-4-yl)phenyl][5-fluoro-2-(trifluoromethyl)benzyl]amine The title compound was prepared from [3-(3-benzyl-8-chlorocinnolin-4-yl)phenyl]amine and 5-fluoro-3-trifluoromethylbenzaldehyde according to the procedure of Step 5 Example 6. MS (ES) m/z 522.1.

Example 31

[3-(8-Chloro-3-phenylcinnolin-4-yl)phenyl][(1-methyl-1H-indol-2-yl)methyl]amine

The title compound was prepared from 3-(8-chloro-3-phenyl-cinnolin-4-yl)-phenylamine and 1-methyl-1H-indole-2-carbaldehyde according to the procedure of Step 5 Example 6. MS (ES) m/z 474.9.

Example 32

[3-(3-Benzyl-8-chlorocinnolin-4-yl)phenyl]amine

The title compound was prepared from 2-chlorophenylamine and hydrocinnamontrile according to the procedure of Example 7. MS (ESI) m/z 346.

Example 33

[3-(3-Benzyl-8-chlorocinnolin-4-yl)phenyl][2-chloro-3-(trifluoromethyl)benzyl]amine The title compound was prepared from [3-(3-benzyl-8-chlorocinnolin-4-yl)phenyl]amine and 2-chloro-3-trifluoromethylbenzaldehyde according to the procedure of Step 5 Example 6. MS (ESI) m/z 538.

Example 34

[3-(3-Benzyl-8-chlorocinnolin-4-yl)phenyl](2,3-dimethylbenzyl)amine

The title compound was prepared from [3-(3-benzyl-8-chlorocinnolin-4-yl)phenyl]amine and 2,3-dimethylbenzaldehyde according to the procedure of Step 5 Example 6. MS (ESI) m/z 464.

Example 35

[3-(3-Benzyl-8-chlorocinnolin-4-yl)phenyl][5-chloro-2-(trifluoromethyl)benzyl]amine The title compound was prepared from [3-(3-benzyl-8-chlorocinnolin-4-yl)phenyl]amine and 5-chloro-2-trifluoromethylbenzaldehyde according to the procedure of Step 5 Example 6. MS (ESI) m/z 538.

Example 36

[3-(8-Chloro-3-phenylcinnolin-4-yl)phenyl](2-naphthylmethyl)amine

The title compound was prepared from 3-(8-chloro-3-phenyl-cinnolin-4-yl)-phenylamine and naphthalene-2-carbaldehyde according to the procedure of Step 5 Example 6. MS (ES) m/z 471.9.

Example 37

[3-(8-Chloro-3-phenylcinnolin-4-yl)phenyl][5-chloro-2-(trifluoromethyl)benzyl]amine The title compound was prepared from 3-(8-chloro-3-phenyl-cinnolin-4-yl)-phenylamine and 5-chloro-2-trifluoromethylbenzaldehyde according to the procedure of Step 5 Example 6. MS (ES) m/z 523.9.

Example 38

[3-(8-Chloro-3-phenylcinnolin-4-yl)phenyl][2-fluoro-5-(trifluoromethyl)benzyl]amine The title compound was prepared from 3-(8-chloro-3-phenyl-cinnolin-4-yl)-phenylamine and 2-fluoro-5-trifluoromethylbenzaldehyde according to the procedure of Step 5 Example 6. MS (ES) m/z 507.9.

Example 39

N-(5-Bromo-2-fluorobenzyl)-3-(8-chloro-3-phenyl-cinnolin-4-yl)aniline

The title compound was prepared from 3-(8-chloro-3-phenyl-cinnolin-4-yl)-phenylamine and 5-bromo-2-fluorobenzaldehyde according to the procedure of Step 5 Example 6. MS (ES) m/z 517.9.

Example 40

N-(5-Bromo-2-methoxybenzyl)-3-(8-chloro-3-phenylcinnolin-4-yl)aniline

The title compound was prepared from 3-(8-chloro-3-phenyl-cinnolin-4-yl)-phenylamine and 5-bromo-2-methoxybenzaldehyde according to the procedure of Step 5 Example 6. MS (ES) m/z 529.9.

Example 41

[3-(8-Chloro-3-phenylcinnolin-4-yl)phenyl][2-fluoro-3-(trifluoromethyl)benzyl]amine The title compound was prepared from 3-(8-chloro-3-phenyl-cinnolin-4-yl)-phenylamine and 2-fluoro-3-trifluorobenzaldehyde according to the procedure of Step 5 Example 6. MS (ES) m/z 507.9.

Example 42

N-[2,5-Bis(trifluoromethyl)benzyl]-3-(8-chloro-3-phenylcinnolin-4-yl)aniline

The title compound was prepared from 3-(8-chloro-3-phenyl-cinnolin-4-yl)-phenylamine and 2,5-bis(trifluoromethyl)benzaldehyde according to the procedure of Step 5 Example 6. MS (ES) m/z 558.0.

Example 43

[3-(3-Benzyl-8-chlorocinnolin-4-yl)phenyl](1-naphthylmethyl)amine

The title compound was prepared from [3-(3-benzyl-8-chlorocinnolin-4-yl)phenyl]amine and naphthalene-1-carbaldehyde according to the procedure of Step 5 Example 6. MS (ES) m/z 486.1.

Example 44

N-(2-Bromo-5-methoxybenzyl)-3-(8-chloro-3-phenylcinnolin-4-yl)aniline

The title compound was prepared from 3-(8-chloro-3-phenyl-cinnolin-4-yl)-phenylamine and 2-bromo-5-methoxybenzaldehyde according to the procedure of Step 5 Example 6. MS (ES) m/z 530.0.

Example 45

[3-(3-Benzyl-8-chlorocinnolin-4-yl)phenyl][(1-methyl-1H-indol-2-yl)methyl]amine

The title compound was prepared from [3-(3-benzyl-8-chlorocinnolin-4-yl)phenyl]amine and 1-methyl-1H-indole-2-carbaldehyde according to the procedure of Step 5 Example 6. MS (ES) m/z 489.1.

Example 46

[3-(8-Chloro-3-phenylcinnolin-4-yl)phenyl][(1-methyl-1H-indol-7-yl)methyl]amine

The title compound was prepared from 3-(8-chloro-3-phenyl-cinnolin-4-yl)-phenylamine and 1-methyl-1H-indole-7-carbaldehyde according to the procedure of Step 5 Example 6. MS (ES) m/z 474.9.

Example 47

[3-(3-Benzyl-8-chlorocinnolin-4-yl)phenyl](3,4-dichlorobenzyl)amine

The title compound was prepared from [3-(3-benzyl-8-chlorocinnolin-4-yl)phenyl]amine and 3,4-dichlorobenzaldehyde according to the procedure of Step 5 Example 6. MS (ES) m/z 504.6.

Example 48

[3-(8-Chloro-3-phenylcinnolin-4-yl)phenyl][(3-methyl-1-benzothien-2-yl)methyl]amine The title compound was prepared from [3-(3-benzyl-8-chlorocinnolin-4-yl)phenyl]amine and 3-methyl-benzo[b]

thiophene-2-carbaldehyde according to the procedure of Step 5 Example 6. MS (ES) m/z 492.2.

Example 49

8-Chloro-4-(3-{[3-(morpholin-4-ylcarbonyl)benzyl]oxy}phenyl)-3-phenylcinnoline

Step 1: 3-[3-(8-Chloro-3-phenyl-cinnolin-4-yl)-phenoxymethyl]-benzoic acid methyl ester was prepared from 3-(8-chloro-3-phenyl-cinnolin-4-yl)-phenol and 3-bromomethyl-benzoic acid methyl ester according to the procedure of Example 14. MS (ES) m/z 480.8;

Step 2: A solution of trimethylaluminum (2 M solution in dichloromethane, 0.5 M) was added to a solution of morpholine (0.1 g) in 5 mL of toluene at room temperature. After 30 minutes 3-[3-(8-chloro-3-phenyl-cinnolin-4-yl)-phenoxymethyl]-benzoic acid methyl ester (50 mg) in 2 mL of toluene was added and the solution was heated to 60° C. for 15 hours. The reaction mixture was cooled to room temperature, quenched with diluted HCl and extracted with ethyl acetate. The combined organic extracts were washed with brine, dried (MgSO$_4$), and concentrated in vacuo. The residue was purified by semi-preparative HPLC. MS (ES) m/z 536.2.

Example 49

N-(1-Benzothien-2-ylmethyl)-3-(8-chloro-3-phenyl-cinnolin-4-yl)aniline

The title compound was prepared from 3-(8-chloro-3-phenyl-cinnolin-4-yl)-phenylamine and benzo[b]thiophene-2-carbaldehyde according the procedure of Example 5 Step 5. MS (ES) m/z 478.1.

Example 50

N-(1-Benzothien-3-ylmethyl)-3-(8-chloro-3-phenyl-cinnolin-4-yl)aniline

The title compound was prepared from 3-(8-chloro-3-phenyl-cinnolin-4-yl)-phenylamine and benzo[b]thiophene-3-carbaldehyde according the procedure of Example 5 Step 5. MS (ES) m/z 478.0;

Example 51

[3-(8-Chloro-3-phenylcinnolin-4-yl)phenyl]{[4-(trifluoromethyl)-1-benzothien-2-yl]methyl}amine The title compound was prepared from 3-(8-chloro-3-phenyl-cinnolin-4-yl)-phenylamine and 4-trifluoromethyl-benzo[b]thiophene-2-carbaldehyde according the procedure of Example 5 Step 5. MS (ESI) m/z 546.

Example 52

3-(3-Benzyl-8-chlorocinnolin-4-yl)phenol

The title compound was prepared from 2-chloroaniline and hydrocinnamonitrile according the procedure of Example 13. MS (ES) m/z 347.

Example 53

3-Benzyl-4-[3-(benzyloxy)phenyl]-8-chlorocinnoline

The title compound was prepared from 3-(8-chloro-3-phenyl-cinnolin-4-yl)-phenol and benzyl bromide according the procedure of Example 14. MS (ES) m/z 436.8.

Example 54

3-Benzyl-8-chloro-4-(3-{[5-chloro-2-(trifluoromethyl)benzyl]oxy}phenyl)cinnoline The title compound was prepared from 3-(8-chloro-3-phenyl-cinnolin-4-yl)-phenol and 5-chloro-2-(trifluoromethyl)benzyl bromide according the procedure of Example 14. MS (ES) m/z 539.0.

Example 55

3-Benzyl-8-chloro-4-{3-[(1-methyl-1H-indol-7-yl)methoxy]phenyl}cinnoline

A mixture of 3-(8-chloro-3-phenyl-cinnolin-4-yl)-phenol (0.045 g, 0.13 mmol), polymer supported PPh$_3$ (0.3 g, ~1 mmol) in methylenechloride (5 mL) was stirred at room temperature for 30 minutes. (1-Methyl-1H-indol-7-yl)-methanol (0.045 g, 0.28 mmol) and DIAD (0.045 g, 0.23 mmol) in 1 mL of methylenechloride was added drop wise. After 1 hr, the reaction was filtered, concentrated and purified by semi-preparative HPLC to give a pale yellowish solid (0.025 g). MS (ESI) m/z 490.

Example 56

3-Benzyl-8-chloro-4-(3-{[2-chloro-3-(trifluoromethyl)benzyl]oxy}phenyl)cinnoline The title compound was prepared from 3-(8-chloro-3-phenyl-cinnolin-4-yl)-phenol and (2-chloro-3-trifluoromethylphenyl)-methanol according the procedure of Example 55. MS (ES) m/z 538.7.

Example 57

3-Benzyl-8-chloro-4-(3-{[2-fluoro-3-(trifluoromethyl)benzyl]oxy}phenyl)cinnoline The title compound was prepared from 3-(8-chloro-3-phenyl-cinnolin-4-yl)-phenol and (2-fluoro-3-(trifluoromethylphenyl)-methanol according the procedure of Example 55. MS (ES) m/z 522.8.

Example 58

3-Benzyl-8-chloro-4-{3-[(2-chlorobenzyl)oxy]phenyl}cinnoline

The title compound was prepared from 3-(8-chloro-3-phenyl-cinnolin-4-yl)-phenol and 2-chlorobenzyl bromide according the procedure of Example 14. MS (ES) m/z 470.8.

Example 59

3-Benzyl-8-chloro-4-(3-{[3-(trifluoromethyl)benzyl]oxy}phenyl)cinnoline

The title compound was prepared from 3-(8-chloro-3-phenyl-cinnolin-4-yl)-phenol and 3-trifluoromethylbenzyl bromide according the procedure of Example 14. MS (ES) m/z 504.8.

Example 60

3-Benzyl-8-chloro-4-(3-{[5-fluoro-2-(trifluoromethyl)benzyl]oxy}phenyl)cinnoline The title compound was prepared from 3-(8-chloro-3-phenyl-cinnolin-4-yl)-phenol and 5-fluoro-2-trifluoromethyl-benzyl bromide according the procedure of Example 14. MS (ES) m/z 523.0.

Example 61

N-[3-(3-Benzyl-8-chlorocinnolin-4-yl)phenyl]-N-[(1-methyl-1H-indol-7-yl)methyl]amine The title compound was prepared from 3-(3-benzyl-8-chloro-cinnolin-4-yl)-phenylamine and 1-methyl-1H-indole-7-carbaldehyde according the procedure of Example 5 Step 5. MS (ESI) m/z 489.

Example 62

3-(3-Benzyl-8-trifluoromethyl-cinnolin-4-yl)-phenol

Step 1: To a cooled (0° C.) solution of 2-fluoro-N-methoxy-N-methyl-3-trifluoromethyl-benzamide (5.0 g, 20 mmol) in THF (50 ml) was added phenethyl magnesium chloride (50 ml of 1.0M in THF) and the reaction was warmed to r.t. After 2 hr, the reaction was poured into 2N HCl and extracted with ether. The organic layer was dried ($MgSO_4$), and concentrated and the product was purified by column chromatography (eluent 5% EtOAc/Hexane) to give 1-(2-fluoro-3-trifluoromethyl-phenyl)-3-phenyl-propan-1-one as a clear oil (4.8 g). MS (ES) m/z 297.0.

Step 2: A solution of 1-(2-fluoro-3-trifluoromethyl-phenyl)-3-phenyl-propan-1-one (4.8 g, 16.2 mmol) and ammonium hydroxide (150 ml of 30% solution) in DME (50 ml) was heated to 140° C. in a steel pressure reactor. After 3 hr, the reaction was cooled to 0° C., the steel pressure reactor was opened and the reaction was partitioned between water and EtOAc. The organic layer was dried ($MgSO_4$) and concentrated to give 1-(2-amino-3-trifluoromethyl-phenyl)-3-phenyl-propan-1-one as a yellow oil (4.3 g). MS (ES) m/z 293.9.

Step 3: To a solution of 1-(2-amino-3-trifluoromethyl-phenyl)-3-phenyl-propan-1-one (4.2 g, 13.8 mmol) in AcOH (70 ml) and $H_2SO_4$ (10 ml) was added a solution of $NaNO_2$ (1.8 g in 10 ml $H_2O$). The reaction was then heated to 70° C. After 1.5 hr, the reaction was cooled, poured into water and extracted with EtOAc. The organic layer was dried ($MgSO_4$) and concentrated to give 3-benzyl-8-trifluoromethyl-cinnolin-4-ol As a dark solid which was triturated with 20% ether/hexane and collected by filtration (1.7 g). MS (ES) m/z 305.1.

Step 4: A solution of 3-benzyl-8-trifluoromethyl-cinnolin-4-ol (1.6 g, 4.4 mmol) and $POBr_3$ (2.5 g, 8.7 mmol) in DMF (30 ml) was heated to 75° C. After 1 hr, the reaction was cooled and poured into water. The aqueous layer was extracted with EtOAc which was dried ($MgSO_4$) and concentrated to give a solid. The solid was triturated with MeOH and filtered to give 3-benzyl-4-bromo-8-trifluoromethyl-cinnoline (1.7 g). MS (ES) m/z 366.7.

Step 5: A solution of 3-benzyl-4-bromo-8-trifluoromethyl-cinnoline (1.7 g, 4.6 mmol) and 3-hydroxyphenylboronic acid (0.84 g, 6.0 mmol) and $Pd(PPh_3)_4$ (300 mg) and $K_3PO_4$ (3.0 g) in dioxane (50 ml) was heated to reflux. After 6 hr, the reaction was cooled and poured into water and extracted with EtOAc. The organic layer was concentrated and the product purified by colum chromatography (eluent 10% EtOAc/Hexane) to give a solid 1.3 g. MS (ES) m/z 381.1.

Example 63

3-Benzyl-4-(3-fluoro-phenyl)-8-trifluoromethyl-cinnoline

The title compound was made in the same manner as Example 62 Step 5 except using 3-fluorophenylboronic acid as the coupling reagent. MS (ES) m/z 382.8.

Example 64

3-Benzyl-4-(4-fluoro-phenyl)-8-trifluoromethyl-cinnoline

The title compound was made in the same manner as Example 62 Step 5 except using 4-fluorophenylboronic acid as the coupling reagent. MS (ES) m/z 382.9

Example 65

3-Benzyl-4-(2-fluoro-phenyl)-8-trifluoromethyl-cinnoline

The title compound was made in the same manner as Example 62 Step 5 except using 2-fluorophenylboronic acid as the coupling reagent. MS (ES) m/z 382.8.

Example 66

3-Benzyl-8-trifluoromethyl-4-(4-trifluoromethyl-phenyl)-cinnoline

The title compound was made in the same manner as Example 62 Step 5 except using 4-trifluoromethylphenylboronic acid as the coupling reagent. MS (ES) m/z 432.9.

Example 67

3-Benzyl-4-(3-chloro-4-fluoro-phenyl)-8-trifluoromethyl-cinnoline

The title compound was made in the same manner as Example 62 Step 5 except using 3-chloro-4-fluorophenylboronic acid as the coupling reagent. MS (ES) m/z 416.8.

Example 68

3-Benzyl-4-(3-trifluoromethyl-phenyl)-8-trifluoromethyl-cinnoline

The title compound was made in the same manner as Example 62 Step 5 except using 3-trifluoromethylphenylboronic acid as the coupling reagent. MS (ES) m/z 432.9.

Example 69

3-Benzyl-4-(3-methoxy-phenyl)-8-trifluoromethyl-cinnoline

The title compound was made in the same manner as Example 62 Step 5 except using 3-methoxyphenylboronic acid as the coupling reagent. MS (ES) m/z 394.8.

Example 70

3-Benzyl-4-(3-chlorophenyl)-8-trifluoromethyl-cinnoline

The title compound was made in the same manner as Example 62 Step 5 except using 3-chlorophenylboronic acid as the coupling reagent. MS (ES) m/z 398.8.

Example 71

3-Benzyl-4-(4-methoxyphenyl)-8-trifluoromethyl-cinnoline

The title compound was made in the same manner as Example 62 Step 5 except using 4-methoxyphenylboronic acid as the coupling reagent. MS (ES) m/z 394.9.

Example 72

3-(8-Trifluoromethyl-cinnolin-4-yl)-phenol

The title compound was made in the same manner as Example 62 Step 5 except using 3-hydroxyphenylboronic acid as the coupling reagent and 4-chloro-8-trifluoromethyl-cinnoline as the chloride. MS (ES) m/z 291.0.

Example 73

3-Benzyl-4-(3-{[5-chloro-2-(trifluoromethyl)benzyl]oxy}phenyl)-8-(trifluoromethyl)cinnoline The title compound was made by the method shown in scheme 6. A solution of 3-(3-benzyl-8-trifluoromethyl-cinnolin-4-yl)-phenol (190 mg, 0.5 mmol), 5-chloro-2-trifluorobenzyl bromide (270 mg, 1 mmol) and $K_2CO_3$ (350 mg) in acetone (10 ml) was heated to reflux. After 4 hr, the reaction was cooled, filtered and concentrated. The product was purified by column chromatography (eluent 10% EtOAc/Hexane) to give a white foam (0.12 g). MS (ES) m/z 573.1.

Example 74

3-Benzyl-4-(3-{[2-(trifluoromethoxy)benzyl]oxy}phenyl)-8-(trifluoromethyl)cinnoline The title compound was made in the same manner as example 73 except using 2-trifluoromethoxybenzyl bromide as the alkylating reagent. MS (ES) m/z 555.1.

Example 75

3-Benzyl-4-(3-{[5-fluoro-2-(trifluoromethyl)benzyl]oxy}phenyl)-8-(trifluoromethyl)cinnoline The title compound was made in the same manner as example 73 except using 2-trifluoromethyl-5-fluorobenzyl bromide as the alkylating reagent. MS (ES) m/z 557.2.

Example 76

3-Benzyl-4-{3-[(2,5-dichlorobenzyl)oxy]phenyl}-8-(trifluoromethyl)cinnoline

The title compound was made in the same manner as example 73 except using 2,5-dichlorobenzyl bromide as the alkylating reagent. MS (ES) m/z 539.0.

Example 77

3-Benzyl-4-{3-[(2,6-dichlorobenzyl)oxy]phenyl}-8-(trifluoromethyl)cinnoline

The title compound was made in the same manner as example 73 except using 2,6-dichlorobenzyl bromide as the alkylating reagent. MS (ES) m/z 539.0.

Example 78

3-Benzyl-4-(3-{[2-fluoro-3-(trifluoromethyl)benzyl]oxy}phenyl)-8-(trifluoromethyl)cinnoline The title compound was made in the same manner as example 73 except using 3-trifluoromethyl-2-fluorobenzyl bromide as the alkylating reagent. MS (ES) m/z 557.0.

Example 79

3-Benzyl-4-(3-{[2-chloro-3-(trifluoromethyl)benzyl]oxy}phenyl)-8-(trifluoromethyl)cinnoline The title compound was made in the same manner as example 73 except using 3-trifluoromethyl-2-chlorobenzyl bromide as the alkylating reagent. MS (ES) m/z 573.1.

Example 80

3-Benzyl-4-{3-[(3,4-dichlorobenzyl)oxy]phenyl}-8-(trifluoromethyl)cinnoline

The title compound was made in the same manner as example 73 except using 3,4-dichlorobenzyl bromide as the alkylating reagent. MS (ES) m/z 539.0.

Example 81

3-Benzyl-4-{3-[(2-chloro-5-fluorobenzyl)oxy]phenyl}-8-(trifluoromethyl)cinnoline The title compound was made in the same manner as example 73 except using 2-chloro-5-fluorobenzyl bromide as the alkylating reagent. MS (ES) m/z 523.1.

Example 82

3-({3-[3-Benzyl-8-(trifluoromethyl)cinnolin-4-yl]phenoxy}methyl)benzoic acid

The title compound was made in the same manner as example 73 except using 3-bromomethyl-benzoic acid methyl ester as the alkylating reagent followed by NaOH hydrolysis. MS (ES) m/z 514.8.

Example 83

4-({3-[3-Benzyl-8-(trifluoromethyl)cinnolin-4-yl]phenoxy}methyl)benzoic acid

The title compound was made in the same manner as example 73 except using 4-bromomethyl-benzoic acid methyl ester as the alkylating reagent followed by NaOH hydrolysis. MS (ES) m/z 514.8.

Example 84

4-({3-[3-Benzyl-8-(trifluoromethyl)cinnolin-4-yl]phenoxy}methyl)-3-chlorobenzoic acid The title compound was made in the same manner as example 73 except using 4-bromomethyl-3-chlorobenzoic acid methyl ester as the alkylating reagent followed by NaOH hydrolysis. MS (ES) m/z 548.8.

Example 85

4-({3-[3-Benzyl-8-(trifluoromethyl)cinnolin-4-yl]phenoxy}methyl)-2-methoxybenzoic acid The title compound was made in the same manner as example 73 except using 4-bromomethyl-2-methoxybenzoic acid methyl ester as the alkylating reagent followed by NaOH hydrolysis. MS (ES) m/z 544.8.

Example 86

4-(3-{[5-Fluoro-2-(trifluoromethyl)benzyl]oxy}phenyl)-8-(trifluoromethyl)cinnoline The title compound was made in the same manner as example 73 except using 2-trifluoromethyl-5-fluorobenzyl bromide as the alkylating reagent and 3-(8-trifluoromethyl-cinnolin-4-yl)-phenol. MS (ES) m/z 467.1.

Example 87

4-(3-{[5-Chloro-2-(trifluoromethyl)benzyl]oxy}phenyl)-8-(trifluoromethyl)cinnoline The title compound was made in the same manner as example 73 except using 2-trifluoromethyl-5-chlorobenzyl bromide as the alkylating reagent and 3-(8trifluoromethyl-cinnolin-4-yl)-phenol. MS (ES) m/z 482.9.

Example 88

4-(3-{[2-(Trifluoromethoxy)benzyl]oxy}phenyl)-8-(trifluoromethyl)cinnoline

The title compound was made in the same manner as example 73 except using 2-trifluoromethoxybenzyl bromide as the alkylating reagent and 3-(8-trifluoromethyl-cinnolin-4-yl)-phenol. MS (ES) m/z 465.0.

Example 89

3-Benzyl-4-{3-[(1-methyl-1H-indol-2-yl)methoxy]phenyl}-8-(trifluoromethyl)cinnoline The title compound was made by the method shown in scheme 6. To a solution of 3-(3-benzyl-8-trifluoromethyl-cinnolin-4-yl)-phenol (190 mg, 0.5 mmol), (1-methyl-1H-indol-2-yl)-methanol (120 mg, 0.75 mmol), PPh$_3$ (262 mg, 1.0 mmol) in ether (10 ml) was added DIAD (202 mg, 11.0 mmol) dropwise. After 3 hr, the reaction was concentrated and purified by column chromatography (eluent 10% EtOAc/Hexane) to give a white foam (0.12 g). MS (ES) m/z 524.1.

Example 90

4-(3-{[2-(Trifluoromethoxy)benzyl]oxy}phenyl)-8-(trifluoromethyl)cinnoline

The title compound was made in the same manner as example 89 except using (5-fluoro-1-methyl-1H-indol-2-yl)-methanol. MS (ES) m/z 542.2.

Example 91

7-({3-[3-Benzyl-8-(trifluoromethyl)cinnolin-4-yl]phenoxy}methyl)-1-methyl-1H-indole-3-carboxylic acid The title compound was made in the same manner as example 89 except using 7-hydroxymethyl-1-methyl-1H-indole-3-carboxylic acid methyl ester followed by NaOH hydrolysis. MS (ES) m/z 568.2.

Example 92

[2,5-Dimethyl-4-({3-[8-(trifluoromethyl)cinnolin-4-yl]benzyl}amino)phenyl]acetic acid The title compound was made in by stirring 3-(8-trifluoromethyl-cinnolin-4-yl)-benzaldehyde (0.15 g, 0.5 mmol), (4-amino-2,5-dimethyl-phenyl)-acetic acid (0.15 g, 0.8 mmol) and NaHB(OAc)$_3$ (0.5 g) in DMF/AcOH at r.t. After 24 hr, the reaction was poured in water and extracted with EtOAc. The organic layer was dried (MgSO$_4$) and concentrated and the product was purified by HPLC to give a yellow solid (80 mg). MS (ESI) m/z 464.

Example 93

[5-({3-[8-(Trifluoromethyl)cinnolin-4-yl]benzyl}amino)-1-naphthyl]acetic acid

The title compound was made in the same manner as example 92 except using (5-amino-naphthalen-1-yl)-acetic acid as the amine. MS (ES) m/z 488.0.

Example 94

3-Benzyl-8-chloro-4-(3-{[2-(trifluoromethoxy)benzyl]oxy}phenyl)cinnoline

The title compound was made in the same manner as example 14 from 3-(3-benzyl-8-chloro-cinnolin-4-yl)-phenol and 2-bromomethyl-1-chloro-4-trifluoromethyl-benzene. MS (ES) m/z 521.0.

Example 95

3-Benzyl-8-chloro-4-(3-{[2-chloro-5-(trifluoromethyl)benzyl]oxy}phenyl)cinnoline The title compound was made in the same manner as example 14 from 3-(3-benzyl-8-chloro-cinnolin-4-yl)-phenol and 1-bromomethyl-2-trifluoromethoxy-benzene. MS (ES) m/z 539.0.

Example 96

3-[3-Benzyl-8-(trifluoromethyl)cinnolin-4-yl]benzaldehyde

The title compound was made in the same manner as example 13 from 3-benzyl-4-bromo-8-trifluoromethyl-cinnoline and 3-formyl-phenyl boronic acid. MS (ES) m/z 393.2.

Example 97

[4-({3-[3-Benzyl-8-(trifluoromethyl)cinnolin-4-yl]benzyl}amino)-2,3-dimethylphenyl]acetic acid The title compound was made in the same manner as example 92 by reductive amination between 3-[3-benzyl-8-(trifluoromethyl)cinnolin-4-yl]benzaldehyde and (4-amino-2,5-dimethyl-phenyl)-acetic acid. MS (ES) m/z 555.8.

Example 98

3-Benzyl-4-{3-[(1-methyl-1H-indol-7-yl)methoxy]phenyl}-8-(trifluoromethyl)cinnoline The title compound was made in the same manner as example 73 except using 7-bromomethyl-1-methyl-1H-indole as the alkylating reagent. MS (ES) m/z 524.1.

A number of embodiments of the invention have been described. Nevertheless, it will be understood that various modifications may be made without departing from the spirit and scope of the invention. Accordingly, other embodiments are in the claims.

---

What is claimed is:

1. A compound having formula (I):

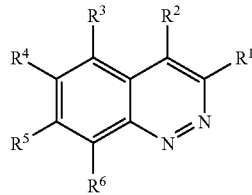

wherein:

$R^1$ is:

(i) $C_6$-$C_{10}$ aryl, optionally substituted with from 1-5 $R^b$; or
(ii) $C_7$-$C_{12}$ aralkyl optionally substituted with from 1-5 $R^c$;

$R^2$ is phenyl which is monosubsituted with a substituent selected from:

(i) hydroxyl;
(ii) $NH_2$;
(iii) halo;
(iv) $C_1$-$C_6$ alkoxy;
(v) $C_1$-$C_4$ haloalkyl;
(vi) —C(O)$R^i$;
(vii) $C_1$-$C_6$ alkyl, optionally substituted with 1 $NR^gR^h$;
(viii) —$NR^jC(O)NR^gR^h$;
(ix) $NR^gR^h$, wherein one of $R^g$ and $R^h$ is hydrogen, and the other is $C_7$-$C_{20}$ aralkyl or heteroaralkyl including 6-20 atoms, each of which is optionally substituted with from 1-10 $R^c$;
(x) $C_6$-$C_{18}$ aryl or heteroaryl including 5-16 atoms, each of which is optionally substituted with from 1-10 $R^b$;
(xi) $C_6$-$C_{18}$ aryloxy or heteroaryloxy including 5-16 atoms, each of which is optionally substituted with from 1-10 $R^{b'}$;
(xii) $C_7$-$C_{20}$ aralkoxy or heteroaralkoxy including 6-20 atoms, each of which is optionally substituted with from 1-10 $R^c$;
(xiii) $C_6$-$C_{18}$ thioaryloxy or thioheteroaryloxy including 5-16 atoms, each of which is optionally substituted with from 1-10 $R^{b'}$;
(xiv) $C_7$-$C_{20}$ thioaralkoxy or thioheteroaralkoxy including 6-20 atoms, each of which is optionally substituted with from 1-10 $R^c$;
(xv) $C_6$-$C_{18}$ aryl or heteroaryl including 5-16 atoms, each of which is optionally substituted with from 1-10 $R^{b'}$; and
(xvi) $C_7$-$C_{20}$ aralkyl or heteroaralkyl including 6-20 atoms, each of which is optionally substituted with from 1-10 $R^c$;

each of $R^3$, $R^4$, and $R^5$ is, independently:

(i) hydrogen, halo; $NR^gR^h$; nitro; azido, hydroxy; or
(ii) $C_1$-$C_{20}$ alkoxy or $C_1$-$C_{20}$ haloalkoxy, each of which is optionally substituted with from 1-10 $R^a$; or
(iii) $C_6$-$C_{18}$ aryloxy or heteroaryloxy including 5-16 atoms, each of which is optionally substituted with from 1-10 $R^b$; or
(iv) $C_7$-$C_{20}$ aralkoxy or heteroaralkoxy including 6-20 atoms, each of which is optionally substituted with from 1-10 $R^c$; $C_3$-$C_{20}$ cycloalkoxy or $C_3$-$C_{20}$ halocycloalkoxy, each of which is optionally substituted with from 1-10 $R^e$; or
(v) $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; mercapto; or
(vi) $C_1$-$C_{20}$ thioalkoxy or $C_1$-$C_{20}$ thiohaloalkoxy, each of which is optionally substituted with from 1-10 $R^a$; or
(vii) $C_6$-$C_{18}$ thioaryloxy or thioheteroaryloxy including 5-16 atoms, each of which is optionally substituted with from 1-10 $R^b$; or
(viii) $C_7$-$C_{20}$ thioaralkoxy or thioheteroaralkoxy including 6-20 atoms, each of which is optionally substituted with from 1-10 $R^c$; or
(ix) $C_3$-$C_{20}$ thiocycloalkoxy or $C_3$-$C_{20}$ thiohalocycloalkoxy, each of which is optionally substituted with from 1-10 $R^e$; or
(x) $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; or
(xi) cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)(O$R^g$)(O$R^h$); or
(xii) $C_1$-$C_{20}$ alkyl or $C_1$-$C_{20}$ haloalkyl, each of which is optionally substituted with from 1-10$R^a$; or
(xiii) $C_3$-$C_{20}$ cycloalkyl or $C_3$-$C_{20}$ halocycloalkyl, optionally substituted with from 1-10 $R^e$; or
(xiv) $C_3$-$C_{20}$ cycloalkenyl, heterocyclyl including 3-20 atoms, or heterocycloalkenyl including 3-20 atoms, each of which is optionally substituted with from 1-10 $R^f$; or
(xv) $C_2$-$C_{20}$ alkenyl or $C_2$-$C_{20}$ alkynyl, each of which is optionally substituted with from 1-10 $R^d$; or
(xvi) $C_7$-$C_{20}$ aralkyl or heteroaralkyl including 6-20 atoms, each of which is optionally substituted with from 1-10 $R^c$; or
(xvii) $C_6$-$C_{18}$ aryl or heteroaryl including 5-16 atoms, each of which is optionally substituted with from 1-10 $R^b$;

$R^6$ is:
(i) halo; or
(ii) $C_1$-$C_{10}$ haloalkyl;

$R^a$ at each occurrence is, independently:
(i) $NR^gR^h$; nitro; azido; hydroxy; oxo; thioxo; =$NR^m$; or
(ii) $C_1$-$C_{20}$ alkoxy; $C_1$-$C_{20}$ haloalkoxy; $C_6$-$C_{18}$ aryloxy or heteroaryloxy including 5-16 atoms, each of which is optionally substituted with from 1-10 $R^b$; or
(iii) $C_7$-$C_{20}$ aralkoxy or heteroaralkoxy including 6-20 atoms, each of which is optionally substituted with from 1-10 $R^c$; or
(iv) $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; or
(v) mercapto; $C_1$-$C_{20}$ thioalkoxy; $C_1$-$C_{20}$ thiohaloalkoxy; $C_6$-$C_{18}$ thioaryloxy or thioheteroaryloxy including 5-16 atoms, each of which is optionally substituted with from 1-10 $R^b$; or
(vi) $C_7$-$C_{20}$ thioaralkoxy or thioheteroaralkoxy including 6-20 atoms, each of which is optionally substituted with from 1-10 $R^c$; or
(vii) $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; or
(viii) cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$);

$R^b$ at each occurrence is, independently:
(i) halo; $NR^gR^h$; nitro; azido; hydroxy; or
(ii) $C_1$-$C_{20}$ alkoxy or $C_1$-$C_{20}$ haloalkoxy, each of which is optionally substituted with from 1-10 $R^a$; or
(iii) $C_6$-$C_{18}$ aryloxy or heteroaryloxy including 5-16 atoms, each of which is optionally substituted with from 1-10 $R^b$ or $R^{b'}$; or
(iv) $C_7$-$C_{20}$ aralkoxy or heteroaralkoxy including 6-20 atoms, each of which is optionally substituted with from 1-10 $R^c$; or
(v) $C_3$-$C_{16}$ cycloalkoxy or $C_3$-$C_{16}$ halocycloalkoxy, each of which is optionally substituted with from 1-10 $R^e$; or
(vi) $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; or
(vii) mercapto; $C_1$-$C_{20}$ thioalkoxy or $C_1$-$C_{20}$ thiohaloalkoxy, each of which is optionally substituted with from 1-10 $R^a$; or
(viii) $C_6$-$C_{18}$ thioaryloxy or thioheteroaryloxy including 5-16 atoms, each of which is optionally substituted with from 1-10 $R^b$; or
(ix) $C_7$-$C_{20}$ thioaralkoxy or thioheteroaralkoxy including 6-20 atoms, each of which is optionally substituted with from 1-10 $R^c$; or
(x) $C_3$-$C_{16}$ thiocycloalkoxy or $C_3$-$C_{16}$ thiohalocycloalkoxy, each of which is optionally substituted with from 1-10 $R^e$; or
(xi) $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; or
(xii) cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$); or
(xiii) $C_1$-$C_{20}$ alkyl or $C_1$-$C_{20}$ haloalkyl, each of which is optionally substituted with from 1-10 $R^a$; or
(xiv) $C_3$-$C_{20}$ cycloalkyl or $C_3$-$C_{20}$ halocycloalkyl, optionally substituted with from 1-10 $R^e$; or
(xv) $C_3$-$C_{20}$ cycloalkenyl, heterocyclyl including 3-20 atoms, or heterocycloalkenyl including 3-20 atoms, each of which is optionally substituted with from 1-10 $R^f$; or
(xvi) $C_2$-$C_{20}$ alkenyl or $C_2$-$C_{20}$ alkynyl, each of which is optionally substituted with from 1-10 $R^d$; or
(xvii) $C_7$-$C_{20}$ aralkyl or heteroaralkyl including 6-20 atoms, each of which is optionally substituted with from 1-10 $R^c$; or
(xviii) $C_6$-$C_{18}$ aryl or heteroaryl including 5-16 atoms, each of which is optionally substituted with from 1-10 $R^{b'}$;

$R^{b'}$ at each occurrence is, independently:
(i) halo; $NR^gR^h$; nitro; azido; hydroxy; or
(ii) $C_1$-$C_{20}$ alkyl, $C_1$-$C_{20}$ haloalkyl, $C_2$-$C_{20}$ alkenyl; $C_2$-$C_{20}$ alkynyl; $C_3$-$C_{20}$ cycloalkyl; $C_3$-$C_{20}$ halocycloalkyl; $C_3$-$C_{20}$ cycloalkenyl, heterocyclyl including 3-20 atoms; heterocycloalkenyl including 3-20 atoms; $C_7$-$C_{20}$ aralkyl; heteroaralkyl including 6-20 atoms; or
(iii) $C_1$-$C_{20}$ alkoxy; $C_1$-$C_{20}$ haloalkoxy; $C_6$-$C_{18}$ aryloxy or heteroaryloxy including 5-16 atoms; $C_7$-$C_{20}$ aralkoxy or heteroaralkoxy including 6-20 atoms; $C_3$-$C_{16}$ cycloalkoxy or $C_3$-$C_{16}$ halocycloalkoxy; $C_3$-$C_{20}$ cycloalkenyloxy, heterocyclyloxy including 3-20 atoms, or heterocycloalkenyloxy including 3-20 atoms; or
(iv) mercapto; $C_1$-$C_{20}$ thioalkoxy or $C_1$-$C_{20}$ thiohaloalkoxy; $C_6$-$C_{18}$ thioaryloxy or thioheteroaryloxy including 5-16 atoms; $C_7$-$C_{20}$ thioaralkoxy or thioheteroaralkoxy including 6-20 atoms; $C_3$-$C_{16}$ thiocycloalkoxy or $C_3$-$C_{16}$ thiohalocycloalkoxy; $C_3$-$C_{20}$ thiocycloalkenyloxy, thioheterocyclyloxy including 3-20 atoms, or thioheterocycloalkenyloxy including 3-20 atoms; or
(v) cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$);

$R^c$ at each occurrence is, independently:
(i) halo; $NR^gR^h$; nitro; azido; hydroxy; oxo; thioxo; =$NR^m$; or
(ii) $C_1$-$C_{20}$ alkoxy or $C_1$-$C_{20}$ haloalkoxy, each of which is optionally substituted with from 1-10 $R^a$; $C_6$-$C_{18}$ aryloxy or heteroaryloxy including 5-16 atoms, each of which is optionally substituted with from 1-10 $R^b$; or
(iii) $C_7$-$C_{20}$ aralkoxy or heteroaralkoxy including 6-20 atoms, each of which is optionally substituted with from 1-10 $R^c$ or $R^{c'}$; or
(iv) $C_3$-$C_{16}$ cycloalkoxy or $C_3$-$C_{16}$ halocycloalkoxy, each of which is optionally substituted with from 1-10 $R^e$; or
(v) $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; or
(vi) mercapto; $C_1$-$C_{20}$ thioalkoxy or $C_1$-$C_{20}$ thiohaloalkoxy, each of which is optionally substituted with from 1-10 $R^a$; or (vii) $C_6$-$C_{18}$ thioaryloxy or thioheteroaryloxy including 5-16 atoms, each of which is optionally substituted with from 1-10 $R^b$; or (viii) $C_7$-$C_{20}$ thioaralkoxy or thioheteroaralkoxy including 6-20 atoms, each of which is optionally substituted with from 1-10 $R^c$; or (ix) $C_3$-$C_{16}$ thiocycloalkoxy or $C_3$-$C_{16}$ thiohalocycloalkoxy, each of which is optionally substituted with from 1-10 $R^e$; or (x) $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; or (xi) cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$); or (xii) $C_1$-$C_{20}$ alkyl or $C_1$-$C_{20}$ haloalkyl, each of which is optionally substituted with from 1-10 $R^a$; or (xiii) $C_3$-$C_{20}$ cycloalkyl or $C_3$-$C_{20}$ halocycloalkyl, optionally substituted with from 1-10 $R^e$; or (xiv) $C_3$-$C_{20}$ cycloalkenyl, heterocyclyl including 3-20 atoms, or heterocycloalkenyl including 3-20 atoms, each of which is optionally substituted with from 1-10 $R^f$; or (xv) $C_2$-$C_{20}$ alkenyl or $C_2$-$C_{20}$ alkynyl, each of which is optionally substituted with from 1-10 $R^d$; or (xvi) $C_7$-$C_{20}$ aralkyl or heteroaralkyl including 6-20 atoms, each of which is optionally substituted with from 1-10 $R^c$ or $R^{c'}$; or (xvii) $C_6$-$C_{18}$ aryl or heteroaryl including 5-16 atoms, each of which is optionally substituted with from 1-10 $R^b$;

$R^d$ at each occurrence is, independently, halo, $NR^gR^h$; nitro; azido; hydroxy; oxo; thioxo; =$NR^m$; $C_1$-$C_{20}$ alkoxy; $C_1$-$C_{20}$ haloalkoxy; $C_6$-$C_{18}$ aryloxy; heteroaryloxy including 5-16 atoms; $C_7$-$C_{20}$ aralkoxy; heteroaralkoxy including 6-20 atoms; $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy; thioheteroaryloxy including 5-16 atoms; $C_7$-$C_{20}$ thioaralkoxy; thioheteroaralkoxy including 6-20 atoms; $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$);

$R^{c'}$ is oxo; thioxo; =$NR^m$; or $R^{b'}$;

$R^e$ at each occurrence is, independently:

(i) $NR^gR^h$; nitro; azido; hydroxy; oxo; thioxo; =$NR^m$; $C_1$-$C_{20}$ alkoxy; $C_1$-$C_{20}$ haloalkoxy; $C_6$-$C_{18}$ aryloxy; heteroaryloxy including 5-16 atoms; $C_7$-$C_{20}$ aralkoxy; heteroaralkoxy including 6-20 atoms; $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy; thioheteroaryloxy including 5-16 atoms; $C_7$-$C_{20}$ thioaralkoxy; thioheteroaralkoxy including 6-20 atoms; $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$); or (ii) $C_2$-$C_{20}$ alkenyl or $C_2$-$C_{20}$ alkynyl, each of which is optionally substituted with from 1-10 $R^d$; or (iii) $C_6$-$C_{18}$ aryl or heteroaryl including 5-16 atoms, each of which is optionally substituted with from 1-10 $R^b$;

$R^f$ at each occurrence is, independently:

(i) halo, $NR^gR^h$; nitro; azido; hydroxy; oxo; thioxo; =$NR^m$; $C_1$-$C_{20}$ alkoxy; $C_1$-$C_{20}$ haloalkoxy; $C_6$-$C_{18}$ aryloxy; heteroaryloxy including 5-16 atoms; $C_7$-$C_{20}$ aralkoxy; heteroaralkoxy including 6-20 atoms; $C_3$-$C_{16}$ cycloalkoxy; $C_3$-$C_{16}$ halocycloalkoxy; $C_3$-$C_{20}$ cycloalkenyloxy; heterocyclyloxy including 3-20 atoms; heterocycloalkenyloxy including 3-20 atoms; mercapto; $C_1$-$C_{20}$ thioalkoxy; $C_1$-$C_{20}$ thiohaloalkoxy; $C_6$-$C_{18}$ thioaryloxy; thioheteroaryloxy including 5-16 atoms; $C_7$-$C_{20}$ thioaralkoxy; thioheteroaralkoxy including 6-20 atoms; $C_3$-$C_{16}$ thiocycloalkoxy; $C_3$-$C_{16}$ thiohalocycloalkoxy; $C_3$-$C_{20}$ thiocycloalkenyloxy; thioheterocyclyloxy including 3-20 atoms; thioheterocycloalkenyloxy including 3-20 atoms; cyano; formyl; $C_1$-$C_3$ alkylenedioxy; —C(O)$NR^gR^h$; —OC(O)$NR^gR^h$; —C(O)$R^i$, —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$); or (ii) $C_2$-$C_{20}$ alkenyl or $C_2$-$C_{20}$ alkynyl, each of which is optionally substituted with from 1-10 $R^a$; or (iii) $C_6$-$C_{18}$ aryl or heteroaryl including 5-16 atoms, each of which is optionally substituted with from 1-10 $R^b$;

each of $R^g$, $R^h$, $R^i$, and $R^j$, at each occurrence is, independently:

(i) hydrogen; or (ii) $C_1$-$C_{20}$ alkyl or $C_1$-$C_{20}$ haloalkyl, each of which is optionally substituted with from 1-10 $R^a$;

(iii) $C_2$-$C_{20}$ alkenyl or $C_2$-$C_{20}$ alkynyl, each of which is optionally substituted with from 1-10 $R^d$; or (iv) $C_3$-$C_{20}$ cycloalkyl or $C_3$-$C_{20}$ halocycloalkyl, each of which is optionally substituted with from 1-10 $R^e$; or (v) $C_3$-$C_{20}$ cycloalkenyl, heterocyclyl including 3-16 atoms, or heterocycloalkenyl including 3-16 atoms, each of which is optionally substituted with from 1-10 $R^f$; or (vi) $C_7$-$C_{20}$ aralkyl or heteroaralkyl including 6-20 atoms, each of which is optionally substituted with from 1-10 $R^c$; or (vii) $C_6$-$C_{18}$ aryl or heteroaryl including 5-16 atoms, each of which is optionally substituted with from 1-10 $R^b$;

$R^k$ is $R^i$, $OR^i$, or $NR^gR^h$;

$R^m$ is:

(i) hydrogen; or (ii) $C_1$-$C_{12}$ alkyl or $C_1$-$C_{12}$ haloalkyl, each of which is optionally substituted with from 1-5 $R^a$; or (iii) $C_2$-$C_{20}$ alkenyl; $C_2$-$C_{20}$ alkynyl; or (iv) $C_7$-$C_{20}$ aralkyl; heteroaralkyl including 6-20 atoms; or (v) $C_3$-$C_{20}$ cycloalkyl; $C_3$-$C_{20}$ cycloalkenyl; or (vi) heterocyclyl including 3-20 atoms; heterocycloalkenyl including 3-20 atoms; or (vii) $C_6$-$C_{18}$ aryl; heteroaryl including 5-16 atoms; $NR^gR^h$, or $OR^i$; and n is 0, 1 or 2; or a salt thereof.

2. The compound of claim 1, wherein $R^1$ is $C_6$-$C_{10}$ aryl, optionally substituted with from 1-5 $R^b$.

3. The compound of claim 1, wherein $R^1$ is phenyl, optionally substituted with from 1-5 $R^b$.

4. The compound of claim 1, wherein $R^1$ is phenyl.

5. The compound of claim 1, wherein $R^1$ is $C_7$-$C_{12}$ aralkyl optionally substituted with from 1-5 $R^c$.

6. The compound of claim 1, wherein $R^1$ is benzyl.

7. The compound of claim 1, wherein $R^b$ at each occurrence is, independently:
  (i) halo; $NO_2$; $NR^gR^h$; hydroxy; $C_1$-$C_{20}$ alkoxy or $C_1$-$C_{20}$ haloalkoxy, each of which is optionally substituted with from 1-10 $R^a$; $C_6$-$C_{18}$ aryloxy or heteroaryloxy including 5-16 atoms, each of which is optionally substituted with from 1-10 $R^{b'}$; $C_7$-$C_{20}$ aralkoxy or heteroaralkoxy including 6-20 atoms, each of which is optionally substituted with from 1-10 $R^c$; $C_3$-$C_{16}$ cycloalkoxy or $C_3$-$C_{16}$ halocycloalkoxy, each of which is optionally substituted with from 1-10 $R^e$; $C_3$-$C_{20}$ cycloalkenyloxy, heterocyclyloxy including 3-20 atoms, or heterocycloalkenyloxy including 3-20 atoms, each of which is optionally substituted with from 1-10 $R^f$; mercapto; $C_1$-$C_{20}$ thioalkoxy or $C_1$-$C_{20}$ thiohaloalkoxy, each of which is optionally substituted with from 1-10 $R^a$; $C_6$-$C_{18}$ thioaryloxy or thioheteroaryloxy including 5-16 atoms, each of which is optionally substituted with from 1-10 $R^{b'}$; $C_7$-$C_{20}$ thioaralkoxy or thioheteroaralkoxy including 6-20 atoms, each of which is optionally substituted with from 1-10 $R^c$; $C_3$-$C_{20}$ thiocycloalkoxy or $C_3$-$C_{20}$ thiohalocycloalkoxy, each of which is optionally substituted with from 1-10 $R^e$; $C_3$-$C_{20}$ thiocycloalkenyloxy, thioheterocyclyloxy including 3-20 atoms, or thioheterocycloalkenyloxy including 3-20 atoms, each of which is optionally substituted with from 1-10 $R^f$; cyano; —C(O)$NR^gR^h$; —OC(O)$NR^gR^h$; —C(O)$R^i$; —C(O)$OR^i$; —OC(O)$R^i$; —C(O)$SR^i$; —SC(O)$R^i$; —C(S)$SR^i$; —SC(S)$R^i$; —$NR^jC(O)R^i$; —$NR^jC(O)OR^i$; —$NR^jC(O)NR^gR^h$; —S(O)$_nR^k$; —$NR^jS(O)_nR^i$; —C($NR^m$)$R^i$; or —P(O)($OR^g$)($OR^h$);
  (ii) $C_1$-$C_{20}$ alkyl or $C_1$-$C_{20}$ haloalkyl, each of which is optionally substituted with from 1-10 $R^a$; or
  (iii) $C_7$-$C_{20}$ aralkyl or heteroaralkyl including 6-20 atoms, each of which is optionally substituted with from 1-10 $R^c$; or
  (iv) $C_6$-$C_{18}$ aryl or heteroaryl including 5-16 atoms, each of which is optionally substituted with from 1-10 $R^{b'}$.

8. The compound of claim 1, wherein $R^2$ is:

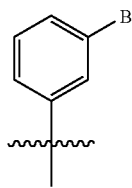

wherein B is selected from:
(i) hydroxyl;
(ii) $NH_2$;
(iii) halo;
(iv) $C_1$-$C_6$ alkoxy;
(v) $C_1$-$C_4$ haloalkyl;
(vi) —C(O)$R^i$;
(vii) $C_1$-$C_6$ alkyl, optionally substituted with 1 $NR^gR^h$;
(viii) —$NR^jC(O)NR^gR^h$;

(ix) $NR^gR^h$, wherein one of $R^g$ and $R^h$ is hydrogen, and the other is $C_7$-$C_{20}$ aralkyl or heteroaralkyl including 6-20 atoms, each of which is optionally substituted with from 1-10 $R^c$;

(x) $C_6$-$C_{18}$ aryl or heteroaryl including 5-16 atoms, each of which is optionally substituted with from 1-10 $R^b$;

(xi) $C_6$-$C_{18}$ aryloxy or heteroaryloxy including 5-16 atoms, each of which is optionally substituted with from 1-10 $R^{b'}$;

(xii) $C_7$-$C_{20}$ aralkoxy or heteroaralkoxy including 6-20 atoms, each of which is optionally substituted with from 1-10 $R^c$;

(xiii) $C_6$-$C_{18}$ thioaryloxy or thioheteroaryloxy including 5-16 atoms, each of which is optionally substituted with from 1-10 $R^{b'}$;

(xiv) $C_7$-$C_{20}$ thioaralkoxy or thioheteroaralkoxy including 6-20 atoms, each of which is optionally substituted with from 1-10 $R^c$;

(xv) $C_6$-$C_{18}$ aryl or heteroaryl including 5-16 atoms, each of which is optionally substituted with from 1-10 $R^{b'}$; and (xvi) $C_7$-$C_{20}$ aralkyl or heteroaralkyl including 6-20 atoms, each of which is optionally substituted with from 1-10 $R^c$.

9. The compound of claim 8, wherein B is hydroxy.

10. The compound of claim 8, wherein B is $NH_2$.

11. The compound of claim 8, wherein B is halo.

12. The compound of claim 8, wherein B is $C_1$-$C_6$ alkoxy.

13. The compound of claim 8, wherein B is $C_1$-$C_4$ haloalkyl.

14. The compound of claim 8, wherein B is —C(O)$R^i$.

15. The compound of claim 8, wherein B is $C_1$-$C_6$ alkyl, optionally substituted with 1 $NR^gR^h$.

16. The compound of claim 8, wherein B is —$NR^jC(O)NR^gR^h$.

17. The compound of claim 8, wherein B is:
  (i-B) $NR^gR^h$, wherein one of $R^g$ and $R^h$ is hydrogen, and the other is $C_7$-$C_{20}$ aralkyl or heteroaralkyl including 6-20 atoms, each of which is optionally substituted with from 1-10 $R^c$; or
  (ii-B) $C_6$-$C_{18}$ aryl or heteroaryl including 5-16 atoms, each of which is optionally substituted with from 1-10 $R^b$; or
  (iii-B) $C_6$-$C_{18}$ aryloxy or heteroaryloxy including 5-16 atoms, each of which is optionally substituted with from 1-10 $R^{b'}$; or
  (iv-B) $C_7$-$C_{20}$ aralkoxy or heteroaralkoxy including 6-20 atoms, each of which is optionally substituted with from 1-10 $R^c$; or
  (v-B) $C_6$-$C_{18}$ thioaryloxy or thioheteroaryloxy including 5-16 atoms, each of which is optionally substituted with from 1-10 $R^{b'}$; or
  (vi-B) $C_7$-$C_{20}$ thioaralkoxy or thioheteroaralkoxy including 6-20 atoms, each of which is optionally substituted with from 1-10 $R^c$; or
  (vii-B) $C_6$-$C_{18}$ aryl or heteroaryl including 5-16 atoms, each of which is optionally substituted with from 1-10 $R^{b'}$; or
  (viii-B) $C_7$-$C_{20}$ aralkyl or heteroaralkyl including 6-20 atoms, each of which is optionally substituted with from 1-10 $R^c$.

18. The compound of claim 17, wherein B is:
  (i-B') $NR^gR^h$, wherein one of $R^g$ and $R^h$ is hydrogen, and the other is $C_7$-$C_{20}$ aralkyl or heteroaralkyl including 6-20 atoms, each of which is optionally substituted with from 1-10 $R^c$;

(ii-B') $C_7$-$C_{20}$ aralkoxy or heteroaralkoxy including 6-20 atoms, each of which is optionally substituted with from 1-10 $R^c$; or (iii-B') $C_7$-$C_{20}$ thioaralkoxy or thioheteroaralkoxy including 6-20 atoms, each of which is optionally substituted with from 1-10 $R^c$; or (iv-B') $C_7$-$C_{20}$ aralkyl or heteroaralkyl including 6-20 atoms, each of which is optionally substituted with from 1-10 $R^c$.

19. The compound of claim 18, wherein $R^b$, $R^{b'}$ and $R^c$ at each occurrence are each, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$.

20. The compound of claim 19, wherein $R^a$ is —C(O)OH or —C(O)$OCH_3$.

21. The compound of claim 8, wherein B is:

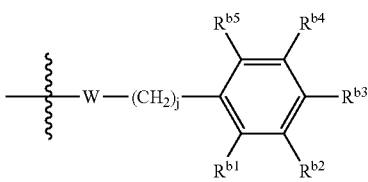

wherein:
W is $NR^j$, O, S, or is absent;
j is 0, 1, 2, 3, 4, or 5; and
each of $R^{b1}$, $R^{b2}$, $R^{b3}$, $R^{b4}$, and $R^{b5}$ is, independently, hydrogen, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$.

22. The compound of claim 21, wherein W is $NR^j$, O, or S.

23. The compound of claim 21, wherein $R^j$ is hydrogen.

24. The compound of claim 21, wherein j is 1.

25. The compound of claim 21, wherein one of $R^{b1}$, $R^{b2}$, $R^{b3}$, $R^{b4}$, or $R^{b5}$ is, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and the other four are hydrogen.

26. The compound of claim 25, wherein $R^{b3}$ is $C_1$-$C_4$ alkyl substituted with 1 $R^a$.

27. The compound of claim 26, wherein $R^{b3}$ is —$CH_2$C(O)OH, —$CH_2$C(O)$OCH_3$, —C($CH_3$)$_2$C(O)OH, or —C($CH_3$)$_2$C(O)$OCH_3$.

28. The compound of claim 25, wherein $R^{b1}$ is $C_1$-$C_6$ haloalkoxy.

29. The compound of claim 21, wherein two of $R^{b1}$, $R^{b2}$, $R^{b3}$, $R^{b4}$, or $R^{b5}$ are each, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and the other three are hydrogen.

30. The compound of claim 29, wherein $R^{b1}$ and $R^{b4}$ are each, independently, halo; $NO_2$; hydroxy; $C_1$-$C_{10}$ alkoxy; $C_1$-$C_{10}$ haloalkoxy; cyano; —C(O)$R^i$; $C_1$-$C_{10}$ alkyl or $C_1$-$C_{10}$ haloalkyl, each of which is optionally substituted with from 1-5 $R^a$; or —C(O)$OR^i$; and each of $R^{b2}$, $R^{b3}$, and $R^{b5}$ is hydrogen.

31. The compound of claim 30, wherein $R^{b1}$ and $R^{b4}$ are each, independently, halo; $C_1$-$C_6$ alkyl; $C_1$-$C_4$ haloalkyl; or $C_1$-$C_6$ alkoxy.

32. The compound of claim 29, wherein $R^{b1}$ and $R^{b2}$ are each, independently, halo; $C_1$-$C_6$ alkyl; or $C_1$-$C_4$ haloalkyl, and each of $R^{b3}$, $R^{b4}$, and $R^{b5}$ is hydrogen.

33. The compound of claim 29, wherein $R^{b2}$ and $R^{b3}$ are, independently, halo; $C_1$-$C_6$ alkoxy; or —C(O)$OR^i$; and each of $R^{b1}$, $R^{b4}$, and $R^{b5}$ is hydrogen.

34. The compound of claim 1, wherein each of $R^3$, $R^4$ and $R^5$ is, independently, hydrogen or halo.

35. The compound of claim 1, wherein each of $R^3$, $R^4$ and $R^5$ is hydrogen.

36. The compound of claim 1, wherein $R^6$ is $C_1$-$C_{10}$ haloalkyl.

37. The compound of claim 1, wherein $R^6$ is $CF_3$.

38. The compound of claim 1, wherein $R^6$ is halo.

39. The compound of claim 1, wherein $R^6$ is chloro.

40. A pharmaceutical composition comprising a compound of formula (I), or a pharmaceutically acceptable salt thereof, as claimed in claim 1, and a pharmaceutically acceptable carrier.

41. The compound of claim 8, wherein B is $NR^gR^h$, wherein one of $R^g$ and $R^h$ is hydrogen, and the other is $C_7$-$C_{20}$ aralkyl or heteroaralkyl including 6-20 atoms, each of which is optionally substituted with from 1-10 $R^c$.

42. The compound of claim 8, wherein B is $NR^gR^h$, wherein one of $R^g$ and $R^h$ is hydrogen, and the other is heteroaralkyl including 6-20 atoms, which is optionally substituted with from 1-10 $R^c$.

43. The compound of claim 8, wherein B is $NR^gR^h$, wherein one of $R^g$ and $R^h$ is hydrogen, and the other is —$(CH_2)_{1-5}$-(heteroaryl), wherein the heteroaryl includes from 5-10 atoms and is optionally substituted with from 1-5 $R^c$.

44. The compound of claim 8, wherein B is —NH—$CH_2$-indolyl, wherein the —$CH_2$— group is attached to the 2 or 7 position of the indole ring, and wherein the indole ring is optionally substituted with from 1-5 $R^c$.

45. The compound of claim 1, wherein the compound is selected from the group consisting of:
3-benzyl-4-phenyl-8-(trifluoromethyl)cinnoline;
8-methyl-3,4-diphenylcinnoline;
3,4-diphenyl-8-(trifluoromethyl)cinnoline;
8-bromo-3,4-diphenylcinnoline;
8-chloro-3,4-diphenylcinnoline;
[4-({[3-(8-methyl-3-phenylcinnolin-4-yl)phenyl]amino}methyl)phenyl]acetic acid;
3-(8-chloro-3-phenyl-cinnolin-4-yl)-phenylamine;
(4-{[3-(8-chloro-3-phenyl-cinnolin-4-yl)-phenylamino]-methyl}-phenyl)-acetic acid methyl ester
[4-({[3-(8-chloro-3-phenylcinnolin-4-yl)phenyl]amino}methyl)phenyl]acetic acid;
N-[3-(8-chloro-3-phenylcinnolin-4-yl)phenyl]-N-phenylurea;
3-(8-chloro-3-phenylcinnolin-4-yl)phenol;
(4-{[3-(8-chloro-3-phenylcinnolin-4-yl)phenoxy]methyl}phenyl)acetic acid;
3-(8-chloro-3-methylcinnolin-4-yl)phenol;
methyl (4-{[3-(8-chloro-3-methylcinnolin-4-yl)phenoxy]methyl}phenyl)acetate;
(4-{[3-(8-chloro-3-methylcinnolin-4-yl)phenoxy]methyl}phenyl)acetic acid;
[4-({[3-(8-chloro-3-methylcinnolin-4-yl)phenyl]thio}methyl)phenyl]acetic acid;
2-(4-{[3-(8-chloro-3-methylcinnolin-4-yl)phenoxy]methyl}phenyl)-2-methylpropanoic acid;
8-chloro-4-{3-[(2,5-dimethylbenzyl)oxy]phenyl}-3-methylcinnoline;

[3-(8-chloro-3-phenylcinnolin-4-yl)phenyl](2,3-dimethylbenzyl)amine;
[3-(8-chloro-3-phenylcinnolin-4-yl)phenyl](2,5-dimethylbenzyl)amine;
[3-(8-chloro-3-phenylcinnolin-4-yl)phenyl](1-naphthylmethyl)amine;
[3-(8-chloro-3-phenylcinnolin-4-yl)phenyl](3,4-dichlorobenzyl)amine;
[3-(8-chloro-3-phenylcinnolin-4-yl)phenyl][5-fluoro-2-trifluoromethyl)benzyl]amine;
[3-(8-chloro-3-phenylcinnolin-4-yl)phenyl][2-chloro-3-(trifluoromethyl)benzyl]amine;
methyl 2-[4-({[3-(8-chloro-3-phenylcinnolin-4-yl)phenyl]amino}methyl)phenyl]-2-methylpropanoate;
2[4-({[3-(8-chloro-3-phenylcinnolin-4-yl)phenyl]amino}methyl)phenyl]-2-methylpropanoic acid;
4-{3-[(2-bromo-5-methoxybenzyl)oxy]phenyl}-8-chloro-3-phenylcinnoline;
8-chloro-4-(3-{[5-chloro-2-(trifluoromethyl)benzyl]oxy}phenyl)-3-phenylcinnoline
8-chloro-4-{3-[(3,4-dichlorobenzyl)oxy]phenyl}-3-phenylcinnoline;
[3-(3-benzyl-8-chlorocinnolin-4-yl)phenyl][5-fluoro-2-trifluoromethyl)benzyl]amine;
[3-(8-chloro-3-phenylcinnolin-4-yl)phenyl][(1-methyl-1H-indol-2-yl)methyl]amine;
[3-(3-benzyl-8-chlorocinnolin-4-yl)phenyl]amine;
[3-(3-benzyl-8-chlorocinnolin-4-yl)phenyl][2-chloro-3-(trifluoromethyl)benzyl]amine;
[3-(3-benzyl-8-chlorocinnolin-4-yl)phenyl](2,3-dimethylbenzyl)amine;
[3-(3-benzyl-8-chlorocinnolin-4-yl)phenyl][5-chloro-2-(trifluoromethyl)benzyl]amine;
[3-(8-chloro-3-phenylcinnolin-4-yl)phenyl](2-naphthylmethyl)amine;
[3-(8-chloro-3-phenylcinnolin-4-yl)phenyl][5-chloro-2-(trifluoromethyl)benzyl]amine;
[3-(8-chloro-3-phenylcinnolin-4-yl)phenyl][2-fluoro-5-(trifluoromethyl)benzyl]amine;
N-(5-bromo-2-fluorobenzyl)-3-(8-chloro-3-phenylcinnolin-4-yl)aniline;
N-(5-bromo-2-methoxybenzyl)-3-(8-chloro-3-phenylcinnolin-4-yl)aniline
[3-(8-chloro-3-phenylcinnolin-4-yl)phenyl][2-fluoro-3-(trifluoromethyl)benzyl]amine;
N-[2,5-bis(trifluoromethyl)benzyl]-3-(8-chloro-3-phenylcinnolin-4-yl)aniline;
[3-(3-benzyl-8-chlorocinnolin-4-yl)phenyl](1-naphthylmethyl)amine;
N-(2-bromo-5-methoxybenzyl)-3-(8-chloro-3-phenylcinnolin-4-yl)aniline;
[3-(3-benzyl-8-chlorocinnolin-4-yl)phenyl][(1-methyl-1H-indol-2-yl)methyl]amine;
[3-(8-chloro-3-phenylcinnolin-4-yl)phenyl][(1-methyl-1H-indol-7-yl)methyl]amine;
[3-(3-benzyl-8-chlorocinnolin-4-yl)phenyl](3,4-dichlorobenzyl)amine;
[3-(8-chloro-3-phenylcinnolin-4-yl)phenyl][(3-methyl-1-benzothien-2-yl)methyl]amine;
8-chloro-4-(3-{[3-(morpholin-4-ylcarbonyl)benzyl]oxy}phenyl)-3-phenylcinnoline;
N-(1-benzothien-2-ylmethyl)-3-(8-chloro-3-phenylcinnolin-4-yl)aniline;
N-(1-benzothien-3-ylmethyl)-3-(8-chloro-3-phenylcinnolin-4-yl)aniline;
[3-(8-chloro-3-phenylcinnolin-4-yl)phenyl]{[4-(trifluoromethyl)-1-benzothien-2-yl]methyl}amine;
3-(3-benzyl-8-chlorocinnolin-4-yl)phenol;
3-benzyl-4-[3-(benzyloxy)phenyl]-8-chlorocinnoline;
3-benzyl-8-chloro-4-(3-{[5-chloro-2-(trifluoromethyl)benzyl]oxy}phenyl)cinnoline;
3-benzyl-8-chloro-4-{3-[(1-methyl-1H-indol-7-yl)methoxy]phenyl}cinnoline;
3-benzyl-8-chloro-4-(3-{[2-chloro-3-(trifluoromethyl)benzyl]oxy}phenyl)cinnoline;
3-benzyl-8-chloro-4-(3-{[2-fluoro-3-(trifluoromethyl)benzyl]oxy}phenyl) cinnoline;
3-benzyl-8-chloro-4-{3-[(2-chlorobenzyl)oxy]phenyl}cinnoline;
3-benzyl-8-chloro-4-(3-{[3-(trifluoromethyl)benzyl]oxy}phenyl)cinnoline;
3-benzyl-8-chloro-4-(3-{[5-fluoro-2-(trifluoromethyl)benzyl]oxy}phenyl)cinnoline;
N-[3-(3-benzyl-8-chlorocinnolin-4-yl)phenyl]-N-[(1-methyl-1H-indol-7-yl)methyl]amine;
3-(3-benzyl-8-trifluoromethyl-cinnolin-4-yl)-phenol;
3-benzyl-4-(3-fluoro-phenyl)-8-trifluoromethyl-cinnoline;
3-benzyl-4-(4-fluoro-phenyl)-8-trifluoromethyl-cinnoline;
3-benzyl-4-(2-fluoro-phenyl)-8-trifluoromethyl-cinnoline;
3-benzyl-8-trifluoromethyl-4-(4-trifluoromethyl-phenyl)-cinnoline;
3-benzyl-4-(3-trifluoromethyl-phenyl)-8-trifluoromethyl-cinnoline;
3-benzyl-4-(3-methoxy-phenyl)-8-trifluoromethyl-cinnoline;
3-benzyl-4-(3-chlorophenyl)-8-trifluoromethyl-cinnoline;
3-benzyl-4-(4-methoxyphenyl)-8-trifluoromethyl-cinnoline;
3-benzyl-4-(3-{[5-chloro-2-(trifluoromethyl)benzyl]oxy}phenyl)-8-(trifluoromethyl)cinnoline;
3-benzyl-4-(3-{[2-(trifluoromethoxy)benzyl]oxy}phenyl)-8-(trifluoromethyl) cinnoline;
3-benzyl-4-(3-{[5-fluoro-2-(trifluoromethyl)benzyl]oxy}phenyl)-8-(trifluoromethyl)cinnoline;
3-benzyl-4-{3-[(2,5-dichlorobenzyl)oxy]phenyl}-8-(trifluoromethyl)cinnoline;
3-benzyl-4-{3-[(2,6-dichlorobenzyl)oxy]phenyl}-8-(trifluoromethyl)cinnoline;
3-benzyl-4-(3-{[2-fluoro-3-(trifluoromethyl)benzyl]oxy}phenyl)-8-(trifluoromethyl)cinnoline;
3-benzyl-4-(3-{[2-chloro-3-(trifluoromethyl)benzyl]oxy}phenyl)-8-(trifluoromethyl)cinnoline;
3-benzyl-4-{3-[(3,4-dichlorobenzyl)oxy]phenyl}-8-(trifluoromethyl) cinnoline;
3-benzyl-4-{3-[(2-chloro-5-fluorobenzyl)oxy]phenyl}-8-(trifluoromethyl)cinnoline;
3-({3-[3-benzyl-8-(trifluoromethyl)cinnolin-4-yl]phenoxy}methyl)benzoic acid;
4-({3-[3-benzyl-8-(trifluoromethyl)cinnolin-4-yl]phenoxy}methyl)benzoic acid;
4-({3-[3-benzyl-8-(trifluoromethyl)cinnolin-4-yl]phenoxy}methyl)-3-chlorobenzoic acid;
4-({3-[3-benzyl-8-(trifluoromethyl)cinnolin-4-yl]phenoxy}methyl)-2-methoxybenzoic acid;
3-benzyl-4-{3-[(1-methyl-1H-indol-2-yl)methoxy]phenyl}-8-(trifluoromethyl)cinnoline;
4-(3-{[2-(trifluoromethoxy)benzyl]oxy}phenyl)-8-(trifluoromethyl)cinnoline;
7-({3-[3-benzyl-8-(trifluoromethyl)cinnolin-4-yl]phenoxy}methyl)-1-methyl-1H-indole-3-carboxylic acid;

3-benzyl-8-chloro-4-(3-{[2-(trifluoromethoxy)benzyl]oxy}phenyl) cinnoline;

3-benzyl-8-chloro-4-(3-{[2-chloro-5-(trifluoromethyl)benzyl]oxy}phenyl)cinnoline;

3-[3-benzyl-8-(trifluoromethyl)cinnolin-4-yl]benzaldehyde;

[4-({3-[3-benzyl-8-(trifluoromethyl)cinnolin-4-yl]benzyl}amino)-2,3-dimethylphenyl]acetic acid; and 3-benzyl-4-{3-[(1-methyl-1H-indol-7-yl)methoxy]phenyl}-8-(trifluoromethyl)cinnoline;

or a pharmaceutically acceptable salt thereof.

\* \* \* \* \*